US012150947B2

(12) United States Patent
Sahin et al.

(10) Patent No.: US 12,150,947 B2
(45) Date of Patent: Nov. 26, 2024

(54) FORMULATION FOR ADMINISTRATION OF RNA

(71) Applicants: BioNTech SE, Mainz (DE); TRON—TRANSLATIONALE ONKOLOGIE AN DER UNIVERSITATSMEDIZIN DER JOHANNES GUTENBERG-UNIVERSITAT MAINZ GGMBH, Mainz (DE)

(72) Inventors: Ugur Sahin, Mainz (DE); Heinrich Haas, Mainz (DE); Annette Vogel, Mainz (DE); Stephanie Erbar, Mainz (DE); Kerstin Walzer, Mainz (DE); Anne Schlegel, Mainz (DE); Sebastian Hörner, Mainz (DE); Jorge Herrero Moreno, Mainz (DE); Thorsten Klamp, Mainz (DE); Sebastian Kreiter, Mainz (DE); Mustafa Diken, Mainz (DE); Phillip Heller, Mainz (DE)

(73) Assignees: BioNTech SE, Mainz (DE); TRON—TRANSLATIONALE ONKOLOGIE AN DER UNIVERSITATSMEDIZIN DER JOHANNES GUTENBERG-UNIVERSITAT MAINZ, Mainz (DE)

( * ) Notice: Subject to any disclaimer, the term of this patent is extended or adjusted under 35 U.S.C. 154(b) by 501 days.

(21) Appl. No.: 16/957,898

(22) PCT Filed: Jan. 10, 2019

(86) PCT No.: PCT/EP2019/050551
§ 371 (c)(1),
(2) Date: Jun. 25, 2020

(87) PCT Pub. No.: WO2019/137999
PCT Pub. Date: Jul. 18, 2019

(65) Prior Publication Data
US 2021/0023100 A1 Jan. 28, 2021

(30) Foreign Application Priority Data
Jan. 11, 2018 (WO) ................ PCT/EP2018/050672

(51) Int. Cl.
A61K 31/70 (2006.01)
A61K 9/00 (2006.01)
A61K 35/763 (2015.01)
A61K 47/18 (2017.01)

(52) U.S. Cl.
CPC ........... *A61K 31/70* (2013.01); *A61K 9/0019* (2013.01); *A61K 35/763* (2013.01); *A61K 47/183* (2013.01)

(58) Field of Classification Search
None
See application file for complete search history.

(56) References Cited

U.S. PATENT DOCUMENTS

| 11,020,487 B2 * | 6/2021 | Dohmen ............... A61K 47/59 |
| 2007/0044929 A1 | 3/2007 | Mohan et al. |
| 2007/0219365 A1 | 9/2007 | Joyce et al. |
| 2010/0285111 A1 | 11/2010 | Ko et al. |
| 2012/0237565 A1 | 9/2012 | Mirosevich et al. |
| 2016/0074506 A1 | 3/2016 | Jain et al. |
| 2016/0128944 A1 | 5/2016 | Chawrai et al. |
| 2019/0321458 A1 * | 10/2019 | Sahin .................... A61K 47/26 |

FOREIGN PATENT DOCUMENTS

| EP | 3 034 539 | 6/2016 |
| RU | 2746118 C2 | 4/2021 |
| WO | 2008/119827 | 10/2008 |
| WO | 2014145839 A2 | 9/2014 |
| WO | 2016097377 A1 | 6/2016 |
| WO | 2016165825 A1 | 10/2016 |
| WO | 2017053851 A1 | 3/2017 |
| WO | 2017162266 A1 | 9/2017 |
| WO | 2018010815 A1 | 1/2018 |
| WO | 2018011406 A1 | 1/2018 |

OTHER PUBLICATIONS

International Search Report and Written Opinion corresponding to International Patent Application No. PCT/EP2019/050551, mailed Mar. 21, 2019.
Rosenkranz et al., "Polyethylenimine-based polyplex nanoparticles and features of their behavior in cells and tissues", Russian Chemical Bulletin, Springer New York LLC, vol. 64, No. 12, Sep. 20, 2016, pp. 2749-2755, XP063059093.
Sajeesh et al., "Long dsRNA-Mediated RNA Interference and Immunostimulation: A Targeted Delivery Approach Using Polyethyleneimine Based Nano-Carriers", Molecular Pharmaceutics, vol. 11, No. 3, Mar. 3, 2014, pp. 872-884, XP055330364.
Pahle et al., "Vectors and strategies for nonviral cancer gene therapy", Expert Opinion on Biological Therapy, vol. 16, No. 4, Jan. 13, 2016, pp. 443-461, XP055330366.
International Preliminary Report on Patentability corresponding to International Patent Application No. PCT/ EP2019/050551, mailed Jul. 23, 2020, 8 pages.
Thomas Démoulins, PhD., et al. "Polyethylenimine-based polyplex delivery of self-replicating RNA vaccines" Nanomedicine: Nanotechnology, Biology and Medicine, 2016, vol. 12, pp. 711-722.

* cited by examiner

*Primary Examiner* — Celeste A Roney
(74) *Attorney, Agent, or Firm* — MCANDREWS HELD & MALLOY, LTD

(57) ABSTRACT

The present invention relates to compositions comprising polyplex formulations for delivery of RNA to a target organ or a target cell after parenteral administration, in particular after intramuscular administration. More precisely, the present invention relates to formulations for administration of RNA such as self-replicating RNA, in particular by intramuscular injection. In more detail, the formulations comprise polyplex particles from single stranded RNA and a polyalkyleneimine.

16 Claims, 40 Drawing Sheets

FORMULATION FOR ADMINISTRATION OF RNA

The present application is filed pursuant to 35 U.S.C. 371 as a U.S. National Phase application of International Application No. PCT/EP2019/050551, which was filed on Jan. 10, 2019, and claims priority to International Application No. PCT/EP2018/050672, which was filed with the European Patent Office on Jan. 11, 2018. The entire text of the aforementioned applications are incorporated by reference in their entirety.

TECHNICAL FIELD OF THE INVENTION

The present invention relates to compositions comprising polyplex formulations for delivery of RNA to a target organ or a target cell after parenteral administration, in particular after intramuscular administration. More precisely, the present invention relates to formulations for administration of RNA such as self-replicating RNA, in particular by intramuscular injection. In more detail, the polyplex particles comprise single stranded RNA, preferably self-replicating or self-amplifying RNA, and a polyalkyleneimine. The RNA may encode a protein of interest, such as a pharmaceutically active protein. The RNA is taken up by the cell and the RNA is preferably translated into a peptide or protein, which may exhibit its physiological activity. The compositions of the invention are applicable for inducing or enhancing an immune response. They are also useful in a prophylactic and/or therapeutic treatment of a disease involving an antigen such as a protein. Furthermore, the present invention relates to methods for producing stable compositions comprising RNA-polyplex formulations, said RNA-polyplex formulations comprising single stranded RNA and a polyalkyleneimine. RNA-polyplex particle formulations described herein can be either frozen and thawed, or dehydrated and rehydrated without loss of the product quality and, in particular, without substantial loss of RNA activity. In particular, RNA-polyplex particle formulations described herein can be frozen or dehydrated by freeze drying, spray drying or related methods, enabling to obtain extended shelf life of the products with respect to liquid storage. Furthermore RNA-polyplex particle formulations described herein may be compliant to the requirements for pharmaceutical products, more specifically referring to the requirements for GMP manufacturing and the requirements for the quality of pharmaceutical products for parenteral application. RNA-polyplex formulations described herein are in particular useful for vaccination of humans or animals, e.g. against infectious diseases.

BACKGROUND OF THE INVENTION

The introduction of foreign nucleic acids encoding one or more polypeptides for prophylactic and therapeutic purposes has been a goal of biomedical research for many years. Prior art approaches share the delivery of a nucleic acid molecule to a target cell or organism, but differ in the type of nucleic-acid molecule and/or delivery system: influenced by safety concerns associated with the use of deoxyribonucleic acid (DNA) molecules, ribonucleic acid (RNA) molecules have received growing attention in the recent years. Various approaches have been proposed, including administration of single stranded or double-stranded RNA, in the form of naked RNA, or in complexed or packaged form, e.g. in non-viral or viral delivery vehicles. In viruses and in viral delivery vehicles, the nucleic acid is typically encapsulated by proteins and/or lipids (virus particle). For example, engineered RNA virus particles derived from RNA viruses have been proposed as delivery vehicle for treating plants (WO 2000/053780 A2) or for vaccination of mammals (Tubulekas et al., 1997, Gene, vol. 190, pp. 191-195). In view of safety concerns, the medical and veterinary community is reluctant to administer RNA virus particles to humans or animals. Non-viral delivery vehicles that could be applicable to RNA have been extensively investigated for development of gene delivery based therapeutics. However, for various reasons translation of non-viral gene delivery approaches into clinical practice has not been very successful. Reasons may be associated with unsatisfying levels of gene expression, technological and regulatory problems related to pharmaceutical development of such complex products, and safety reasons.

Thus, there is a need for pharmaceutical products for safe and efficient delivery of RNA encoding a protein with a therapeutic value, such as a vaccine, in patients and animals. As described herein, the aspects and embodiments of the present invention address this need.

SUMMARY OF THE INVENTION

Immunotherapeutic strategies represent promising options for the prevention and therapy of e.g. infectious diseases and cancer diseases. The identification of a growing number of pathogen- and tumor-associated antigens led to a broad collection of suitable targets for immunotherapy. The present invention embraces improved agents and methods suitable for efficient expression of antigens, suitable for immunotherapeutic treatment for the prevention and therapy of diseases.

In one aspect, the invention relates to a pharmaceutical composition comprising:
  (a) single stranded RNA; and
  (b) polyalkyleneimine.

In a further aspect, the invention relates to a composition comprising:
  (a) single stranded RNA; and
  (b) polyalkyleneimine
  for use as a pharmaceutical.

In one embodiment of all aspects of the invention, the molar ratio of the number of nitrogen atoms (N) in the polyalkyleneimine to the number of phosphor atoms (P) in the single stranded RNA (N:P ratio) is 1.0 to 30, preferably 2.0 to 15.0, more preferably 6.0 to 12.0.

In a further aspect, the invention relates to a composition comprising:
  (a) single stranded RNA; and
  (b) polyalkyleneimine
  wherein the molar ratio of the number of nitrogen atoms (N) in the polyalkyleneimine to the number of phosphor atoms (P) in the single stranded RNA (N:P ratio) is 1.0 to 30.0, preferably 2.0 to 15.0, more preferably 6.0 to 12.0.

In one embodiment of all aspects of the invention, the ionic strength of the composition is 50 mM or less, preferably wherein the concentration of positively charged monovalent ions is 25 mM or less and the concentration of free positively charged divalent cationic ions is 20 µM or less.

In a further aspect, the invention relates to a composition comprising:
  (a) single stranded RNA; and
  (b) polyalkyleneimine
  wherein the ionic strength is 50 mM or less.

In one embodiment, the concentration of positively charged monovalent ions is 25 mM or less and the concentration of positively charged divalent cationic ions is 20 μM or less.

In one embodiment of all aspects of the invention, the composition is for intramuscular administration such as by intramuscular injection.

In one embodiment of all aspects of the invention, the single stranded RNA and the polyalkyleneimine are present in polyplex particles.

In one embodiment of all aspects of the invention, the polyalkyleneimine comprises the following general formula (I):

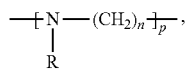

wherein
R is H, an acyl group or a group comprising the following general formula (II):

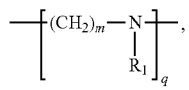

wherein $R_1$ is H or a group comprising the following general formula (III):

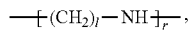

n, m, and l are independently selected from integers from 2 to 10; and
p, q, and r are integers, wherein the sum of p, q, and r is such that the average molecular weight of the polymer is $1.5 \cdot 10^2$ to $10^7$ Da, preferably 5000 to $10^5$ Da, more preferably 10000 to 40000 Da, more preferably 15000 to 30000 Da, even more preferably 20000 to 25000 Da.

In one embodiment, n, m, and l are independently selected from 2, 3, 4, and 5, preferably from 2 and 3. In one embodiment, $R_1$ is H. In one embodiment, R is H or an acyl group.

In one embodiment of all aspects of the invention, the polyalkyleneimine comprises polyethylenimine and/or polypropylenimine, preferably polyethyleneimine.

In one embodiment of all aspects of the invention, at least 92% of the N atoms in the polyalkyleneimine are protonatable.

In one embodiment of all aspects of the invention, the composition of the invention comprises one or more additives. In one embodiment, the one or more additives are selected from the group consisting of buffering substances, saccharides, stabilizers, cryoprotectants, lyoprotectants, and chelating agents. In one embodiment of all aspects of the invention, the composition of the invention comprises one or more polymers. In one embodiment, the buffering substances comprise at least one selected from the group consisting of 4-(2-hydroxyethyl)-1-piperazineethanesulfonic acid (HEPES), 2-(N-morpholino)ethanesulfonic acid (MES), 3-morpholino-2-hydroxypropanesulfonic acid (MOPSO), acetic acid buffering systems and analogues, phosphatic acid buffering systems, or citric acid buffering systems. In one embodiment of all aspects of the invention, the composition of the invention comprises buffers for buffering in the pH range between 4 and 8, preferably between 5 and 7.5. Examples for such buffer systems are acetate buffers or HEPES buffers or phosphate buffers or acetic acid buffers. In one embodiment, the saccharides comprise at least one selected from the group consisting of monosaccharides, disaccharides, trisaccharides, oligosaccharides, and polysachharides, preferably from glucose, trehalose, saccharose and dextran. In one embodiment, the additive is a dextran with a mean molar mass between 1 kDa and 100 kDa. In one embodiment, the cryoprotectants comprise at least one selected from the group consisting of glycols, such as ethylene glycol, propylene glycol, and glycerol. In one embodiment, the chelating agent comprises EDTA. In one embodiment, the lipids comprise at least one selected from the group consisting of cationic lipids, neutral lipids, and anionic lipids. In one embodiment, the composition of the invention comprises one or more block copolymers comprising ethylene oxide and propylene oxide building blocks. In one embodiment, the composition of the invention comprises copolymers comprising ethylene diamine groups. In one embodiment, the composition of the invention comprises an amphiphilic block copolymer, preferably comprising ethylene oxide and propylene oxide building blocks, optionally comprising also ethylene diamine groups.

In one embodiment of all aspects of the invention, the composition comprises HEPES buffered glucose (HBG or HBGx1), MES-buffered glucose (MBG or MBGx1), Acetate buffered glucose (ABG) or HEPES buffered trehalose (HBT or HBTx1). In one embodiment of all aspects of the invention, the composition comprises glucose or trehalose or saccharose in an acetic acid buffer with a concentration in the range from 0.1 mM to 10 mM. In one embodiment of all aspects of the invention, the composition comprises glucose or trehalose or saccharose in a phosphate buffer with a concentration in the range from 0.1 mM to 10 mM.

In one embodiment of all aspects of the invention, the z-average size of the particles is less than 200 nm, preferably less than 150 nm and more preferably less than 100 nm. In one embodiment, the z-average size of the particles is between 50 nm and 200 nm. In one embodiment of all aspects of the invention, the Zeta-potential of the particles is 20 mV or more, preferably 25 to 40 mV. In one embodiment of all aspects of the invention, the electrophoretic mobility (ρ) of the particles is between 1 to 1.6 μm*cm/V*S. In one embodiment of all aspects of the invention, the z-average size of the particles and/or the Zeta-potential and/or the electrophoretic mobility are determined in a suspension comprising the polyplex particles and HEPES buffered glucose (HBG) or HEPES buffered trehalose (HBT). In one embodiment, the HBG comprises 5% glucose (w/v) and 10 mM HEPES, pH 7.1 or the HBT comprises 10% trehalose (w/v) and 10 mM HEPES, pH 7.1. In one embodiment, the z-average size of the particles is determined by dynamic light scattering and data analysis by cumulant algorithm. In one embodiment, the translation diffusion coefficient is measured by dynamic light scattering. Then, Stock-Einstein equation is used in order to calculate the Z-average. In one embodiment, the electrophoretic mobility is measured by laser-Doppler electrophoresis. Then, Henry equation or Smoluchowski equation is used in order to calculate the Zeta-potential.

In one embodiment of all aspects of the invention, the particles are neutral or positively charged, preferably at physiological pH or at a pH between 4.5 and 7.5.

In one embodiment of all aspects of the invention, the single stranded RNA is a molecule of 6000 to 15000 bases, preferably 9000 to 12000 bases. In one embodiment of all aspects of the invention, the single stranded RNA encodes at least one protein of interest. In one embodiment of all aspects of the invention, the single stranded RNA is a replicon, preferably self-replicating or self-amplifying RNA. In one embodiment, the replicon can be replicated by a replicase from an alphavirus, and wherein the replicon preferably comprises a 5' replication recognition sequence from an alphavirus, or a variant thereof, and a 3' replication recognition sequence from an alphavirus, or a variant thereof. In one embodiment of all aspects of the invention, the single stranded RNA comprises an open reading frame encoding a peptide or protein of interest such as a pharmaceutically active peptide or protein.

In one embodiment of all aspects of the invention, the composition described herein is for use in therapy. In one embodiment of all aspects of the invention, the composition described herein is a vaccine composition.

In a further aspect, the invention relates to a use of a composition described herein for introducing RNA into a cell, in particular for expressing RNA in a cell. In one embodiment, the cell is a muscle cell.

In a further aspect, the invention relates to a use of a composition described herein for intramuscular administration of RNA.

In a further aspect, the invention relates to a method of intramuscular administration of RNA comprising the step of intramuscularly administering the composition described herein.

In a further aspect, the invention relates to a frozen, lyophilized or spray dried composition comprising:
  (a) single stranded RNA; and
  (b) polyalkyleneimine
  wherein the composition comprises a cryoprotectant and/or lyoprotectant, preferably a disaccharide such as trehalose, or a polysaccharide such as dextran.

In one embodiment, the composition further comprises a chelating agent such as EDTA.

In one embodiment, the composition is prepared from an aqueous composition comprising a disaccharide at 5-20% (w/v) and optionally the chelating agent at 20 µM to 10 mM such as 80 µM to 5 mM. In one embodiment, the aqueous composition comprises trehalose, HEPES, and EDTA such as 10% trehalose (w/v), 2.8 mM HEPES, 80 µM EDTA, pH 7.1.

In a further aspect, the invention relates to an aqueous composition obtainable by thawing the frozen composition described herein or reconstituting the lyophilized or spray dried composition described herein.

In a further aspect, the invention relates to a method of preparing a frozen, lyophilized or spray dried composition comprising:
  (i) preparing an aqueous composition comprising single stranded RNA, polyalkyleneimine and a cryoprotectant and/or lyoprotectant, preferably a disaccharide such as trehalose, or a polysaccharide such as dextran and
  (ii) freezing, lyophilizing or spray drying the composition.

In one embodiment, the aqueous composition further comprises a chelating agent such as EDTA. In one embodiment, the aqueous composition comprises the disaccharide at 5-20% (w/v) and optionally the chelating agent at 20 µM to 10 mM such as 80 µM to 5 mM. In one embodiment, the aqueous composition comprises trehalose, HEPES, and EDTA such as 10% trehalose (w/v), 2.8 mM HEPES, 80 µM EDTA, pH 7.1.

In a further aspect, the invention relates to a use of a cryoprotectant and/or lyoprotectant, preferably a disaccharide such as trehalose, or a polysaccharide such as dextran for preparing a frozen, lyophilized or spray dried composition comprising:
  (a) single stranded RNA; and
  (b) polyalkyleneimine.

In one embodiment, the disaccharide is used in combination with a chelating agent such as EDTA.

The frozen or lyophilized or spray dried composition or the aqueous composition for preparing the frozen or lyophilized or spray dried composition may comprise one or more of the following:
  (i) Non-aqueous solvents such as ethylene glycol, glycerol, dimethylsulphoxide, and dimethylformamide.
  (ii) Surfactants such as Tween 80, Brij 35, Brij 30, Lubrol-px, Triton X-10; Pluronic F127 (polyoxyethylene-polyoxypropylene copolymer) also known as poloxamer, poloxamine, and sodium dodecyl sulfate.
  (iii) Dissacharides such as trehalose, sucrose, lactose, and maltose.
  (iv) Polymers (which may have different MWs) such as polyethylene glycol, dextran, poly(vinyl alcohol), hydroxypropyl methylcellulose, gelatin, polyvinylpyrrolidone, hydroxyethyl cellulose, Ficoll, and albumin.
  (v) Amino acids such as glycine, proline, 4-hydroxyproline, L-serine, glutamate, alanine, lysine, sarcosine, and gamma-aminobutyric acid.

In a further aspect, the invention relates to a method for continuous flow manufacturing of RNA polyplex formulations by using continuous flow pumps and a mixing device, where two aqueous fluids are mixed by mm or µm sized channels.

BRIEF DESCRIPTION OF THE DRAWINGS

FIG. 26 A): transfection efficacy of Short linear PEI and Long PEI polyplexes at 250 ng of RNA/well. FIG. 26 B): transfection efficacy of short branched PEI and long PEI polyplexes at 250 ng of RNA/well. Compared to the benchmark in vivo Jet PEI and for the same total NP ratio, higher expression levels in different time frames were achieved with combinations of Short PEI (FIG. 26 A: linear;

FIG. 26 B: branched) and Long PEI (e.g. in vivo jetPEI).

(A) BALB/c mice were immunized once at day 0 with buffer, 1/25 dose of human vaccine or 0.1 µg of PEI-formulated VEEV-saRNA or SFV-saRNA encoding the H1N1/Cf7-HA in a N/P ratio of 12/1.28 and 48 days later, animals were bled and serum was analyzed for antibody against the HA measured by virus neutralization assay (VNT; n=4).

(B) Domestic piglets were immunized once at day 0 with buffer, 1 dose of human vaccine or 90 µg of PEI-formulated VEEV-saRNA or SFV-saRNA encoding the H1N1/Cf7-HA in a N/P ratio of 12/1. The pigs were bled at day 14, 21, 28 and 35 after immunization to analyze the neutralizing antibody immune response against the HA performing the VNT (n=8; buffer group n=4).

Group of animals receiving the formulated VEEV-saRNA vaccine developed a similar immune response to animals that were injected with the positive control. SFV-saRNA also led to a development of neutralizing antibody immune response, but to lower titers than after VEEV-saRNA immunization. Mean±SEM are shown in the graph.

Figure 36:
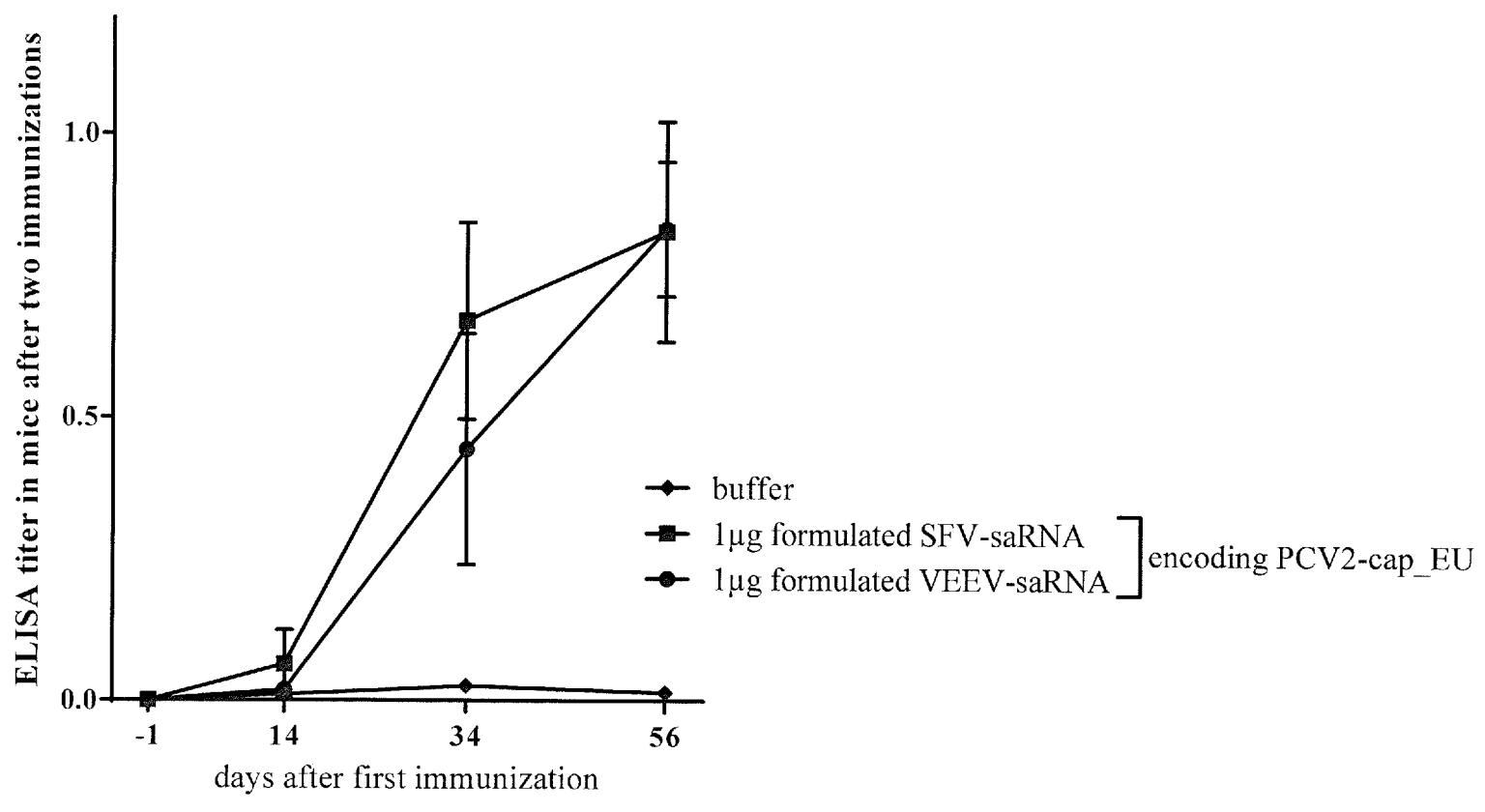

FIG. 36: Animals develop an antibody immune response after intramuscular (i.m.) immunization with PEI-formulated self-amplifying RNA (saRNA) encoding the Porcine Circovirus 2 (PCV2)-cap_EU protein.

BALB/c mice were immunized twice at day 0 and day 35 with buffer, 1 µg of PEI-formulated SFV-saRNA or VEEV-saRNA encoding the PCV2-cap_EU in a N/P ratio of 12/1. At day 14, 34 and 56 animals were bled and sera were analyzed for antibodies against the PCV2-cap as determined by a commercially available ELISA assay (INgezim Circo IgG, Ingenasa; n=4).

Groups of animals receiving the formulated SFV- or VEEV-saRNA vaccines developed a similar antibody response against the PCV2-cap_EU protein. The antibody immune response after a single vaccination with SFV-saRNA was slightly higher than for VEEV-saRNA. After two immunizations, the antibody response was nearly identical for both types of saRNA vaccines. Mean±SEM are shown in the graph.

Figure 37:
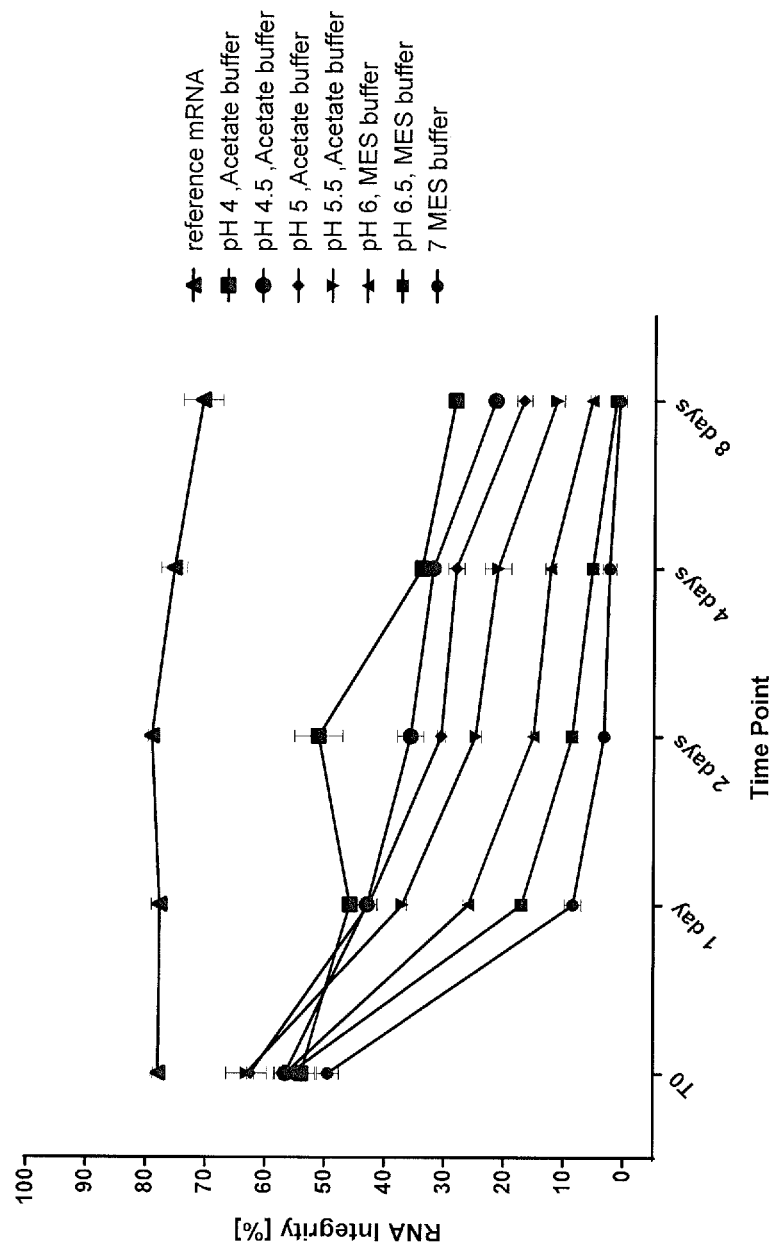

FIG. 37: Replicon-RNA (saRNA) was complexed at N/P12 in different buffer systems and pH conditions. Both types of buffers, acetate or MES buffer, contained a final concentration of 10 mM of the buffering agent and a final concentration of 5% w/v D-Glucose. saRNA/PEI-Polyplexes were stored in the respective buffer at 4° C. for different time periods (1, 2, 4 and 8 days after complexation). Upon complexation of the different formulations, RNA Integrity was directly measured (t=0). RNA Integrity was measured through capillary electrophoresis. The saRNA complexed in polyplexes can be released after 20 min incubation at RT with a strong excess of a polyanion that induces electrostatic interaction with the polymer, releasing the RNA enclosed in the polyplexes. 200 ug of released RNA are used strictly following the protocol provided with the appropriate kit (Standard Sensitivity RNA Analysis Kit DF471) for the capillary electrophoresis assay. For each time point, reference saRNA was used for quantification of the saRNA integrity.

Higher pH values in the formulation buffer lead to significantly increased degradation of the saRNA. The lowest integrity loss of saRNA upon complexation was reached at pH 4 with acetate buffer.

Figure 38:
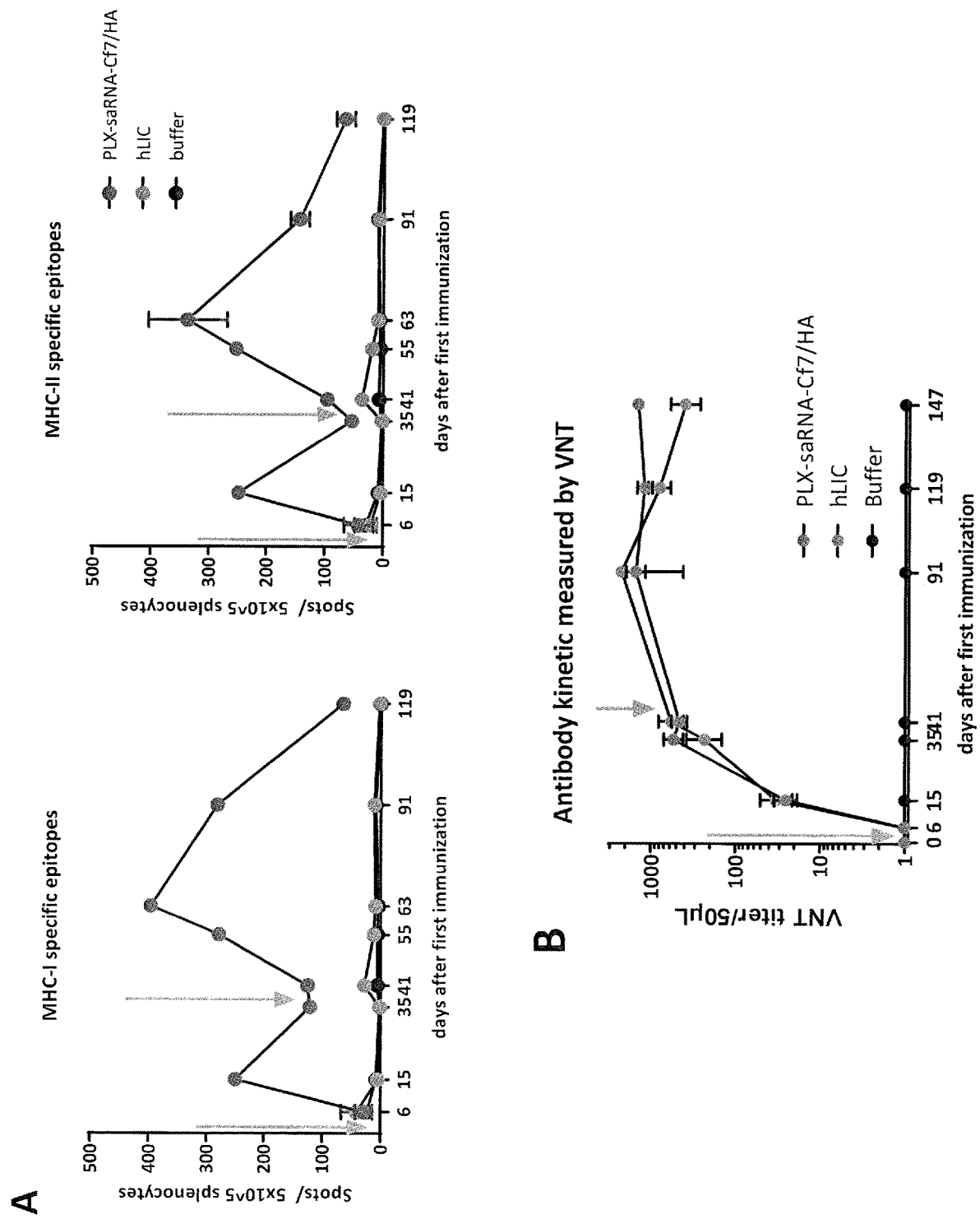

FIG. 38: PEI-formulated saRNA-VEEV encoding the HA of A/California/7/2009 (H1N1, Cf7/HA) induces a strong and longer lasting antibody response compared to commercial vaccine, but additionally induces a strong T cell response which protein based vaccines lack to induce.

BALB/c mice were immunized i.m. twice at day 0 and day 35 (in the graphs, indicated by arrows) with either buffer (black symbols), 20 µL of a human licensed vaccine against seasonal influenza virus strains (Begripal 2016/2017; hLIC; grey symbols) or 0.5 µg of PEI-formulated VEEV-saRNA based vaccine encoding for the Cf7/HA (dark grey symbols). At different time points, mice were sacrificed and A) splenocytes were collected to perform Cf7/HA-specific ELISpot assays with the single cell suspension. For the ELISpot analysis, different CF7/HA specific peptide pools were used to stimulate $CD8^+$ T cell (left) or $CD4^+$ T cell (right) response measured by IFNy secretion. Additionally, serum samples were collected to perform B) anti-Cf4/HA specific Virus neutralization assay to serum antibodies for their functionality to inhibit viral cell infection. Note that for the serological analysis, A/California/4/2009 (H1N1; Cf4) virus was utilized; data indicate mean±SEM (buffer group n=3; vaccine groups n=4).

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., Molecular Cloning: A Laboratory Manual, 2nd Edition, J. Sambrook et al. eds., Cold Spring Harbor Laboratory Press, Cold Spring Harbor 1989).

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to disclose and encompass embodiments which combine the explicitly described embodiments with any number of the disclosed and/or preferred elements. Furthermore, any permutations and combinations of all described elements in this application should be considered disclosed by this description unless the context indicates otherwise.

The term "about" means approximately or nearly, and in the context of a numerical value or range set forth herein preferably means +/−10% of the numerical value or range recited or claimed.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it was individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Unless expressly specified otherwise, the term "comprising" is used in the context of the present document to indicate that further members may optionally be present in addition to the members of the list introduced by "comprising". It is, however, contemplated as a specific embodiment of the present invention that the term "comprising" encompasses the possibility of no further members being present, i.e. for the purpose of this embodiment "comprising" is to be understood as having the meaning of "consisting of".

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the present invention was not entitled to antedate such disclosure.

In the following, definitions will be provided which apply to all aspects of the present invention.

Terms such as "reduce" or "inhibit" as used herein means the ability to cause an overall decrease, preferably of 5% or greater, 10% or greater, 20% or greater, more preferably of 50% or greater, and most preferably 75% or greater, in the level. The term "inhibit" or similar phrases includes a complete or essentially complete inhibition, i.e. a reduction to zero or essentially to zero.

Terms such as "increase" or "enhance" preferably relate to an increase or enhancement by about at least 10%, preferably at least 20%, preferably at least 30%, more preferably at least 40%, more preferably at least 50%, even more preferably at least 80%, and most preferably at least 100%.

"Fragment", with reference to a nucleic acid sequence, relates to a part of a nucleic acid sequence, i.e. a sequence which represents the nucleic acid sequence shortened at the 5'- and/or 3'-end(s). Preferably, a fragment of a nucleic acid sequence comprises at least 80%, preferably at least 90%, 95%, 96%, 97%, 98%, or 99% of the nucleotide residues from said nucleic acid sequence. In the present invention those fragments of RNA molecules are preferred which retain RNA stability and/or translational efficiency.

"Fragment", with reference to an amino acid sequence (peptide or protein), relates to a part of an amino acid sequence, i.e. a sequence which represents the amino acid sequence shortened at the N-terminus and/or C-terminus. A fragment shortened at the C-terminus (N-terminal fragment) is obtainable e.g. by translation of a truncated open reading frame that lacks the 3'-end of the open reading frame. A fragment shortened at the N-terminus (C-terminal fragment) is obtainable e.g. by translation of a truncated open reading frame that lacks the 5'-end of the open reading frame, as long as the truncated open reading frame comprises a start codon that serves to initiate translation. A fragment of an amino acid sequence comprises e.g. at least 1%, at least 2%, at least 3%, at least 4%, at least 5%, at least 10%, at least 20%, at least 30%, at least 40%, at least 50%, at least 60%, at least 70%, at least 80%, at least 90% of the amino acid residues from an amino acid sequence.

The term "ionic strength" refers to the mathematical relationship between the number of different kinds of ionic species in a particular solution and their respective charges. Thus, ionic strength I is represented mathematically by the formula $$I = \frac{1}{2} \cdot \sum_i z_i^2 \cdot c_i$$

in which c is the molar concentration of a particular ionic species and z the absolute value of its charge. The sum $\Sigma$ is taken over all the different kinds of ions (i) in solution.

It is preferred that the ionic strength of the compositions described herein is 50 mM or less, preferably 25 mM or less, preferably 20 mM or less, 19 mM or less, 18 mM or less, 17 mM or less, 16 mM or less, 15 mM or less, 10 mM or less, or 5 mM or less. Preferably, the ionic strength of the compositions described herein is low enough so as to prevent aggregation of polyplex particles.

According to the invention, the term "ionic strength" preferably relates to the presence of monovalent ions. Regarding the presence of divalent ions, in particular divalent cations, their concentration or effective concentration (presence of free ions) due to the presence of chelating agents is preferably sufficiently low so as to prevent degradation of the RNA. In one particularly preferred embodiment, the concentration or effective concentration of divalent ions is below the catalytic level for hydrolysis of the phosphodiester bonds between RNA nucleotides. In one particularly preferred embodiment, the concentration of free divalent ions is 20 µM or less, preferably there are no or essentially no free divalent ions.

It is preferred that the pH of the compositions described herein is between 4 and 8; more preferably between 5.5 and 8 such as between 6 and 7.5, e.g. between 6.5 and 7.1, between 6.5 and 7, or between 6.5 and 6.9.

The term "disaccharide" refers to carbohydrates composed of two monosaccharide residues linked by glycosidic bonds. Representative examples of disaccharides include trehalose, maltose, sucrose, lactose, lactulose, cellobiose, isomaltose, gentibiose, laminarin disaccharide (laminarabiose), chitobiose, xylobiose (xylobiose), inulin disaccharide and mannobiose sugar. A preferred content of the disaccharide in the compositions described herein is 5-20% (w/v) such as 5-15% (w/v), 7-15% (w/v) or 8-12% (w/v). Preferred according to the invention are disaccharides having high glass transition temperatures.

The term "chelating agent" means a compound which forms a chelate with metal ions, preferably divalent or multivalent metal ions. A chelating agent has a plurality of groups, e.g., OH, —COOH, capable of forming a ring structure with metal ions. Examples of chelating agents are: ethylene diamine tetraacetic acid (EDTA), diethylene triamine pentaacetic acid (DTPA), trans-1,2-diamino-cyelohexane tetraacetic acid monohydrate, N-hydroxyethylethylene diamine triacetic acid (HEDTA) citric acid, and phosphoric acid chelating agents (e.g., Dequest 2000). Ethylene diamine tetraacetic acid (EDTA) is preferred according to the invention. It is preferred that the chelating agent is present in the compositions described herein in a concentration of at least 20 µM, at least 40 µM, at least 60 µM, or at least 80 µM. It is preferred that the chelating agent is present in the compositions described herein in a concentration of up to 10 mM, up to 5 mM, up to 2 mM, up to 1 mM, up to 0.5 mM, up to 0.2 mM, or up to 0.1 mM.

The term "freezing" relates to the solidification of a liquid, usually with the removal of heat.

The term "lyophilizing" or "lyophilization" refers to the freeze-drying of a substance by freezing it and then reducing the surrounding pressure to allow the frozen medium in the substance to sublimate directly from the solid phase to the gas phase.

The term "spray drying" refers to spray drying a substance by mixing (heated) gas with a fluid that is atomized (sprayed) within a vessel (spray dryer), where the solvent from the formed droplets evaporates, leading to a dry powder.

The term "cryoprotectant" relates to a substance that is added to a formulation in order to protect the active ingredients during the freezing stages.

The term "lyoprotectant" relates to a substance that is added to a formulation in order to protect the active ingredients during the drying stages.

The term "reconstitute" relates to adding a solvent such as water to a dried product to return it to a liquid state such as its original liquid state.

The term "autologous" is used to describe anything that is derived from the same subject. For example, "autologous cell" refers to a cell derived from the same subject. Introduction of autologous cells into a subject is advantageous because these cells overcome the immunological barrier which otherwise results in rejection.

The term "allogeneic" is used to describe anything that is derived from different individuals of the same species. Two or more individuals are said to be allogeneic to one another when the genes at one or more loci are not identical.

The term "syngeneic" is used to describe anything that is derived from individuals or tissues having identical genotypes, i.e., identical twins or animals of the same inbred strain, or their tissues or cells.

The term "heterologous" is used to describe something consisting of multiple different elements. As an example, the introduction of one individual's cell into a different individual constitutes a heterologous transplant. A heterologous gene is a gene derived from a source other than the subject.

According to the invention, owing to the instability of non-protected RNA, it is advantageous to provide the RNA molecules in complexed form. In particular, in some embodiments, the compositions of the present invention comprise particles comprising RNA and polyalkyleneimine.

When the system according to the present invention is formulated as a particulate formulation, it is possible that each RNA species (e.g. replicon, replicase construct, and optional additional RNA species such as an RNA encoding a protein suitable for inhibiting IFN) is separately formulated as an individual particulate formulation. In that case, each individual particulate formulation will comprise one RNA species. The individual particulate formulations may be present as separate entities, e.g. in separate containers. Such formulations are obtainable by providing each RNA species separately (typically each in the form of an RNA-containing solution) together with a particle-forming agent, thereby allowing the formation of particles. Respective particles will contain exclusively the specific RNA species that is being provided when the particles are formed (individual particulate formulations).

In one embodiment, a composition according to the invention comprises more than one individual particle formulation. Respective compositions are referred to as mixed particulate formulations. Mixed particulate formulations according to the invention are obtainable by forming, separately, individual particulate formulations, as described above, followed by a step of mixing of the individual particulate formulations. By the step of mixing, a formulation comprising a mixed population of RNA-containing particles is obtained (for illustration: e.g. a first population of particles may contain replicon, and a second formulation of particles may contain replicase construct).

Individual particulate populations may be together in one container, comprising a mixed population of individual particulate formulations.

Alternatively, it is possible that all RNA species of the composition (e.g. replicon, replicase construct, and optional additional species such as RNA encoding a protein suitable for inhibiting IFN) are formulated together as a combined particulate formulation. Such formulations are obtainable by providing a combined formulation (typically combined solution) of all RNA species together with a particle-forming agent, thereby allowing the formation of particles. As opposed to a mixed particulate formulation, a combined particulate formulation will typically comprise particles which comprise more than one RNA species. In a combined particulate composition different RNA species are typically present together in a single particle.

In one embodiment, the particulate formulation of the present invention is a nanoparticulate formulation. In that embodiment, the composition according to the present invention comprises RNA in the form of nanoparticles.

In a general definition, the term "nanoparticle" refers to any particle having a diameter of between 1 nm and 1000 nanometers (nm).

In the context of the present invention, the term "particle" relates to a structured entity formed by molecules or molecule complexes. In one embodiment, the term "particle" relates to a micro- or nano-sized structure, such as a micro- or nano-sized compact structure.

The terms "In vivo-jetPEI™", "in vivo jetPEI™", "in vivo jetPEI", "jetPEI", "jet PEI", and "JetPEI" all refer to commercially available In vivo-jetPEI™ Reagent, Cat. #201-50G from Polyplus-Transfection SA (Illkirch, France).

The term "polyplex" as used herein refers to a complex of a polymer and a nucleic acid such as RNA formed via electrostatic interactions. In cases where the polyplex comprises RNA, it may be also referred to as "RNA complex" or "RNA polyplex".

The present invention relates to polyplex particles formed from at least one single stranded RNA and at least one polyalkyleneimine.

In one embodiment, the particles described herein have an average diameter less than about 200 nm, preferably less than about 150 nm, and more preferably less than about 100 nm. In one embodiment, the particles described herein have an average diameter of at least about 30 nm, at least about 40 nm, at least about 50 nm, at least about 60 nm, at least about 70 nm, at least about 80 nm, at least about 90 nm, or at least about 100 nm.

The term "average diameter" refers to the mean hydrodynamic diameter of the particles as measured by dynamic light scattering with data analysis using the so-called cumulant algorithm, which provides as results the so-called $Z_{average}$ with the dimension of a length, and the polydispersity index (PI), which is dimensionless (Koppel, D., J. Chem. Phys. 57, 1972, pp 4814-4820, ISO 13321). Here "average diameter", "diameter" or "size" for particles is used synonymously with this value of the $Z_{average}$.

The term "net charge" relates to the total sum of charges, such as positive and negative charges. For example, if a particle comprises a higher number of negative charges than positive charges, the net charge of the particle is negative. If the particle comprises a higher number of positive charges than negative charges, the net charge of the particle is positive. If the particle comprises an equal number of positive charges and negative charges, the net charge of the particle is neutral, particularly electroneutral. Thus, the net charge of the particle according to the present invention can be negative, positive or neutral. In one embodiment, the net charge of the particle is positive. In one embodiment, the net charge of the particle is negative.

Terms as "charged", "net charge", "negatively charged" or "positively charged" refer to the electric net charge of the given compound or particle when dissolved or suspended in aqueous buffer at the relevant pH (e.g., 7.1).

According to the present invention, the terms "N/P ratio", "NP ratio", "N:P ratio", "N/P" and "NP" refer to the molar ratio of nitrogen atoms (N) in the polyethyleneimine to phosphor atoms (P) in the RNA.

According to the invention, the molar ratio of the number of nitrogen atoms (N) in the polyalkyleneimine to the number of phosphor atoms (P) in the RNA (N/P ratio) is preferably 2.0 to 15.0, preferably 8.0 to 12.0, 6.0 to 14.0 or 6.0 to 12.0.

According to the invention, it is preferred to adjust the compositions described herein to the final N/P ratio in more than 1 step, such as in 2, 3, 4, or more steps. For example, the composition may be adjusted to a first N/P ratio which is lower than the final N/P ratio in a first step, for example, using a long polyalkyleneimine. By adding further polyalkyleneimine, for example, short polyalkyleneimine or long polyalkyleneimine such as the long polyalkyleneimine used in the first step, the N/P ratio may be adjusted to the final N/P ratio. In one embodiment, the final N/P ratio is between 8 and 16, such as between 9 and 14, e.g., between 10 and 12. In one embodiment, the N/P ratio resulting in the first step is between 1 and 6 such as between 2 and 5 such as 3 or 4.

Polyalkyleneimines

The polyalkyleneimine as used herein preferably comprises the following general formula (I):

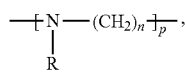

wherein
R is H, an acyl group or a group comprising the following general formula (II):

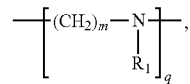

wherein $R_1$ is H or a group comprising the following general formula (III):

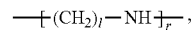

n, m, and l are independently selected from integers from 2 to 10; and p, q, and r are integers, wherein the sum of p, q, and r is such that the average molecular weight of the polymer is $1.5 \cdot 10^2$ to $10^7$ Da, preferably 5000 to $10^5$ Da, more preferably 10000 to 40000 Da, more preferably 15000 to 30000 Da, even more preferably 20000 to 25000 Da.

In one embodiment, n, m, and l are independently selected from 2, 3, 4, and 5, preferably from 2 and 3, and more preferably are 2. In one embodiment, $R_1$ is H. In one embodiment, R is H or an acyl group.

In one embodiment, the polyalkyleneimine comprises polyethylenimine and/or polypropylenimine, preferably polyethyleneimine. A preferred polyalkyleneimine is polyethyleneimine (PEI). The average molecular weight of PEI is preferably $1.5 \cdot 10^2$ to $10^7$ Da, preferably 5000 to $10^5$ Da, more preferably 10000 to 40000 Da, more preferably 15000 to 30000 Da, even more preferably 20000 to 25000 Da.

Preferred according to the invention is linear polyalkyleneimine such as linear polyethyleneimine (PEI). In one embodiment, linear PEI is obtained by a ring-opening isomerization polymerization of 2-ethyl-2-oxazoline to obtain poly(2-ethyl-2-oxazoline) (PEOX; N-propionyl-PEI), which is then acid-hydrolyzed to cleave off the N-propionyl groups to yield PEI.

It is preferred according to the invention that the linear PEI is obtained by complete or essentially complete deacylation of PEOX. For example, PEOX with a molecular weight of 50 kDa gives a linear PEI with a molecular weight of 22 kDa. It is preferred that at least 92%, at least 93%, at least 94%, at least 95%, at least 96%, at least 97%, at least 98%, at least 99%, or essentially 100% of the substituents of the nitrogen atoms in the polyalkyleneimine such as polyethyleneimine are hydrogen (i.e. R in the above formula is H). It is thus preferred that at least 92%, at least 93%, at least 94%, at least 95%, at least 96%, at least 97%, at least 98%, at least 99%, or essentially 100% of the nitrogen atoms in the polyalkyleneimine such as polyethyleneimine are protonatable.

A preferred polyalkyleneimine according to the invention is polyethylenimine (PEI), in particular linear polyethylenimine. Such linear polyethyleneimine preferably has a molar mass between 15 kDa and 30 kDa, and is preferably used in combination with self-replicating or self-amplifying RNA, where the N/P ratio is preferably between 6 and 15, and the linear polyethyleneimine and the self-replicating or self-amplifying RNA are preferably present in polyplex particles having a size of less than 200 nm, preferably less than 150 nm, and even more preferably less than 100 nm.

In one embodiment of the invention, the polyalkyleneimine is a combination of short polyalkyleneimine, such as short polyethyleneimine, of between 0.6 and 11 kDa, preferably of between 1 and 6 kDa or between 1 and 4 kDa such as between 1 and 3 kDa (either linear and/or branched) and long polyalkyleneimine, such as long polyethyleneimine, of between 20 and 40 kDa (either linear and/or branched), where the total N/P ratio is preferably between 8 and 16, such as between 9 and 14, e.g., between 10 and 12. In one embodiment, the N/P ratio between long polyalkyleneimine and RNA is between 1 and 6 such as between 2 and 5 such as 3 or 4.

Polyethylenimine (PEI) is an organic macromolecule with a high cationic-charge-density. PEI may compact nucleic acids into positively charged particles capable of interacting with anionic proteoglycans at the cell surface and facilitating entry of the particles by endocytosis.

Several manufacturing methods exist for PEI. According to the invention, linear polyethylenimine is preferably synthesised and prepared by a method comprising the steps of, from a determined quantity of monomer 2-ethyl-2-oxazoline at a purity superior to 99%, thoroughly drying said quantity of monomer, and polymerising said quantity of monomer for obtaining poly (2-ethyl-2-oxazoline) (PEOX) by:

after thorough drying of a predetermined quantity of acetonitrile, using said acetonitrile as solvent in said quantity of dried monomer, while adding a predetermined quantity of thoroughly dried initiator of the reaction of polymerisation, and mixing them altogether, purifying said obtained PEOX by evaporation to remove said solvent, while performing at least three times successive washing/precipitation steps with methanol and diethyl ether and corresponding filtrations, said operations of drying, polymerising, and purifying being arranged to obtain (i), by performing $^1$H NMR tests, correct identification of said PEOX polymer, confirmation of absence of monomer to a level <1.0% and confirmation of absence of solvent to a level <5.0% and (ii), by performing Gel Permeation Chromatography, a mean of molecular weight (Mw)>23,000 Da and polydispersity (Mw/Mn) of said PEOX <1.5, hydrolysing said PEOX with hydrochloric acid for obtaining said PEI sufficiently efficiently to have, by performing $^1$H-NMR tests, an amount of residual side chains or propionic acid <5% and to identify the PEI as a single peak.

By thoroughly drying a specific quantity of monomer, acetonitrile or the initiator, one should understand obtaining, just before use, a reduction of the humidity below 10 ppm of water, which can be obtained by drying on calcium hydride over 48 h and then by distillation and collecting the monomer above the temperature of 129° C.

One or more of the following features are preferred according to the invention:

(i) the mean of molecular weight (Mw) of the PEOX is such as 40,000 Da<Mw<60,000 Da;
(ii) the monomer/initiator ratio is about 500 (by about one should understand ±5%);
(iii) the monomer/initiator ratio is 480;
(iv) the monomer is at a Purity Superior to 99.95%;
(v) the initiator is mixed with the acetonitrile before addition to the monomer;
(vi) the polymerisation is performed during more than 20 hours at a temperature superior to 85° C.;
(vii) the temperature of polymerisation is superior or equal to 105° C.;
(viii) after the first filtration, the residue is washed freely with a solvent such as MeOH, and after addition of diethyl ether, the poly (2-ethyl-2-oxazoline) is naturally separated as oil from solution, the overall solvent is decanted and said washing and separation is repeated at least four times before drying in vacuo;
(ix) the hydrolysing step comprises removing from the reaction mixture the discharged propionic acid obtained by azeotropic distillation regularly and during at least one day, while monitoring the process of reaction by $^1$H-NMR spectroscopy;
(x) the residue obtained at the end of the process of reaction is diluted in water and evaporated at least three times to remove traces of propionic acid, then the residue is dissolved again in water and filtered before lyophilisation;
(xi) the filtration is provided through a sterile membrane with a dimension of mesh between 0.20 μm and 0.25 μm, particularly a sterile cellular acetate membrane.

Advantageously a linear PEI for use according to the invention is characterized in that the intermediate PEOX has a molecular weight Mw such as 40,000<Mw<60,000 Da.

The degree of polymerization is controlled by the monomer/initiator ratio and by the yield of synthesis. Molecular weight determination can be performed by gel permeation chromatography (GPC).

The term "nucleic acid" according to the invention comprises deoxyribonucleic acid (DNA), ribonucleic acid (RNA), and locked nucleic acid (LNA). According to the invention, nucleic acids comprise genomic DNA, cDNA, mRNA, viral RNA, recombinantly prepared and chemically synthesized molecules. According to the invention, a nucleic acid may be in the form of a single stranded or double-stranded and linear or covalently closed circular molecule. The term "nucleic acid" according to the invention also comprises a chemical derivatization of a nucleic acid on a nucleotide base, on the sugar or on the phosphate, and nucleic acids containing non-natural nucleotides and nucleotide analogs. The nucleic acids described may be isolated and/or recombinant nucleic acids.

The term "isolated" as used herein, is intended to refer to a molecule which is substantially free of other molecules such as other cellular material. The term "isolated nucleic acid" means according to the invention that the nucleic acid has been (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid available to manipulation by recombinant techniques.

The term "recombinant" in the context of the present invention means "made through genetic engineering". Preferably, a "recombinant object" in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring. The term "found in nature" means "present in nature" and includes known objects as well as objects that have not yet been discovered and/or isolated from nature, but that may be discovered and/or isolated in the future from a natural source.

According to the invention "nucleic acid sequence" refers to the sequence of nucleotides in a nucleic acid, e.g. a ribonucleic acid (RNA) or a deoxyribonucleic acid (DNA). The term may refer to an entire nucleic acid molecule (such as to the single strand of an entire nucleic acid molecule) or to a part (e.g. a fragment) thereof.

"3' end of a nucleic acid" refers according to the invention to that end which has a free hydroxy group. In a diagrammatic representation of double-stranded nucleic acids, in particular DNA, the 3' end is always on the right-hand side. "5' end of a nucleic acid" refers according to the invention to that end which has a free phosphate group. In a diagrammatic representation of double-strand nucleic acids, in particular DNA, the 5' end is always on the left-hand side.

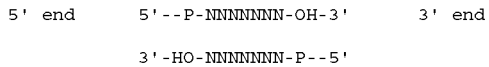

"Upstream" describes the relative positioning of a first element of a nucleic acid molecule with respect to a second element of that nucleic acid molecule, wherein both elements are comprised in the same nucleic acid molecule, and wherein the first element is located nearer to the 5' end of the nucleic acid molecule than the second element of that nucleic acid molecule. The second element is then said to be "downstream" of the first element of that nucleic acid molecule. An element that is located "upstream" of a second element can be synonymously referred to as being located "5" of that second element. For a double-stranded nucleic acid molecule, indications like "upstream" and "downstream" are given with respect to the (+) strand.

According to the invention, the term "gene" refers to a particular nucleic acid sequence which is responsible for producing one or more cellular products and/or for achieving one or more intercellular or intracellular functions. More specifically, said term relates to a nucleic acid section (DNA or RNA) which comprises a nucleic acid coding for a specific protein or a functional or structural RNA molecule.

The term "vector" is used here in its most general meaning and comprises any intermediate vehicles for a nucleic acid which, for example, enable said nucleic acid to be introduced into prokaryotic and/or eukaryotic host cells and, where appropriate, to be integrated into a genome. Such vectors are preferably replicated and/or expressed in the cell. Vectors comprise plasmids, phagemids, virus genomes, and fractions thereof.

In the context of the present invention, the term "RNA" relates to a molecule which comprises ribonucleotide residues and preferably being entirely or substantially composed of ribonucleotide residues and comprises all RNA types described herein. The term "ribonucleotide" relates to a nucleotide with a hydroxyl group at the 2'-position of a β-D-ribofuranosylgroup. The term "RNA" comprises double-stranded RNA, single stranded RNA, isolated RNA such as partially or completely purified RNA, essentially pure RNA, synthetic RNA, and recombinantly generated RNA such as modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs, particularly analogs of naturally-occurring RNAs. The RNA used according to the present invention may have a known composition, or the composition of the RNA may be partially or entirely unknown.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

The term "translation efficiency" relates to the amount of translation product provided by an RNA molecule within a particular period of time.

According to the invention, "double-stranded RNA" or "dsRNA" means RNA with two partially or completely complementary strands.

According to the invention, RNA is preferably single stranded RNA (ssRNA). The term "single stranded RNA" generally refers to an RNA molecule to which no complementary nucleic acid molecule (typically no complementary RNA molecule) is associated. Single stranded RNA may contain self-complementary sequences that allow parts of the RNA to fold back and to form secondary structure motifs including without limitation base pairs, stems, stem loops and bulges. Single stranded RNA can exist as minus strand [(−) strand] or as plus strand [(+) strand]. The (+) strand is the strand that comprises or encodes genetic information. The genetic information may be for example a polynucleotide sequence encoding a protein. When the (+) strand RNA encodes a protein, the (+) strand may serve directly as template for translation (protein synthesis). The (−) strand is the complement of the (+) strand. In the case of double-stranded RNA, (+) strand and (−) strand are two separate RNA molecules, and both these RNA molecules associate with each other to form a double-stranded RNA ("duplex RNA").

Particularly preferred single stranded RNA according to the invention is mRNA and replicon-RNA such as self-replicating RNA. According to the present invention, the RNA can be coding RNA, i.e. RNA encoding a peptide or protein. Preferably, the RNA is pharmaceutically active RNA.

A "pharmaceutically active RNA" is a RNA that encodes a pharmaceutically active peptide or protein such as an antigen or an immunologically active compound (which does not encode an antigen) or is pharmaceutically active in its own, e.g., it has one or more pharmaceutical activities such as those described for pharmaceutically active proteins.

According to the invention, the term "RNA encoding a peptide or protein" means that the RNA, if present in the appropriate environment, preferably within a cell, can direct the assembly of amino acids to produce the peptide or protein during the process of translation. Preferably, coding RNA according to the invention is able to interact with the cellular translation machinery allowing translation of the coding RNA to yield a peptide or protein.

According to the invention, the term "mRNA" means "messenger-RNA" and relates to a transcript which is typically generated by using a DNA template and encodes a peptide or protein. Typically, mRNA comprises a 5'-UTR, a protein coding region, a 3'-UTR, and a poly(A) sequence. mRNA may be generated by in vitro transcription from a DNA template. The in vitro transcription methodology is known to the skilled person. For example, there is a variety of in vitro transcription kits commercially available. According to the invention, mRNA may be modified by stabilizing modifications and capping.

The term "untranslated region" or "UTR" relates to a region in a DNA molecule which is transcribed but is not translated into an amino acid sequence, or to the corresponding region in an RNA molecule, such as an mRNA molecule. An untranslated region (UTR) can be present 5' (upstream) of an open reading frame (5'-UTR) and/or 3' (downstream) of an open reading frame (3'-UTR).

A 3'-UTR, if present, is located at the 3' end of a gene, downstream of the termination codon of a protein-encoding region, but the term "3'-UTR" does preferably not include the poly(A) tail. Thus, the 3'-UTR is upstream of the poly(A) tail (if present), e.g. directly adjacent to the poly(A) tail. A 5'-UTR, if present, is located at the 5' end of a gene, upstream of the start codon of a protein-encoding region. A 5'-UTR is downstream of the 5'-cap (if present), e.g. directly adjacent to the 5'-cap. 5'- and/or 3'-untranslated regions may, according to the invention, be functionally linked to an open reading frame, so as for these regions to be associated with the open reading frame in such a way that the stability and/or translation efficiency of the RNA comprising said open reading frame are increased.

According to the invention, the terms "poly(A) sequence" or "poly(A) tail" refer to an uninterrupted or interrupted sequence of adenylate residues which is typically located at the 3' end of an RNA molecule. An uninterrupted sequence is characterized by consecutive adenylate residues. In nature, an uninterrupted poly(A) sequence is typical. While a poly(A) sequence is normally not encoded in eukaryotic DNA, but is attached during eukaryotic transcription in the cell nucleus to the free 3' end of the RNA by a template-independent RNA polymerase after transcription, the present invention encompasses poly(A) sequences encoded by DNA.

Terms such as "5'-cap", "cap", "5'-cap structure", or "cap structure" are used synonymously to refer to a dinucleotide that is found on the 5' end of some eukaryotic primary transcripts such as precursor messenger RNA. A 5'-cap is a structure wherein a (optionally modified) guanosine is bonded to the first nucleotide of an mRNA molecule via a 5' to 5' triphosphate linkage (or modified triphosphate linkage in the case of certain cap analogs). The terms can refer to a conventional cap or to a cap analog.

RNA molecules according to the invention may be characterized by a 5'-cap, a 5'-UTR, a 3'-UTR, a poly(A) sequence, and/or adaptation of the codon usage.

RNA molecules for use according to the invention preferably have a size of more than 2000 bases, preferably more than 3000 bases, more than 4000 bases, more than 5000 bases, more than 6000 bases, more than 7000 bases, more than 8000 bases, more than 9000 bases, or more than 10000 bases. RNA molecules for use according to the invention preferably have a size of 6000 to 20000 bases, preferably 6000 to 15000 bases, preferably 9000 to 12000 bases.

According to the invention, the term "expression" is used in its most general meaning and comprises production of RNA and/or protein. It also comprises partial expression of nucleic acids. Furthermore, expression may be transient or stable. With respect to RNA, the term "expression" or "translation" relates to the process in the ribosomes of a cell by which a strand of coding RNA (e.g. messenger RNA) directs the assembly of a sequence of amino acids to make a peptide or protein.

The terms "transcription" and "transcribing" relate to a process during which a nucleic acid molecule with a particular nucleic acid sequence (the "nucleic acid template") is read by an RNA polymerase so that the RNA polymerase produces a single stranded RNA molecule. During transcription, the genetic information in a nucleic acid template is transcribed. The nucleic acid template may be DNA; however, e.g. in the case of transcription from an alphaviral nucleic acid template, the template is typically RNA. Subsequently, the transcribed RNA may be translated into protein. According to the present invention, the term "transcription" comprises "in vitro transcription", wherein the term "in vitro transcription" relates to a process wherein RNA, in particular mRNA, is in vitro synthesized in a cell-free system. Preferably, cloning vectors are applied for the generation of transcripts. These cloning vectors are generally designated as transcription vectors and are according to the present invention encompassed by the term "vector". The cloning vectors are preferably plasmids. According to the present invention, RNA preferably is in vitro transcribed RNA (IVT-RNA) and may be obtained by in vitro transcription of an appropriate DNA template. The promoter for controlling transcription can be any promoter for any RNA polymerase. A DNA template for in vitro transcription may be obtained by cloning of a nucleic acid, in particular cDNA, and introducing it into an appropriate vector for in vitro transcription. The cDNA may be obtained by reverse transcription of RNA.

The single stranded nucleic acid molecule produced during transcription typically has a nucleic acid sequence that is the complementary sequence of the template.

According to the invention, the terms "template" or "nucleic acid template" or "template nucleic acid" generally refer to a nucleic acid sequence that may be replicated or transcribed.

The term "expression control sequence" comprises according to the invention promoters, ribosome-binding sequences and other control elements which control transcription of a gene or translation of the derived RNA. In particular embodiments of the invention, the expression control sequences can be regulated. The precise structure of expression control sequences may vary depending on the species or cell type but usually includes 5'-untranscribed and 5'- and 3'-untranslated sequences involved in initiating transcription and translation, respectively. More specifically, 5'-untranscribed expression control sequences include a promoter region which encompasses a promoter sequence for transcription control of the functionally linked gene. Expression control sequences may also include enhancer sequences or upstream activator sequences. An expression control sequence of a DNA molecule usually includes 5'-untranscribed and 5'- and 3'-untranslated sequences such as TATA box, capping sequence, CAAT sequence and the like. An expression control sequence of alphaviral RNA may include a subgenomic promoter and/or one or more conserved sequence element(s). A specific expression control sequence according to the present invention is a subgenomic promoter of an alphavirus, as described herein.

The term "promoter" or "promoter region" refers to a nucleic acid sequence which controls synthesis of a transcript, e.g. a transcript comprising a coding sequence, by providing a recognition and binding site for RNA polymerase. The promoter region may include further recognition or binding sites for further factors involved in regulating transcription of said gene. A promoter may control transcription of a prokaryotic or eukaryotic gene. A promoter may be "inducible" and initiate transcription in response to an inducer, or may be "constitutive" if transcription is not controlled by an inducer. An inducible promoter is expressed only to a very small extent or not at all, if an inducer is absent. In the presence of the inducer, the gene is "switched on" or the level of transcription is increased. This is usually mediated by binding of a specific transcription factor. A specific promoter according to the present invention is a subgenomic promoter of an alphavirus, as described herein. Other specific promoters are genomic plus-strand or negative-strand promoters of an alphavirus.

The term "core promoter" refers to a nucleic acid sequence that is comprised by the promoter. The core promoter is typically the minimal portion of the promoter required to properly initiate transcription. The core promoter typically includes the transcription start site and a binding site for RNA polymerase.

The nucleic acid sequences specified herein, in particular transcribable and coding nucleic acid sequences, may be combined with any expression control sequences which may be homologous or heterologous to said nucleic acid sequences, with the term "homologous" referring to the fact that a nucleic acid sequence is also functionally linked naturally to the expression control sequence, and the term "heterologous" referring to the fact that a nucleic acid sequence is not naturally functionally linked to the expression control sequence.

A nucleic acid sequence, in particular a nucleic acid sequence coding for a peptide or protein, and an expression control sequence are "functionally" linked to one another, if they are covalently linked to one another in such a way that transcription or expression of the transcribable and/or coding nucleic acid sequence is under the control or under the influence of the expression control sequence.

According to the invention, "functional linkage" or "functionally linked" relates to a connection within a functional relationship. A nucleic acid is "functionally linked" if it is functionally related to another nucleic acid sequence. For example, a promoter is functionally linked to a coding sequence if it influences transcription of said coding sequence. Functionally linked nucleic acids are typically adjacent to one another, where appropriate separated by further nucleic acid sequences.

In particular embodiments, a nucleic acid is functionally linked according to the invention to expression control sequences which may be homologous or heterologous with respect to the nucleic acid.

A "polymerase" generally refers to a molecular entity capable of catalyzing the synthesis of a polymeric molecule from monomeric building blocks. A "RNA polymerase" is a molecular entity capable of catalyzing the synthesis of a RNA molecule from ribonucleotide building blocks. A "DNA polymerase" is a molecular entity capable of catalyzing the synthesis of a DNA molecule from deoxy ribonucleotide building blocks. For the case of DNA polymerases and RNA polymerases, the molecular entity is typically a protein or an assembly or complex of multiple proteins. Typically, a DNA polymerase synthesizes a DNA molecule based on a template nucleic acid, which is typically a DNA molecule. Typically, a RNA polymerase synthesizes a RNA molecule based on a template nucleic acid, which is either a DNA molecule (in that case the RNA polymerase is a DNA-dependent RNA polymerase, DdRP), or is a RNA molecule (in that case the RNA polymerase is a RNA-dependent RNA polymerase, RdRP).

A "RNA-dependent RNA polymerase" or "RdRP", is an enzyme that catalyzes the transcription of RNA from an RNA template. In the case of alphaviral RNA-dependent RNA polymerase, sequential synthesis of (−) strand complement of genomic RNA and of (+) strand genomic RNA leads to RNA replication. Alphaviral RNA-dependent RNA polymerase is thus synonymously referred to as "RNA replicase". In nature, RNA-dependent RNA polymerases are typically encoded by all RNA viruses except retroviruses. Typical representatives of viruses encoding a RNA-dependent RNA polymerase are alphaviruses.

According to the present invention, "RNA replication" generally refers to an RNA molecule synthesized based on the nucleotide sequence of a given RNA molecule (template RNA molecule). The RNA molecule that is synthesized may be e.g. identical or complementary to the template RNA molecule. In general, RNA replication may occur via synthesis of a DNA intermediate, or may occur directly by RNA-dependent RNA replication mediated by a RNA-dependent RNA polymerase (RdRP). In the case of alphaviruses, RNA replication does not occur via a DNA intermediate, but is mediated by a RNA-dependent RNA polymerase (RdRP): a template RNA strand (first RNA strand)—or a part thereof—serves as template for the synthesis of a second RNA strand that is complementary to the first RNA strand or to a part thereof. The second RNA strand—or a part thereof—may in turn optionally serve as a template for synthesis of a third RNA strand that is complementary to the second RNA strand or to a part thereof. Thereby, the third RNA strand is identical to the first RNA strand or to a part thereof. Thus, RNA-dependent RNA polymerase is capable of directly synthesizing a complementary RNA strand of a template, and of indirectly synthesizing an identical RNA strand (via a complementary intermediate strand).

According to the invention, the term "template RNA" refers to RNA that can be transcribed or replicated by an RNA-dependent RNA polymerase.

In a preferred embodiment of the invention, the RNA used according to the invention is replicon RNA or simply "a replicon", in particular self-replicating RNA. In one particularly preferred embodiment, the replicon or self-replicating RNA is derived from or comprises elements derived from a ssRNA virus, in particular a positive-stranded ssRNA virus such as an alphavirus.

In general, RNA viruses are a diverse group of infectious particles with an RNA genome. RNA viruses can be sub-grouped into single stranded RNA (ssRNA) and double-stranded RNA (dsRNA) viruses, and the ssRNA viruses can be further generally divided into positive-stranded [(+) stranded] and/or negative-stranded [(−) stranded] viruses. Positive-stranded RNA viruses are prima facie attractive as a delivery system in biomedicine because their RNA may serve directly as template for translation in the host cell.

Alphaviruses are typical representatives of positive-stranded RNA viruses. The hosts of alphaviruses include a wide range of organisms, comprising insects, fish and mammals, such as domesticated animals and humans. Alphaviruses replicate in the cytoplasm of infected cells (for review of the alphaviral life cycle see Jose et al., Future Microbiol., 2009, vol. 4, pp. 837-856). The total genome length of many alphaviruses typically ranges between 11,000 and 12,000 nucleotides, and the genomic RNA typically has a 5'-cap, and a 3' poly(A) tail. The genome of alphaviruses encodes non-structural proteins (involved in transcription, modification and replication of viral RNA and in protein modification) and structural proteins (forming the virus particle). There are typically two open reading frames (ORFs) in the genome. The four non-structural proteins (nsP1-nsP4) are typically encoded together by a first ORF beginning near the 5' terminus of the genome, while alphavirus structural proteins are encoded together by a second ORF which is found downstream of the first ORF and extends near the 3' terminus of the genome. Typically, the first ORF is larger than the second ORF, the ratio being roughly 2:1.

In cells infected by an alphavirus, only the nucleic acid sequence encoding non-structural proteins is translated from the genomic RNA, while the genetic information encoding structural proteins is translatable from a subgenomic transcript, which is an RNA molecule that resembles eukaryotic messenger RNA (mRNA; Gould et al., 2010, Antiviral Res., vol. 87 pp. 111-124). Following infection, i.e. at early stages of the viral life cycle, the (+) stranded genomic RNA directly acts like a messenger RNA for the translation of the open reading frame encoding the non-structural poly-protein (nsP1234). In some alphaviruses, there is an opal stop codon between the coding sequences of nsP3 and nsP4: polyprotein P123, containing nsP1, nsP2, and nsP3, is produced when translation terminates at the opal stop codon, and polyprotein P1234, containing in addition nsP4, is produced upon readthrough of this opal codon (Strauss & Strauss, Microbiol. Rev., 1994, vol. 58, pp. 491-562; Rupp et al., 2015, J. Gen. Virology, vol. 96, pp. 2483-2500). nsP1234 is autoproteolytically cleaved into the fragments nsP123 and nsP4. The polypeptides nsP123 and nsP4 associate to form the (−) strand replicase complex that transcribes (−) stranded RNA, using the (+) stranded genomic RNA as template. Typically at later stages, the nsP123 fragment is completely cleaved into individual proteins nsP1, nsP2 and nsP3 (Shirako & Strauss, 1994, J. Virol., vol. 68, pp. 1874-1885). All four proteins form the (+) strand replicase complex that synthesizes new (+) stranded genomes, using the (−) stranded complement of genomic RNA as template (Kim et al., 2004, Virology, vol. 323, pp. 153-163, Vasiljeva et al., 2003, J. Biol. Chem. vol. 278, pp. 41636-41645).

In infected cells, subgenomic RNA as well as new genomic RNA is provided with a 5'-cap by nsP1 (Pettersson et al. 1980, Eur. J. Biochem. 105, 435-443; Rozanov et al., 1992, J. Gen. Virology, vol. 73, pp. 2129-2134), and provided with a poly-adenylate [poly(A)] tail by nsP4 (Rubach et al., Virology, 2009, vol. 384, pp. 201-208). Thus, both subgenomic RNA and genomic RNA resemble messenger RNA (mRNA).

Alphavirus structural proteins are typically encoded by one single open reading frame under control of a subgenomic promoter (Strauss & Strauss, Microbiol. Rev., 1994, vol. 58, pp. 491-562). The subgenomic promoter is recognized by alphaviral non-structural proteins acting in cis. In particular, alphavirus replicase synthesizes a (+) stranded subgenomic transcript using the (−) stranded complement of genomic RNA as template. The (+) stranded subgenomic transcript encodes the alphavirus structural proteins (Kim et al., 2004, Virology, vol. 323, pp. 153-163, Vasiljeva et al., 2003, J. Biol. Chem. vol. 278, pp. 41636-41645). The subgenomic RNA transcript serves as template for translation of the open reading frame encoding the structural proteins as one poly-protein, and the poly-protein is cleaved to yield the structural proteins. At a late stage of alphavirus infection in a host cell, a packaging signal which is located within the coding sequence of nsP2 ensures selective packaging of genomic RNA into budding virions, packaged by structural proteins (White et al., 1998, J. Virol., vol. 72, pp. 4320-4326).

In infected cells, (−) strand RNA synthesis is typically observed only in the first 3-4 h post infection, and is undetectable at late stages, at which time the synthesis of only (+) strand RNA (both genomic and subgenomic) is observed. According to Frolov et al., 2001, RNA, vol. 7, pp. 1638-1651, the prevailing model for regulation of RNA synthesis suggests a dependence on the processing of the non-structural poly-protein: initial cleavage of the non-structural polyprotein nsP1234 yields nsP123 and nsP4; nsP4 acts as RNA-dependent RNA polymerase (RdRp) that is active for (−) strand synthesis, but inefficient for the generation of (+) strand RNAs. Further processing of the polyprotein nsP123, including cleavage at the nsP2/nsP3 junction, changes the template specificity of the replicase to increase synthesis of (+) strand RNA and to decrease or terminate synthesis of (−) strand RNA.

The synthesis of alphaviral RNA is also regulated by cis-acting RNA elements, including four conserved sequence elements (CSEs; Strauss & Strauss, Microbiol. Rev., 1994, vol. 58, pp. 491-562; and Frolov, 2001, RNA, vol. 7, pp. 1638-1651).

In general, the 5' replication recognition sequence of the alphavirus genome is characterized by low overall homology between different alphaviruses, but has a conserved predicted secondary structure. The 5' replication recognition sequence of the alphavirus genome is not only involved in translation initiation, but also comprises the 5' replication recognition sequence comprising two conserved sequence elements involved in synthesis of viral RNA, CSE 1 and CSE 2. For the function of CSE 1 and 2, the secondary structure is believed to be more important than the linear sequence (Strauss & Strauss, Microbiol. Rev., 1994, vol. 58, pp. 491-562).

In contrast, the 3' terminal sequence of the alphavirus genome, i.e. the sequence immediately upstream of the poly(A) sequence, is characterized by a conserved primary structure, particularly by conserved sequence element 4 (CSE 4), also termed "19-nt conserved sequence", which is important for initiation of (−) strand synthesis.

CSE 3, also termed "junction sequence" is a conserved sequence element on the (+) strand of alphaviral genomic RNA, and the complement of CSE 3 on the (−) strand acts as promoter for subgenomic RNA transcription (Strauss & Strauss, Microbiol. Rev., 1994, vol. 58, pp. 491-562; Frolov et al., 2001, RNA, vol. 7, pp. 1638-1651). CSE 3 typically overlaps with the region encoding the C-terminal fragment of nsP4.

In addition to alphavirus proteins, also host cell factors, presumably proteins, may bind to conserved sequence elements (Strauss & Strauss, supra).

Alphavirus-derived vectors have been proposed for delivery of foreign genetic information into target cells or target organisms. In simple approaches, the open reading frame encoding alphaviral structural proteins is replaced by an open reading frame encoding a protein of interest. Alphavirus-based trans-replication systems rely on alphavirus nucleotide sequence elements on two separate nucleic acid molecules: one nucleic acid molecule encodes a viral replicase (typically as poly-protein nsP1234), and the other nucleic acid molecule is capable of being replicated by said replicase in trans (hence the designation trans-replication system). trans-replication requires the presence of both these nucleic acid molecules in a given host cell. The nucleic acid molecule capable of being replicated by the replicase in trans must comprise certain alphaviral sequence elements to allow recognition and RNA synthesis by the alphaviral replicase.

According to the invention, the term "alphavirus" is to be understood broadly and includes any virus particle that has characteristics of alphaviruses. Characteristics of alphavirus include the presence of a (+) stranded RNA which encodes genetic information suitable for replication in a host cell, including RNA polymerase activity. Further characteristics of many alphaviruses are described e.g. in Strauss & Strauss, Microbiol. Rev., 1994, vol. 58, pp. 491-562. The term "alphavirus" includes alphavirus found in nature, as well as any variant or derivative thereof. In some embodiments, a variant or derivative is not found in nature.

In one embodiment, the alphavirus is an alphavirus found in nature. Typically, an alphavirus found in nature is infectious to any one or more eukaryotic organisms, such as an animal (including a vertebrate such as a human, and an arthropod such as an insect).

An alphavirus found in nature is preferably selected from the group consisting of the following: Barmah Forest virus complex (comprising Barmah Forest virus); Eastern equine encephalitis complex (comprising seven antigenic types of Eastern equine encephalitis virus); Middelburg virus complex (comprising Middelburg virus); Ndumu virus complex (comprising Ndumu virus); Semliki Forest virus complex (comprising Bebaru virus, Chikungunya virus, Mayaro virus and its subtype Una virus, O'Nyong Nyong virus, and its subtype Igbo-Ora virus, Ross River virus and its subtypes Bebaru virus, Getah virus, Sagiyama virus, Semliki Forest virus and its subtype Me Tri virus); Venezuelan equine encephalitis complex (comprising Cabassou virus, Everglades virus, Mosso das Pedras virus, Mucambo virus, Paramana virus, Pixuna virus, Rio Negro virus, Trocara virus and its subtype Bijou Bridge virus, Venezuelan equine encephalitis virus); Western equine encephalitis complex (comprising Aura virus, Babanki virus, Kyzylagach virus, Sindbis virus, Ockelbo virus, Whataroa virus, Buggy Creek virus, Fort Morgan virus, Highlands J virus, Western equine encephalitis virus); and some unclassified viruses including Salmon pancreatic disease virus; Sleeping Disease virus; Southern elephant seal virus; Tonate virus. More preferably, the alphavirus is selected from the group consisting of Semliki Forest virus complex (comprising the virus types as indicated above, including Semliki Forest virus), Western equine encephalitis complex (comprising the virus types as indicated above, including Sindbis virus), Eastern equine encephalitis virus (comprising the virus types as indicated above), Venezuelan equine encephalitis complex (comprising the virus types as indicated above, including Venezuelan equine encephalitis virus).

In a further preferred embodiment, the alphavirus is Semliki Forest virus. In an alternative further preferred embodiment, the alphavirus is Sindbis virus. In an alternative further preferred embodiment, the alphavirus is Venezuelan equine encephalitis virus.

In some embodiments of the present invention, the alphavirus is not an alphavirus found in nature. Typically, an alphavirus not found in nature is a variant or derivative of an alphavirus found in nature, that is distinguished from an alphavirus found in nature by at least one mutation in the nucleotide sequence, i.e. the genomic RNA. The mutation in the nucleotide sequence may be selected from an insertion, a substitution or a deletion of one or more nucleotides, compared to an alphavirus found in nature. A mutation in the nucleotide sequence may or may not be associated with a mutation in a polypeptide or protein encoded by the nucleotide sequence. For example, an alphavirus not found in nature may be an attenuated alphavirus. An attenuated alphavirus not found in nature is an alphavirus that typically has at least one mutation in its nucleotide sequence by which it is distinguished from an alphavirus found in nature, and that is either not infectious at all, or that is infectious but has a lower disease-producing ability or no disease-producing ability at all. As an illustrative example, TC83 is an attenuated alphavirus that is distinguished from the Venezuelan equine encephalitis virus (VEEV) found in nature (McKinney et al., 1963, Am. J. Trop. Med. Hyg., 1963, vol. 12; pp. 597-603).

Members of the alphavirus genus may also be classified based on their relative clinical features in humans: alphaviruses associated primarily with encephalitis, and alphaviruses associated primarily with fever, rash, and polyarthritis.

The term "alphaviral" means found in an alphavirus, or originating from an alphavirus or derived from an alphavirus, e.g. by genetic engineering.

According to the invention, "SFV" stands for Semliki Forest virus. According to the invention, "SIN" or "SINV" stands for Sindbis virus. According to the invention, "VEE" or "VEEV" stands for Venezuelan equine encephalitis virus.

According to the invention, the term "of an alphavirus" or "derived from an alphavirus" refers to an entity of origin from an alphavirus. For illustration, a protein of an alphavirus may refer to a protein that is found in alphavirus and/or to a protein that is encoded by alphavirus; and a nucleic acid sequence of an alphavirus may refer to a nucleic acid sequence that is found in alphavirus and/or to a nucleic acid sequence that is encoded by alphavirus. Preferably, a nucleic acid sequence "of an alphavirus" refers to a nucleic acid sequence "of the genome of an alphavirus" and/or "of genomic RNA of an alphavirus".

According to the invention, the term "alphaviral RNA" refers to any one or more of alphaviral genomic RNA (i.e. (+) strand), complement of alphaviral genomic RNA (i.e. (−) strand), and the subgenomic transcript (i.e. (+) strand), or a fragment of any thereof.

According to the invention, "alphavirus genome" refers to genomic (+) strand RNA of an alphavirus.

According to the invention, the term "native alphavirus sequence" and similar terms typically refer to a (e.g. nucleic acid) sequence of a naturally occurring alphavirus (alphavirus found in nature). In some embodiments, the term "native alphavirus sequence" also includes a sequence of an attenuated alphavirus.

According to the invention, the term "5' replication recognition sequence" preferably refers to a continuous nucleic acid sequence, preferably a ribonucleic acid sequence, that is identical or homologous to a 5' fragment of the alphavirus genome. The "5' replication recognition sequence" is a nucleic acid sequence that can be recognized by an alphaviral replicase. The term 5' replication recognition sequence includes native 5' replication recognition sequences as well as functional equivalents thereof, such as, e.g., functional variants of a 5' replication recognition sequence of alphavirus found in nature. The 5' replication recognition sequence is required for synthesis of the (−) strand complement of alphavirus genomic RNA, and is required for synthesis of (+) strand viral genomic RNA based on a (−) strand template. A native 5' replication recognition sequence typically encodes at least the N-terminal fragment of nsP1; but does not comprise the entire open reading frame encoding nsP1234. In view of the fact that a native 5' replication recognition sequence typically encodes at least the N-terminal fragment of nsP1, a native 5' replication recognition sequence typically comprises at least one initiation codon, typically AUG. In one embodiment, the 5' replication recognition sequence comprises conserved sequence element 1 of an alphavirus genome (CSE 1) or a variant thereof and conserved sequence element 2 of an alphavirus genome (CSE 2) or a variant thereof. The 5' replication recognition sequence is typically capable of forming four stem loops (SL), i.e. SL1, SL2, SL3, SL4. The numbering of these stem loops begins at the 5' end of the 5' replication recognition sequence.

According to the invention, the term "3' replication recognition sequence" preferably refers to a continuous nucleic acid sequence, preferably a ribonucleic acid sequence, that is identical or homologous to a 3' fragment of the alphavirus genome. The "3' replication recognition sequence" is a nucleic acid sequence that can be recognized by an alphaviral replicase. The term 3' replication recognition sequence includes native 3' replication recognition sequences as well as functional equivalents thereof, such as, e.g., functional variants of a 3' replication recognition sequence of alphavirus found in nature. The 3' replication recognition sequence is required for synthesis of the (−) strand complement of alphavirus genomic RNA. In one embodiment, the 3' replication recognition sequence comprises conserved sequence element 4 of an alphavirus genome (CSE 4) or a variant thereof and optionally the poly(A) tail of an alphavirus genome.

The term "conserved sequence element" or "CSE" refers to a nucleotide sequence found in alphavirus RNA. These sequence elements are termed "conserved" because orthologs are present in the genome of different alphaviruses, and orthologous CSEs of different alphaviruses preferably share a high percentage of sequence identity and/or a similar secondary or tertiary structure. The term CSE includes CSE 1, CSE 2, CSE 3 and CSE 4.

According to the invention, the terms "CSE 1" or "44-nt CSE" synonymously refer to a nucleotide sequence that is required for (+) strand synthesis from a (−) strand template. The term "CSE 1" refers to a sequence on the (+) strand; and the complementary sequence of CSE 1 (on the (−) strand) functions as a promoter for (+) strand synthesis. Preferably, the term CSE 1 includes the most 5' nucleotide of the alphavirus genome. CSE 1 typically forms a conserved stem-loop structure. Without wishing to be bound to a particular theory, it is believed that, for CSE 1, the secondary structure is more important than the primary structure, i.e. the linear sequence. In genomic RNA of the model alphavirus Sindbis virus, CSE 1 consists of a consecutive sequence of 44 nucleotides, which is formed by the most 5' 44 nucleotides of the genomic RNA (Strauss & Strauss, Microbiol. Rev., 1994, vol. 58, pp. 491-562).

According to the invention, the terms "CSE 2" or "51-nt CSE" synonymously refer to a nucleotide sequence that is required for (−) strand synthesis from a (+) strand template. The (+) strand template is typically alphavirus genomic RNA or an RNA replicon (note that the subgenomic RNA transcript, which does not comprise CSE 2, does not function as a template for (−) strand synthesis). In alphavirus genomic RNA, CSE 2 is typically localized within the coding sequence for nsP1. In genomic RNA of the model alphavirus Sindbis virus, the 51-nt CSE is located at nucleotide positions 155-205 of genomic RNA (Frolov et al., 2001, RNA, vol. 7, pp. 1638-1651). CSE 2 forms typically two conserved stem loop structures. These stem loop structures are designated as stem loop 3 (SL3) and stem loop 4 (SL4) because they are the third and fourth conserved stem loop, respectively, of alphavirus genomic RNA, counted from the 5' end of alphavirus genomic RNA. Without wishing to be bound to a particular theory, it is believed that, for CSE 2, the secondary structure is more important than the primary structure, i.e. the linear sequence.

According to the invention, the terms "CSE 3" or "junction sequence" synonymously refer to a nucleotide sequence that is derived from alphaviral genomic RNA and that comprises the start site of the subgenomic RNA. The complement of this sequence in the (−) strand acts to promote subgenomic RNA transcription. In alphavirus genomic RNA, CSE 3 typically overlaps with the region encoding the C-terminal fragment of nsP4 and extends to a short non-coding region located upstream of the open reading frame encoding the structural proteins.

According to the invention, the terms "CSE 4" or "19-nt conserved sequence" or "19-nt CSE" synonymously refer to a nucleotide sequence from alphaviral genomic RNA, immediately upstream of the poly(A) sequence in the 3' untranslated region of the alphavirus genome. CSE 4 typically consists of 19 consecutive nucleotides. Without wishing to be bound to a particular theory, CSE 4 is understood to function as a core promoter for initiation of (−) strand synthesis (Jose et al., Future Microbiol., 2009, vol. 4, pp. 837-856); and/or CSE 4 and the poly(A) tail of the alphavirus genomic RNA are understood to function together for efficient (−) strand synthesis (Hardy & Rice, J. Virol., 2005, vol. 79, pp. 4630-4639).

According to the invention, the term "subgenomic promoter" or "SGP" refers to a nucleic acid sequence upstream (5') of a nucleic acid sequence (e.g. coding sequence), which controls transcription of said nucleic acid sequence by providing a recognition and binding site for RNA polymerase, typically RNA-dependent RNA polymerase, in particular functional alphavirus non-structural protein. The SGP may include further recognition or binding sites for further factors. A subgenomic promoter is typically a genetic element of a positive strand RNA virus, such as an alphavirus. A subgenomic promoter of alphavirus is a nucleic acid sequence comprised in the viral genomic RNA. The subgenomic promoter is generally characterized in that it allows initiation of the transcription (RNA synthesis) in the presence of an RNA-dependent RNA polymerase, e.g. functional alphavirus non-structural protein. A RNA (−) strand, i.e. the complement of alphaviral genomic RNA, serves as a template for synthesis of a (+) strand subgenomic transcript, and synthesis of the (+) strand subgenomic transcript is typically initiated at or near the subgenomic promoter. The term "subgenomic promoter" as used herein, is not confined to any particular localization in a nucleic acid comprising such subgenomic promoter. In some embodiments, the SGP is identical to CSE 3 or overlaps with CSE 3 or comprises CSE 3.

The terms "subgenomic transcript" or "subgenomic RNA" synonymously refer to a RNA molecule that is obtainable as a result of transcription using a RNA molecule as template ("template RNA"), wherein the template RNA comprises a subgenomic promoter that controls transcription of the subgenomic transcript. The subgenomic transcript is obtainable in the presence of an RNA-dependent RNA polymerase, in particular functional alphavirus non-structural protein. For instance, the term "subgenomic transcript" may refer to the RNA transcript that is prepared in a cell infected by an alphavirus, using the (−) strand complement of alphavirus genomic RNA as template. However, the term "subgenomic transcript", as used herein, is not limited thereto and also includes transcripts obtainable by using heterologous RNA as template. For example, subgenomic transcripts are also obtainable by using the (−) strand complement of SGP-containing replicons according to the present invention as template. Thus, the term "subgenomic transcript" may refer to a RNA molecule that is obtainable by transcribing a fragment of alphavirus genomic RNA, as well as to a RNA molecule that is obtainable by transcribing a fragment of a replicon according to the present invention.

According to the invention, a nucleic acid construct that is capable of being replicated by a replicase, preferably an alphaviral replicase, is termed replicon. According to the invention, the term "replicon" defines an RNA molecule that can be replicated by RNA-dependent RNA polymerase, yielding—without DNA intermediate—one or multiple identical or essentially identical copies of the RNA replicon. "Without DNA intermediate" means that no deoxyribonucleic acid (DNA) copy or complement of the replicon is formed in the process of forming the copies of the RNA replicon, and/or that no deoxyribonucleic acid (DNA) molecule is used as a template in the process of forming the copies of the RNA replicon, or complement thereof. The replicase function is typically provided by functional alphavirus non-structural protein.

According to the invention, the terms "can be replicated" and "capable of being replicated" generally describe that one or more identical or essentially identical copies of a nucleic acid can be prepared. When used together with the term "replicase", such as in "capable of being replicated by a replicase", the terms "can be replicated" and "capable of being replicated" describe functional characteristics of a nucleic acid molecule, e.g. a RNA replicon, with respect to a replicase. These functional characteristics comprise at least one of (i) the replicase is capable of recognizing the replicon and (ii) the replicase is capable of acting as RNA-dependent RNA polymerase (RdRP). Preferably, the replicase is capable of both (i) recognizing the replicon and (ii) acting as RNA-dependent RNA polymerase.

The expression "capable of recognizing" describes that the replicase is capable of physically associating with the replicon, and preferably, that the replicase is capable of binding to the replicon, typically non-covalently. The term "binding" can mean that the replicase has the capacity of binding to any one or more of a conserved sequence element 1 (CSE 1) or complementary sequence thereof (if comprised by the replicon), conserved sequence element 2 (CSE 2) or complementary sequence thereof (if comprised by the replicon), conserved sequence element 3 (CSE 3) or complementary sequence thereof (if comprised by the replicon), conserved sequence element 4 (CSE 4) or complementary sequence thereof (if comprised by the replicon). Preferably, the replicase is capable of binding to CSE 2 [i.e. to the (+) strand] and/or to CSE 4 [i.e. to the (+) strand], or of binding to the complement of CSE 1 [i.e. to the (−) strand] and/or to the complement of CSE 3 [i.e. to the (−) strand].

The expression "capable of acting as RdRP" means that the replicase is capable to catalyze the synthesis of the (−) strand complement of alphaviral genomic (+) strand RNA, wherein the (+) strand RNA has template function, and/or that the replicase is capable to catalyze the synthesis of (+) strand alphaviral genomic RNA, wherein the (−) strand RNA has template function. In general, the expression "capable of acting as RdRP" can also include that the replicase is capable to catalyze the synthesis of a (+) strand subgenomic transcript wherein a (−) strand RNA has template function, and wherein synthesis of the (+) strand subgenomic transcript is typically initiated at an alphavirus subgenomic promoter.

The expressions "capable of binding" and "capable of acting as RdRP" refer to the capability at normal physiological conditions. In particular, they refer to the conditions inside a cell, which expresses functional alphavirus non-structural protein or which has been transfected with a nucleic acid that codes for functional alphavirus non-structural protein. The cell is preferably a eukaryotic cell. The capability of binding and/or the capability of acting as RdRP can be experimentally tested, e.g. in a cell-free in vitro system or in a eukaryotic cell. Optionally, said eukaryotic cell is a cell from a species to which the particular alphavirus that represents the origin of the replicase is infectious. For example, when the alphavirus replicase from a particular alphavirus is used that is infectious to humans, the normal physiological conditions are conditions in a human cell. More preferably, the eukaryotic cell (in one example human cell) is from the same tissue or organ to which the particular alphavirus that represents the origin of the replicase is infectious.

According to the invention, "compared to a native alphavirus sequence" and similar terms refer to a sequence that is a variant of a native alphavirus sequence. The variant is typically not itself a native alphavirus sequence.

In one embodiment, the RNA replicon comprises a replication recognition sequence such as a 5' replication recognition sequence and a 3' replication recognition sequence. A replication recognition sequence is a nucleic acid sequence that can be recognized by functional alphavirus non-structural protein. In other words, functional alphavirus non-structural protein is capable of recognizing the replication recognition sequence. Preferably, the 5' replication recognition sequence is located at the 5' end of the replicon. In one embodiment, the 5' replication recognition sequence consists of or comprises CSE 1 and 2. Preferably, the 3' replication recognition sequence is located at the 3' end of the replicon (if the replicon does not comprise a poly(A) tail), or immediately upstream of the poly(A) tail (if the replicon comprises a poly(A) tail). In one embodiment, the 3' replication recognition sequence consists of or comprises CSE 4.

In one embodiment, the 5' replication recognition sequence and the 3' replication recognition sequence are capable of directing replication of the RNA replicon in the presence of functional alphavirus non-structural protein. Thus, when present alone or preferably together, these recognition sequences direct replication of the RNA replicon in the presence of functional alphavirus non-structural protein.

It is preferable that a functional alphavirus non-structural protein is provided in cis (encoded as protein of interest by an open reading frame on the replicon) or in trans (encoded as protein of interest by an open reading frame on a separate replicase construct, that is capable of recognizing both the 5' replication recognition sequence and the 3' replication recognition sequence of the replicon. In one embodiment, this is achieved when the 5' and 3' replication recognition sequences are native to the alphavirus from which the functional alphavirus non-structural protein is derived. Native means that the natural origin of these sequences is the same alphavirus. In an alternative embodiment, the 5' replication recognition sequence and/or the 3' replication recognition sequence are not native to the aiphavirus from which the functional alphavirus non-structural protein is derived, provided that the functional alphavirus non-structural protein is capable of recognizing both the 5' replication recognition sequence and the 3' replication recognition sequence of the replicon. In other words, the functional alphavirus non-structural protein is compatible to the 5' replication recognition sequence and the 3' replication recognition sequence. When a non-native functional alphavirus non-structural protein is capable of recognizing a respective sequence or sequence element, the functional alphavirus non-structural protein is said to be compatible (cross-virus compatibility). Any combination of (3'/5') replication recognition sequences and CSEs, respectively, with functional aiphavirus non-structural protein is possible as long as cross-virus compatibility exists. Cross-virus compatibility can readily be tested by the skilled person working the present invention by incubating a functional alphavirus non-structural protein to be tested together with an RNA, wherein the RNA has 3'- and 5' replication recognition sequences to be tested, at conditions suitable for RNA replication, e.g. in a suitable host cell. If replication occurs, the (3'/5') replication recognition sequences and the functional alphavirus non-structural protein are determined to be compatible.

In one embodiment of the invention, the replicon is part of a trans-replication system and thus, the replicon is a trans-replicon. In this embodiment, it is preferred that the RNA replicon does not comprise an open reading frame encoding functional alphavirus non-structural protein. Thus, in this embodiment, the present invention provides a system comprising two nucleic acid molecules: a first RNA construct for expressing functional alphavirus non-structural protein (i.e. encoding functional alphavirus non-structural protein); and a second RNA molecule, the RNA replicon. The RNA construct for expressing functional alphavirus non-structural protein is synonymously referred to herein as "RNA construct for expressing functional alphavirus non-structural protein" or as "replicase construct". The functional alphavirus non-structural protein is as defined above and is typically encoded by an open reading frame comprised by the replicase construct. The functional alphavirus non-structural protein encoded by the replicase construct may be any functional alphavirus non-structural protein that is capable of replicating the replicon. According to the invention, the replicase construct may be present with the replicon(s) within the same composition, e.g. as mixed particulate formulation or combined particulate formulation, or in separate compositions, e.g. as individual particulate formulations. When the system of the present invention is introduced into a cell, preferably a eukaryotic cell, the open reading frame encoding functional alphavirus non-structural protein can be translated. After translation, the functional alphavirus non-structural protein is capable of replicating a separate RNA molecule (RNA replicon) in trans.

Herein, trans (e.g. in the context of trans-acting, trans-regulatory), in general, means "acting from a different molecule" (i.e., intermolecular). It is the opposite of cis (e.g. in the context of cis-acting, cis-regulatory), which, in general, means "acting from the same molecule" (i.e., intramolecular). In the context of RNA synthesis (including transcription and RNA replication), a trans-acting element includes a nucleic acid sequence that contains a gene encoding an enzyme capable of RNA synthesis (RNA polymerase). The RNA polymerase uses a second nucleic acid molecule, i.e. a nucleic acid molecule other than the one by which it is encoded, as template for the synthesis of RNA. Both the RNA polymerase and the nucleic acid sequence that contains a gene encoding the RNA polymerase are said to "act in trans" on the second nucleic acid molecule. In the context of the present invention, the RNA polymerase encoded by the trans-acting RNA may be functional alphavirus non-structural protein. The functional alphavirus non-structural protein is capable of using a second nucleic acid molecule, which is an RNA replicon, as template for the synthesis or RNA, including replication of the RNA replicon. The RNA replicon that can be replicated by the replicase in trans according to the present invention is synonymously referred to herein as "trans-replicon".

According to the present invention, the role of the functional alphavirus non-structural protein is to amplify the replicon, and to prepare a subgenomic transcript, if a sub-genomic promoter is present on the replicon. If the replicon encodes a gene of interest for expression, the expression levels of the gene of interest and/or the duration of expression may be regulated in trans by modifying the levels of the functional alphavirus non-structural protein.

The trans-replication system of the present invention comprises at least two nucleic acid molecules. In a preferred embodiment, the system consists of exactly two RNA molecules, the replicon and the replicase construct. In alternative preferred embodiments, the system comprises more than one replicon, each preferably encoding at least one protein of interest, and also comprises the replicase construct. In these embodiments, the functional alphavirus non-structural protein encoded by the replicase construct can act on each replicon to drive replication and optionally production of subgenomic transcripts, respectively. For example, each replicon may encode a pharmaceutically active peptide or protein. This is advantageous e.g. if vaccination of a subject against several different antigens is desired.

Preferably, the replicase construct lacks at least one conserved sequence element (CSE) that is required for (−) strand synthesis based on a (+) strand template, and/or for (+) strand synthesis based on a (−) strand template. More preferably, the replicase construct does not comprise any alphaviral conserved sequence elements (CSEs). In particular, among the four CSEs of alphavirus (Strauss & Strauss, Microbiol. Rev., 1994, vol. 58, pp. 491-562; Jose et al., Future Microbiol., 2009, vol. 4, pp. 837-856), any one or more of the following CSEs are preferably not present on the replicase construct: CSE 1; CSE 2; CSE 3; CSE 4. Particularly in the absence of any one or more alphaviral CSE, the replicase construct of the present invention resembles typical eukaryotic mRNA much more than it resembles alphaviral genomic RNA.

The replicase construct of the present invention is preferably distinguished from alphaviral genomic RNA at least in that it is not capable of self-replication and/or that it does not comprise an open reading frame under the control of a sub-genomic promoter. When unable to self-replicate, the replicase construct may also be termed "suicide construct".

The replicase construct according to the present invention is preferably a single stranded RNA molecule. The replicase construct according to the present invention is typically a (+) stranded RNA molecule. In one embodiment, the replicase construct of the present invention is an isolated nucleic acid molecule.

In one embodiment, the RNA such as the replicon according to the present invention comprises at least one open reading frame encoding a peptide of interest or a protein of interest. In various embodiments, the peptide or protein of interest is encoded by a heterologous nucleic acid sequence. According to the present invention, the term "heterologous" refers to the fact that a nucleic acid sequence is not naturally functionally or structurally linked to a nucleic sequence such as an alphavirus nucleic acid sequence.

The RNA according to the present invention may encode a single polypeptide or multiple polypeptides. Multiple polypeptides can be encoded as a single polypeptide (fusion polypeptide) or as separate polypeptides. In some embodiments, the RNA according to the present invention may comprise more than one open reading frame, each of which in the case of a replicon may independently be selected to be under the control of a subgenomic promoter or not. Alternatively, a poly-protein or fusion polypeptide comprises individual polypeptides separated by an optionally autocatalytic protease cleavage site (e.g. foot-and-mouth disease virus 2A protein), or an intein.

Proteins of interest may e.g. be selected from the group consisting of reporter proteins, pharmaceutically active peptides or proteins, inhibitors of intracellular interferon (IFN) signaling, and functional alphavirus non-structural protein.

According to the invention, the term "peptide" comprises oligo- and polypeptides and refers to substances which comprise two or more, preferably 3 or more, preferably 4 or more, preferably 6 or more, preferably 8 or more, preferably 10 or more, preferably 13 or more, preferably 16 or more, preferably 20 or more, and up to preferably 50, preferably 100 or preferably 150, consecutive amino acids linked to one another via peptide bonds. The term "protein" refers to large peptides, preferably peptides having at least 151 amino acids, but the terms "peptide" and "protein" are used herein usually as synonyms.

The terms "peptide" and "protein" comprise, according to the invention, substances which contain not only amino acid components but also non-amino acid components such as sugars and phosphate structures, and also comprise substances containing bonds such as ester, thioether or disulfide bonds.

The term "variant" with respect to, for example, nucleic acid and amino acid sequences, according to the invention includes any variants, in particular mutants, viral strain variants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. With respect to nucleic acid molecules, the term "variant" includes degenerate nucleic acid sequences, wherein a degenerate nucleic acid according to the invention is a nucleic acid that differs from a reference nucleic acid in codon sequence due to the degeneracy of the genetic code (e.g. due to adaption of the codon usage). A species homolog is a nucleic acid or amino acid sequence with a different species of origin from that of a given nucleic acid or amino acid sequence. A virus homolog is a nucleic acid or amino acid sequence with a different virus of origin from that of a given nucleic acid or amino acid sequence.

According to the invention, nucleic acid variants include single or multiple nucleotide deletions, additions, mutations, substitutions and/or insertions in comparison with the reference nucleic acid. Deletions include removal of one or more nucleotides from the reference nucleic acid. Addition variants comprise 5'- and/or 3'-terminal fusions of one or more nucleotides, such as 1, 2, 3, 5, 10, 20, 30, 50, or more nucleotides. In the case of substitutions, at least one nucleotide in the sequence is removed and at least one other nucleotide is inserted in its place (such as transversions and transitions). Mutations include abasic sites, crosslinked sites, and chemically altered or modified bases. Insertions include the addition of at least one nucleotide into the reference nucleic acid.

According to the invention, "nucleotide change" can refer to single or multiple nucleotide deletions, additions, mutations, substitutions and/or insertions in comparison with the reference nucleic acid. In some embodiments, a "nucleotide change" is selected from the group consisting of a deletion of a single nucleotide, the addition of a single nucleotide, the mutation of a single nucleotide, the substitution of a single nucleotide and/or the insertion of a single nucleotide, in comparison with the reference nucleic acid. According to the invention, a nucleic acid variant can comprise one or more nucleotide changes in comparison with the reference nucleic acid.

Variants of specific nucleic acid sequences preferably have at least one functional property of said specific sequences and preferably are functionally equivalent to said specific sequences, e.g. nucleic acid sequences exhibiting properties identical or similar to those of the specific nucleic acid sequences.

Preferably the degree of identity between a given nucleic acid sequence and a nucleic acid sequence which is a variant of said given nucleic acid sequence will be at least 70%, preferably at least 75%, preferably at least 80%, more preferably at least 85%, even more preferably at least 90% or most preferably at least 95%, 96%, 97%, 98% or 99%. The degree of identity is preferably given for a region of at least about 30, at least about 50, at least about 70, at least about 90, at least about 100, at least about 150, at least about 200, at least about 250, at least about 300, or at least about 400 nucleotides. In preferred embodiments, the degree of identity is given for the entire length of the reference nucleic acid sequence.

"Sequence similarity" indicates the percentage of amino acids that either are identical or that represent conservative amino acid substitutions. "Sequence identity" between two polypeptide or nucleic acid sequences indicates the percentage of amino acids or nucleotides that are identical between the sequences.

The term "% identical" is intended to refer, in particular, to a percentage of nucleotides which are identical in an optimal alignment between two sequences to be compared, with said percentage being purely statistical, and the differences between the two sequences may be randomly distributed over the entire length of the sequence and the sequence to be compared may comprise additions or deletions in comparison with the reference sequence, in order to obtain optimal alignment between two sequences. Comparisons of two sequences are usually carried out by comparing said sequences, after optimal alignment, with respect to a segment or "window of comparison", in order to identify local regions of corresponding sequences. The optimal alignment for a comparison may be carried out manually or with the aid of the local homology algorithm by Smith and Waterman, 1981, Ads App. Math. 2, 482, with the aid of the local homology algorithm by Needleman and Wunsch, 1970, J. Mol. Biol. 48, 443, and with the aid of the similarity search algorithm by Pearson and Lipman, 1988, Proc. Natl Acad. Sci. USA 85, 2444 or with the aid of computer programs using said algorithms (GAP, BESTFIT, FASTA, BLAST P, BLAST N and TFASTA in Wisconsin Genetics Software Package, Genetics Computer Group, 575 Science Drive, Madison, Wis.).

Percentage identity is obtained by determining the number of identical positions in which the sequences to be compared correspond, dividing this number by the number of positions compared and multiplying this result by 100.

For example, the BLAST program "BLAST 2 sequences" which is available on the website http://www.ncbi.nlm.nih.gov/blast/bl2seq/wblast2.cgi may be used.

A nucleic acid is "capable of hybridizing" or "hybridizes" to another nucleic acid if the two sequences are complementary with one another. A nucleic acid is "complementary" to another nucleic acid if the two sequences are capable of forming a stable duplex with one another. According to the invention, hybridization is preferably carried out under conditions which allow specific hybridization between polynucleotides (stringent conditions). Stringent conditions are described, for example, in Molecular Cloning: A Laboratory Manual, J. Sambrook et al., Editors, $2^{nd}$ Edition, Cold Spring Harbor Laboratory press, Cold Spring Harbor, New York, 1989 or Current Protocols in Molecular Biology, F. M. Ausubel et al., Editors, John Wiley & Sons, Inc., New York and refer, for example, to hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7. After hybridization, the membrane to which the DNA has been transferred is washed, for example, in 2×SSC at room temperature and then in 0.1-0.5×SSC/0.1×SDS at temperatures of up to 68° C.

A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" or "fully complementary" means that all the contiguous residues of a nucleic acid sequence will hydrogen bond with the same number of contiguous residues in a second nucleic acid sequence. Preferably, the degree of complementarity according to the invention is at least 70%, preferably at least 75%, preferably at least 80%, more preferably at least 85%, even more preferably at least 90% or most preferably at least 95%, 96%, 97%, 98% or 99%. Most preferably, the degree of complementarity according to the invention is 100%.

The term "derivative" comprises any chemical derivatization of a nucleic acid on a nucleotide base, on the sugar or on the phosphate. The term "derivative" also comprises nucleic acids which contain nucleotides and nucleotide analogs not occurring naturally. Preferably, a derivatization of a nucleic acid increases its stability.

According to the invention, a "nucleic acid sequence which is derived from a nucleic acid sequence" refers to a nucleic acid may be a variant of the nucleic acid from which it is derived.

In one embodiment, an open reading frame encodes a reporter protein. In that embodiment, the open reading frame comprises a reporter gene. Certain genes may be chosen as reporters because the characteristics they confer on cells or organisms expressing them may be readily identified and measured, or because they are selectable markers. Reporter genes are often used as an indication of whether a certain gene has been taken up by or expressed in the cell or organism population. Preferably, the expression product of the reporter gene is visually detectable. Common visually detectable reporter proteins typically possess fluorescent or luminescent proteins. Examples of specific reporter genes include the gene that encodes jellyfish green fluorescent protein (GFP), which causes cells that express it to glow green under blue light, the enzyme luciferase, which catalyzes a reaction with luciferin to produce light, and the red fluorescent protein (RFP). Variants of any of these specific reporter genes are possible, as long as the variants possess visually detectable properties. For example, eGFP is a point mutant variant of GFP.

According to the invention, in one embodiment, RNA comprises or consists of pharmaceutically active RNA. A "pharmaceutically active RNA" may be RNA that encodes a pharmaceutically active peptide or protein. Preferably, the RNA according to the present invention encodes a pharmaceutically active peptide or protein. Preferably, an open reading frame encodes a pharmaceutically active peptide or protein. Preferably, the RNA comprises an open reading frame that encodes a pharmaceutically active peptide or protein, optionally in the case of an RNA replicon under control of a subgenomic promoter.

A "pharmaceutically active peptide or protein" has a positive or advantageous effect on the condition or disease state of a subject when administered to the subject in a therapeutically effective amount. Preferably, a pharmaceutically active peptide or protein has curative or palliative properties and may be administered to ameliorate, relieve, alleviate, reverse, delay onset of or lessen the severity of one or more symptoms of a disease or disorder. A pharmaceutically active peptide or protein may have prophylactic properties and may be used to delay the onset of a disease or to lessen the severity of such disease or pathological condition. The term "pharmaceutically active peptide or protein" includes entire proteins or polypeptides, and can also refer to pharmaceutically active fragments thereof. It can also include pharmaceutically active analogs of a peptide or protein. The term "pharmaceutically active peptide or protein" includes peptides and proteins that are antigens, i.e., the peptide or protein elicits an immune response in a subject which may be therapeutic or partially or fully protective.

In one embodiment, the pharmaceutically active peptide or protein is or comprises an immunologically active compound or an antigen or an epitope.

According to the invention, the term "immunologically active compound" relates to any compound altering an immune response, preferably by inducing and/or suppressing maturation of immune cells, inducing and/or suppressing cytokine biosynthesis, and/or altering humoral immunity by stimulating antibody production by B cells. In one embodiment, the immune response involves stimulation of an antibody response (usually including immunoglobulin G (IgG)) and/or a cellular response such as a T cell response. Immunologically active compounds may possess potent immunostimulating activity including, but not limited to, antiviral and antitumor activity, and can also down-regulate other aspects of the immune response, for example shifting the immune response away from a $TH_2$ immune response, which is useful for treating a wide range of $TH_2$ mediated diseases.

According to the invention, the term "antigen" or "immunogen" covers any substance that will elicit an immune response. In particular, an "antigen" relates to any substance that reacts specifically with antibodies or T-lymphocytes (T-cells). According to the present invention, the term "antigen" comprises any molecule which comprises at least one epitope. Preferably, an antigen in the context of the present invention is a molecule which, optionally after processing, induces an immune reaction, which is preferably specific for the antigen. According to the present invention, any suitable antigen may be used, which is a candidate for an immune reaction, wherein the immune reaction may be both a humoral as well as a cellular immune reaction. In the context of the embodiments of the present invention, the antigen is preferably presented by a cell, preferably by an antigen presenting cell, in the context of MHC molecules, which results in an immune reaction against the antigen. An antigen is preferably a product which corresponds to or is derived from a naturally occurring antigen. Such naturally occurring antigens may include or may be derived from allergens, viruses, bacteria, fungi, parasites and other infectious agents and pathogens or an antigen may also be a tumor antigen. According to the present invention, an antigen may correspond to a naturally occurring product, for example, a viral protein, or a part thereof. In preferred embodiments, the antigen is a surface polypeptide, i.e. a polypeptide naturally displayed on the surface of a cell, a pathogen, a bacterium, a virus, a fungus, a parasite, an allergen, or a tumor. The antigen may elicit an immune response against a cell, a pathogen, a bacterium, a virus, a fungus, a parasite, an allergen, or a tumor.

The term "disease-associated antigen" is used in it broadest sense to refer to any antigen associated with a disease. A disease-associated antigen is a molecule which contains epitopes that will stimulate a host's immune system to make a cellular antigen-specific immune response and/or a humoral antibody response against the disease. The disease-associated antigen may therefore be used for therapeutic purposes. Disease-associated antigens are preferably associated with infection by microbes, typically microbial antigens, or associated with cancer, typically tumors.

The term "pathogen" refers to pathogenic biological material capable of causing disease in an organism, preferably a vertebrate organism. Pathogens include microorganisms such as bacteria, unicellular eukaryotic organisms (protozoa), fungi, as well as viruses.

The terms "epitope", "antigen peptide", "antigen epitope", "immunogenic peptide" and "MHC binding peptide" are used interchangeably herein and refer to an antigenic determinant in a molecule such as an antigen, i.e., to a part in or fragment of an immunologically active compound that is recognized by the immune system, for example, that is recognized by a T cell, in particular when presented in the context of MHC molecules. An epitope of a protein preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 9, 10, 11, 12, 13, 14, 15, 16, 17, 18, 19, 20, 21, 22, 23, 24, or 25 amino acids in length. According to the invention an epitope may bind to MHC molecules such as MHC molecules on the surface of a cell and thus, may be a "MHC binding peptide" or "antigen peptide". The term "major histocompatibility complex" and the abbreviation "MHC" include MHC class I and MHC class II molecules and relate to a complex of genes which is present in all vertebrates. MHC proteins or molecules are important for signaling between lymphocytes and antigen presenting cells or diseased cells in immune reactions, wherein the MHC proteins or molecules bind peptides and present them for recognition by T cell receptors. The proteins encoded by the MHC are expressed on the surface of cells, and display both self-antigens (peptide fragments from the cell itself) and non-self-antigens (e.g., fragments of invading microorganisms) to a T cell. Preferred such immunogenic portions bind to an MHC class I or class II molecule. As used herein, an immunogenic portion is said to "bind to" an MHC class I or class II molecule if such binding is detectable using any assay known in the art. The term "MHC binding peptide" relates to a peptide which binds to an MHC class I and/or an MHC class II molecule. In the case of class I MHC/peptide complexes, the binding peptides are typically 8-10 amino acids long although longer or shorter peptides may be effective. In the case of class II MHC/peptide complexes, the binding peptides are typically 10-25 amino acids long and are in particular 13-18 amino acids long, whereas longer and shorter peptides may be effective.

In one embodiment, the protein of interest according to the present invention comprises an epitope suitable for vaccination of a target organism. A person skilled in the art will know that one of the principles of immunobiology and vaccination is based on the fact that an immunoprotective reaction to a disease is produced by immunizing an organism with an antigen, which is immunologically relevant with respect to the disease to be treated. According to the present invention, an antigen is selected from the group comprising a self-antigen and non-self-antigen. A non-self-antigen is preferably a bacterial antigen, a virus antigen, a fungus antigen, an allergen or a parasite antigen. It is preferred that the antigen comprises an epitope that is capable of eliciting an immune response in a target organism. For example, the epitope may elicit an immune response against a bacterium, a virus, a fungus, a parasite, an allergen, or a tumor.

In some embodiments the non-self-antigen is a bacterial antigen. In some embodiments, the antigen elicits an immune response against a bacterium which infects animals, including birds, fish and mammals, including domesticated animals. Preferably, the bacterium against which the immune response is elicited is a pathogenic bacterium.

In some embodiments the non-self-antigen is a virus antigen. A virus antigen may for example be a protein, polypeptide or peptide from a virus surface protein, e.g. a membrane-bound glycoprotein, a capsid protein or polypeptide or a spike protein or polypeptide. In some embodiments, the antigen elicits an immune response against a virus which infects animals, including birds, fish and mammals, including domesticated animals. Preferably, the virus against which the immune response is elicited is a pathogenic virus.

In some embodiments the non-self-antigen is a polypeptide or a protein from a fungus. In some embodiments, the antigen elicits an immune response against a fungus which infects animals, including birds, fish and mammals, including domesticated animals. Preferably, the fungus against which the immune response is elicited is a pathogenic fungus.

In some embodiments the non-self-antigen is a polypeptide or protein from a unicellular eukaryotic parasite. In some embodiments, the antigen elicits an immune response against a unicellular eukaryotic parasite, preferably a pathogenic unicellular eukaryotic parasite. Pathogenic unicellular eukaryotic parasites may be e.g. from the genus *Plasmodium*, e.g. *P. falciparum, P. vivax, P. malariae* or *P. ovale*, from the genus *Leishmania*, or from the genus *Trypanosoma*, e.g. *T. cruzi* or *T. brucei*.

In some embodiments the non-self-antigen is an allergenic polypeptide or an allergenic protein. An allergenic protein or allergenic polypeptide is suitable for allergen immunotherapy, also known as hypo-sensitization.

In some embodiments the antigen is a self-antigen, particularly a tumor antigen. Tumor antigens and their determination are known to the skilled person.

In the context of the present invention, the term "tumor antigen" or "tumor-associated antigen" relates to proteins that are under normal conditions specifically expressed in a limited number of tissues and/or organs or in specific developmental stages, for example, the tumor antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2. The tumor antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. In the context of the present invention, the tumor antigen is preferably associated with the cell surface of a cancer cell and is preferably not or only rarely expressed in normal tissues. Preferably, the tumor antigen or the aberrant expression of the tumor antigen identifies cancer cells. In the context of the present invention, the tumor antigen that is expressed by a cancer cell in a subject, e.g., a patient suffering from a cancer disease, is preferably a self-protein in said subject. In preferred embodiments, the tumor antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system. Preferably, the amino acid sequence of the tumor antigen is identical between the tumor antigen which is expressed in normal tissues and the tumor antigen which is expressed in cancer tissues.

Examples for tumor antigens that may be useful in the present invention are p53, ART-4, BAGE, beta-catenin/m, Bcr-abL CAMEL, CAP-1, CASP-8, CDC127/m, CDK4/m, CEA, the cell surface proteins of the claudin family, such as CLAUDIN-6, CLAUDIN-18.2 and CLAUDIN-12, c-MYC, CT, Cyp-B, DAM, ELF2M, ETV6-AML1, G250, GAGE, GnT-V, Gap100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12, MAGE-B, MAGE-C, MART-1/Melan-A, MC1R, Myosin/m, MUC1, MUM-1, -2, -3, NA88-A, NF1, NY-ESO-1, NY-BR-1, p190 minor BCR-abL, Pm1/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE and WT. Particularly preferred tumor antigens include CLAUDIN-18.2 (CLDN18.2) and CLAUDIN-6 (CLDN6).

It is been observed according to the invention that an efficient immune response can be elicited by immunization using PEI-formulated self-replicating (self-amplifying) RNA for delivering an antigen. PEI-formulated self-replicating RNA derived from Venezuelan equine encephalitis virus (VEEV) was particularly effective for delivering antigens which are membrane proteins.

According to the invention, the term "membrane protein" relates to proteins that are associated with or bound to a cellular membrane. They include integral membrane proteins that are permanently anchored or part of the membrane and peripheral membrane proteins that are only temporarily attached to the lipid bilayer or to other integral proteins. The integral membrane proteins are classified as transmembrane proteins that span across the membrane and integral monotopic proteins that are attached to only one side of the membrane. For example, membrane proteins can be classified into various general types:

1) Type I membrane proteins: These proteins have a single transmembrane domain in the mature protein. The N-terminus is extracellular, and the C-terminus is cytoplasmic. The N-terminal end of the proteins characteristically has a classic signal peptide sequence that directs the protein for import to the ER. The proteins are subdivided into Type Ia (containing a cleavable signal sequence) and Type Ib (without a cleavable signal sequence). Examples of Type I membrane proteins include, but are not limited to: Influenza HA, insulin receptor, glycophorin, LDL receptor, and viral G proteins.

2) Type II membrane proteins: For these single membrane domain proteins, the C-terminus is extracellular, and the N-terminus is cytoplasmic. The N-terminus can have a signal anchor sequence. Examples of this protein type include, but are not limited to: Influenza Neuraminidase, Golgi galactosyltransferase, Golgi sialyltransferase, Sucrase-isomaltase precursor, Asialoglycoprotein receptor, and Transferrin receptor.

3) Multipass transmembrane proteins: In Type I and II membrane proteins the polypeptide crosses the lipid bilayer once, whereas in multipass membrane proteins the polypeptide crosses the membrane multiple times. Multipass transmembrane proteins are also subdivided into Types IIIa and IIIb. Type IIIa proteins have cleavable signal sequences. Type IIIb proteins have their amino termini exposed on the exterior surface of the membrane, but do not have a cleavable signal sequence. Type IIIa proteins include, but are not limited to, the M and L peptides of the photoreaction center. Type IIIb proteins include, but are not limited to, cytochrome P450 and leader peptidase of $E.$ $coli$. Additional examples of multipass transmembrane proteins are membrane transporters, such as sugar transporters (glucose, xylose), and ion transporters.

4) Lipid chain anchored membrane proteins: These proteins are associated with the membrane bilayer by means of one or more covalently attached fatty acid chains or other types of lipid chains called prenyl groups.

5) GPI-anchored membrane proteins: These proteins are bound to the membrane by a glycosylphosphatidylinositol (GPI) anchor.

6) Peripheral membrane proteins: These proteins are bound to the membrane indirectly by noncovalent interactions with other membrane proteins.

The term "membrane protein" as used herein includes cellular membrane proteins of human or non-human cells as well as viral envelope proteins. An embodiment of a membrane protein is Influenza hemagglutinin (HA) which is a glycoprotein found on the surface of influenza viruses. It is responsible for binding the virus to cells with sialic acid on the membranes, such as cells in the upper respiratory tract or erythrocytes. It is also responsible for the fusion of the viral envelope with the endosome membrane, after the pH has been reduced. Other influenza virus membrane proteins are the M2 protein which is expressed abundantly at the cell surface, and neuraminidase (NA).

Accordingly, in one aspect, the invention relates to a pharmaceutical composition comprising:
 (a) single stranded, self-replicating RNA encoding a peptide or protein comprising an antigen or epitope; and
 (b) polyalkyleneimine.

In a further aspect, the invention relates to a composition comprising:
 (a) single stranded, self-replicating RNA encoding a peptide or protein comprising an antigen or epitope; and
 (b) polyalkyleneimine
 for use as a pharmaceutical.

In one embodiment of all aspects of the invention, the molar ratio of the number of nitrogen atoms (N) in the polyalkyleneimine to the number of phosphor atoms (P) in the single stranded RNA (N:P ratio) is 1.0 to 30, preferably 2.0 to 15.0, more preferably 6.0 to 12.0.

In a further aspect, the invention relates to a composition comprising:
 (a) single stranded, self-replicating RNA encoding a peptide or protein comprising an antigen or epitope; and
 (b) polyalkyleneimine
 wherein the molar ratio of the number of nitrogen atoms (N) in the polyalkyleneimine to the number of phosphor atoms (P) in the single stranded RNA (N:P ratio) is 1.0 to 30.0, preferably 2.0 to 15.0, more preferably 6.0 to 12.0.

In one embodiment of all aspects of the invention, the ionic strength of the composition is 50 mM or less, preferably wherein the concentration of positively charged monovalent ions is 25 mM or less and the concentration of free positively charged divalent cationic ions is 20 µM or less.

In a further aspect, the invention relates to a composition comprising:
(a) single stranded, self-replicating RNA encoding a peptide or protein comprising an antigen or epitope; and
(b) polyalkyleneimine
wherein the ionic strength is 50 mM or less.

In one embodiment, the concentration of positively charged monovalent ions is 25 mM or less and the concentration of positively charged divalent cationic ions is 20 µM or less.

In one embodiment of all aspects of the invention, the single stranded, self-replicating RNA is a cis-replicon.

In one embodiment, the single stranded, self-replicating RNA is derived from Venezuelan equine encephalitis virus (VEEV). In one embodiment, the single stranded, self-replicating RNA corresponds or corresponds essentially to the genomic RNA of VEEV or an attenuated form thereof, wherein the open reading frame encoding structural proteins is replaced by an open reading frame encoding the peptide or protein comprising an antigen or epitope. In one embodiment, the antigen or the peptide or protein comprising an antigen or epitope is a membrane protein such as a viral envelope protein. In one embodiment, the antigen is Influenza hemagglutinin.

In one embodiment, the single stranded, self-replicating RNA is derived from Semliki Forest virus (SFV). In one embodiment, the single stranded, self-replicating RNA corresponds or corresponds essentially to the genomic RNA of SFV or an attenuated form thereof, wherein the open reading frame encoding structural proteins is replaced by an open reading frame encoding the peptide or protein comprising an antigen or epitope. In one embodiment, the antigen or the peptide or protein comprising an antigen or epitope is not a membrane protein. In one embodiment, the antigen is a viral capsid protein.

In one embodiment of all aspects of the invention, the composition is for intramuscular administration such as by intramuscular injection.

In one embodiment of all aspects of the invention, the single stranded RNA and the polyalkyleneimine are present in polyplex particles.

In one embodiment of all aspects of the invention, the polyalkyleneimine comprises the following general formula (I):

$$-\!\!\left[\!\!\begin{array}{c}N-(CH_2)_n\\|\\R\end{array}\!\!\right]_p\!\!-,$$

wherein
R is H, an acyl group or a group comprising the following general formula (II):

$$-\!\!\left[\!\!\begin{array}{c}(CH_2)_m-N\\|\\R_1\end{array}\!\!\right]_q\!\!-,$$

wherein $R_1$ is H or a group comprising the following general formula (III):

$$-\!\!\left[(CH_2)_l-NH\right]_r\!\!-,$$

n, m, and l are independently selected from integers from 2 to 10; and
p, q, and r are integers, wherein the sum of p, q, and r is such that the average molecular weight of the polymer is $1.5 \cdot 10^2$ to $10^7$ Da, preferably 5000 to $10^5$ Da, more preferably 10000 to 40000 Da, more preferably 15000 to 30000 Da, even more preferably 20000 to 25000 Da.

In one embodiment, n, m, and l are independently selected from 2, 3, 4, and 5, preferably from 2 and 3. In one embodiment, $R_1$ is H. In one embodiment, R is H or an acyl group.

In one embodiment of all aspects of the invention, the polyalkyleneimine comprises polyethylenimine and/or polypropylenimine, preferably polyethyleneimine.

In one embodiment of all aspects of the invention, at least 92% of the N atoms in the polyalkyleneimine are protonatable.

In one embodiment of all aspects of the invention, the composition of the invention comprises one or more additives. In one embodiment, the one or more additives are selected from the group consisting of buffering substances, saccharides, stabilizers, cryoprotectants, lyoprotectants, and chelating agents. In one embodiment of all aspects of the invention, the composition of the invention comprises one or more polymers. In one embodiment, the buffering substances comprise at least one selected from the group consisting of 4-(2-hydroxyethyl)-1-piperazineethanesulfonic acid (HEPES), 2-(N-morpholino)ethanesulfonic acid (MES), 3-morpholino-2-hydroxypropanesulfonic acid (MOPSO), acetic acid buffering systems and analogues, phosphatic acid buffering systems, or citric acid buffering systems. In one embodiment of all aspects of the invention, the composition of the invention comprises buffers for buffering in the pH range between 4 and 6.5, between 3 and 5, or between 3.5 and 4.5. Examples for such buffer systems are acetate buffers or HEPES buffers or phosphate buffers or acetic acid buffers. In one embodiment, the saccharides comprise at least one selected from the group consisting of monosaccharides, disaccharides, trisaccharides, oligosaccharides, and polysachharides, preferably from glucose, trehalose, saccharose and dextran. In one embodiment, the additive is a dextran with a mean molar mass between 1 kDa and 100 kDa. In one embodiment, the cryoprotectants comprise at least one selected from the group consisting of glycols, such as ethylene glycol, propylene glycol, and glycerol. In one embodiment, the chelating agent comprises EDTA. In one embodiment, the composition of the invention comprises one or more block copolymers comprising ethylene oxide and propylene oxide building blocks. In one embodiment, the composition of the invention comprises copolymers comprising ethylene diamine groups. In one embodiment, the composition of the invention comprises an amphiphilic block copolymer, preferably comprising ethylene oxide and propylene oxide building blocks, optionally comprising also ethylene diamine groups.

In one embodiment of all aspects of the invention, the composition comprises HEPES buffered glucose (HBG or HBGx1), MES-buffered glucose (MBG or MBGx1), Acetate buffered glucose or HEPES buffered trehalose (HBT or HBTx1). In one embodiment of all aspects of the invention, the composition comprises glucose or trehalose or saccharose in an acetic acid buffer with a concentration in the range from 0.1 mM to 10 mM. In one embodiment of all aspects of the invention, the composition comprises glucose or trehalose or saccharose in a phosphate buffer with a concentration in the range from 0.1 mM to 10 mM.

In one embodiment of all aspects of the invention, the z-average size of the particles is less than 200 nm, preferably less than 150 nm and more preferably less than 100 nm. In one embodiment, the z-average size of the particles is between 50 nm and 200 nm. In one embodiment of all aspects of the invention, the Zeta-potential of the particles is 20 mV or more, preferably 25 to 40 mV. In one embodiment of all aspects of the invention, the electrophoretic mobility (p) of the particles is between 1 to 1.6 μm*cm/V*S. In one embodiment of all aspects of the invention, the z-average size of the particles and/or the Zeta-potential and/or the electrophoretic mobility are determined in a suspension comprising the polyplex particles and HEPES buffered glucose (HBG) or HEPES buffered trehalose (HBT). In one embodiment, the HBG comprises 5% glucose (w/v) and 10 mM HEPES, pH 7.1 or the HBT comprises 10% trehalose (w/v) and 10 mM HEPES, pH 7.1. In one embodiment, the z-average size of the particles is determined by dynamic light scattering and data analysis by cumulant algorithm. In one embodiment, the translation diffusion coefficient is measured by dynamic light scattering. Then, Stock-Einstein equation is used in order to calculate the Z-average. In one embodiment, the electrophoretic mobility is measured by laser-Doppler electrophoresis. Then, Henry equation or Smoluchowski equation is used in order to calculate the Zeta-potential.

In one embodiment, the MBG comprises 5% glucose (w/v) and 10 mM MES. In one embodiment, the Acetate buffered glucose comprises 5% glucose (w/v) and 10 mM acetate.

In one embodiment of all aspects of the invention, the particles are neutral or positively charged, preferably at physiological pH or at a pH between 4.5 and 7.5.

In one embodiment of all aspects of the invention, the single stranded RNA is a molecule of 6000 to 15000 bases, preferably 9000 to 12000 bases.

In one embodiment of all aspects of the invention, the composition described herein is for use in therapy. In one embodiment of all aspects of the invention, the composition described herein is a vaccine composition.

In a further aspect, the invention relates to a composition described herein for inducing an immune response. In one embodiment, the composition is administered by intramuscular administration. In one embodiment, the immune response is directed against the antigen or epitope.

In a further aspect, the invention relates to a method of inducing an immune response comprising the step of administering a composition described herein. In one embodiment, the composition is administered by intramuscular administration. In one embodiment, the immune response is directed against the antigen or epitope.

In some embodiments, it is not required that the pharmaceutically active peptide or protein is an antigen that elicits an immune response. Suitable pharmaceutically active proteins or peptides may be selected from the group consisting of cytokines and immune system proteins such as immunologically active compounds (e.g., interleukins, colony stimulating factor (CSF), granulocyte colony stimulating factor (G-CSF), granulocyte-macrophage colony stimulating factor (GM-CSF), erythropoietin, tumor necrosis factor (TNF), interferons, integrins, addressins, seletins, homing receptors, T cell receptors, immunoglobulins), hormones (insulin, thyroid hormone, catecholamines, gonadotrophines, trophic hormones, prolactin, oxytocin, dopamine, bovine somatotropin, leptins and the like), growth hormones (e.g., human grown hormone), growth factors (e.g., epidermal growth factor, nerve growth factor, insulin-like growth factor and the like), growth factor receptors, enzymes (tissue plasminogen activator, streptokinase, cholesterol biosynthetic or degradative, steriodogenic enzymes, kinases, phosphodiesterases, methylases, de-methylases, dehydrogenases, cellulases, proteases, lipases, phospholipases, aromatases, cytochromes, adenylate or guanylaste cyclases, neuramidases and the like), receptors (steroid hormone receptors, peptide receptors), binding proteins (growth hormone or growth factor binding proteins and the like), transcription and translation factors, tumor growth suppressing proteins (e.g., proteins which inhibit angiogenesis), structural proteins (such as collagen, fibroin, fibrinogen, elastin, tubulin, actin, and myosin), blood proteins (thrombin, serum albumin, Factor VII, Factor VIII, insulin, Factor IX, Factor X, tissue plasminogen activator, protein C, von Wilebrand factor, antithrombin III, glucocerebrosidase, erythropoietin granulocyte colony stimulating factor (GCSF) or modified Factor VIII, anticoagulants and the like. In one embodiment, the pharmaceutically active protein according to the invention is a cytokine which is involved in regulating lymphoid homeostasis, preferably a cytokine which is involved in and preferably induces or enhances development, priming, expansion, differentiation and/or survival of T cells. In one embodiment, the cytokine is an interleukin, e.g. IL-2, IL-7, IL-12, IL-15, or IL-21.

A further suitable protein of interest encoded by an open reading frame is an inhibitor of interferon (IFN) signaling. While it has been reported that viability of cells in which RNA has been introduced for expression can be reduced, in particular, if cells are transfected multiple times with RNA, IFN inhibiting agents were found to enhance the viability of cells in which RNA is to be expressed (WO 2014/071963 A1). Preferably, the inhibitor is an inhibitor of IFN type I signaling. Preventing engagement of IFN receptor by extracellular IFN and inhibiting intracellular IFN signaling in the cells allows stable expression of RNA in the cells. Alternatively or additionally, preventing engagement of IFN receptor by extracellular IFN and inhibiting intracellular IFN signaling enhances survival of the cells, in particular, if cells are transfected repetitively with RNA. Without wishing to be bound by theory, it is envisaged that intracellular IFN signalling can result in inhibition of translation and/or RNA degradation. This can be addressed by inhibiting one or more IFN-inducible antivirally active effector proteins. The IFN-inducible antivirally active effector protein can be selected from the group consisting of RNA-dependent protein kinase (PKR), 2',5'-oligoadenylate synthetase (OAS) and RNaseL. Inhibiting intracellular IFN signalling may comprise inhibiting the PKR-dependent pathway and/or the OAS-dependent pathway. A suitable protein of interest is a protein that is capable of inhibiting the PKR-dependent pathway and/or the OAS-dependent pathway. Inhibiting the PKR-dependent pathway may comprise inhibiting eIF2-alpha phosphorylation. Inhibiting PKR may comprise treating the cell with at least one PKR inhibitor. The PKR inhibitor may be a viral inhibitor of PKR. The preferred viral inhibitor of PKR is vaccinia virus E3. If a peptide or protein (e.g. E3, K3) is to inhibit intracellular IFN signaling, intracellular expression of the peptide or protein is preferred. Vaccinia virus E3 is a 25 kDa dsRNA-binding protein (encoded by gene E3L) that binds and sequesters dsRNA to prevent the activation of PKR and OAS. E3 can bind directly to PKR and inhibits its activity, resulting in reduced phosphorylation of eIF2-alpha. Other suitable inhibitors of IFN signaling are Herpes simplex virus ICP34.5, Toscana virus NSs, *Bombyx mori* nucleopolyhedrovirus PK2, and HCV NS34A.

In one embodiment, the inhibitor of intracellular or extracellular IFN signaling is encoded by a replicon. The replicon comprises nucleic acid sequence elements that allow replication by alphavirus replicase, typically CSE 1, CSE 2 and CSE 4; and preferably also nucleic acid sequence elements that allow production of a subgenomic transcript, i.e. a subgenomic promoter, typically comprising CSE 3. The replicon may additionally comprise one or more non-polypeptide-sequence modifying modifications as described herein, e.g. cap, poly(A) sequence, adaptation of the codon usage. If multiple open reading frames are present on the replicon, then an inhibitor of intracellular IFN signaling may be encoded by any one of them, optionally under control of a subgenomic promoter or not. In a preferred embodiment, the inhibitor of intracellular IFN signaling is encoded by the most upstream open reading frame of the RNA replicon. When an inhibitor of intracellular IFN signaling is encoded by the most upstream open reading frame of the RNA replicon, the genetic information encoding the inhibitor of intracellular IFN signaling will be translated early after introduction of the RNA replicon into a host cell, and the resulting protein may subsequently inhibit intracellular IFN signaling.

A further suitable protein of interest encoded by an open reading frame is functional alphavirus non-structural protein. The term "alphavirus non-structural protein" includes each and every co- or post-translationally modified form, including carbohydrate-modified (such as glycosylated) and lipid-modified forms of alphavirus non-structural protein.

In some embodiments, the term "alphavirus non-structural protein" refers to any one or more of individual non-structural proteins of alphavirus origin (nsP1, nsP2, nsP3, nsP4), or to a poly-protein comprising the polypeptide sequence of more than one non-structural protein of alphavirus origin. In some embodiments, "alphavirus non-structural protein" refers to nsP123 and/or to nsP4. In other embodiments, "alphavirus non-structural protein" refers to nsP1234. In one embodiment, the protein of interest encoded by an open reading frame consists of all of nsP1, nsP2, nsP3 and nsP4 as one single, optionally cleavable poly-protein: nsP1234. In one embodiment, the protein of interest encoded by an open reading frame consists of nsP1, nsP2 and nsP3 as one single, optionally cleavable polyprotein: nsP123. In that embodiment, nsP4 may be a further protein of interest and may be encoded by a further open reading frame.

In some embodiments, alphavirus non-structural protein is capable of forming a complex or association, e.g. in a host cell. In some embodiments, "alphavirus non-structural protein" refers to a complex or association of nsP123 (synonymously P123) and nsP4. In some embodiments, "alphavirus non-structural protein" refers to a complex or association of nsP1, nsP2, and nsP3. In some embodiments, "alphavirus non-structural protein" refers to a complex or association of nsP1, nsP2, nsP3 and nsP4. In some embodiments, "alphavirus non-structural protein" refers to a complex or association of any one or more selected from the group consisting of nsP1, nsP2, nsP3 and nsP4. In some embodiments, the alphavirus non-structural protein comprises at least nsP4.

The terms "complex" or "association" refer to two or more same or different protein molecules that are in spatial proximity. Proteins of a complex are preferably in direct or indirect physical or physicochemical contact with each other. A complex or association can consist of multiple different proteins (heteromultimer) and/or of multiple copies of one particular protein (homomultimer). In the context of alphavirus non-structural protein, the term "complex or association" describes a multitude of at least two protein molecules, of which at least one is an alphavirus non-structural protein. The complex or association can consist of multiple copies of one particular protein (homomultimer) and/or of multiple different proteins (heteromultimer). In the context of a multimer, "multi" means more than one, such as two, three, four, five, six, seven, eight, nine, ten, or more than ten.

The term "functional alphavirus non-structural protein" includes alphavirus non-structural protein that has replicase function. Thus, "functional alphavirus non-structural protein" includes alphavirus replicase. "Replicase function" comprises the function of an RNA-dependent RNA polymerase (RdRP), i.e. an enzyme which is capable to catalyze the synthesis of (−) strand RNA based on a (+) strand RNA template, and/or which is capable to catalyze the synthesis of (+) strand RNA based on a (−) strand RNA template. Thus, the term "functional alphavirus non-structural protein" can refer to a protein or complex that synthesizes (−) stranded RNA, using the (+) stranded (e.g. genomic) RNA as template, to a protein or complex that synthesizes new (+) stranded RNA, using the (−) stranded complement of genomic RNA as template, and/or to a protein or complex that synthesizes a subgenomic transcript, using a fragment of the (−) stranded complement of genomic RNA as template. The functional alphavirus non-structural protein may additionally have one or more additional functions, such as e.g. a protease (for auto-cleavage), helicase, terminal adenylyltransferase (for poly(A) tail addition), methyltransferase and guanylyltransferase (for providing a nucleic acid with a 5'-cap), nuclear localization sites, triphosphatase (Gould et al., 2010, Antiviral Res., vol. 87 pp. 111-124; Rupp et al., 2015, J. Gen. Virol., vol. 96, pp. 2483-500).

According to the invention, the term "alphavirus replicase" refers to alphaviral RNA-dependent RNA polymerase, including a RNA-dependent RNA polymerase from a naturally occurring alphavirus (alphavirus found in nature) and a RNA-dependent RNA polymerase from a variant or derivative of an alphavirus, such as from an attenuated alphavirus. In the context of the present invention, the terms "replicase" and "alphavirus replicase" are used interchangeably, unless the context dictates that any particular replicase is not an alphavirus replicase.

The term "replicase" comprises all variants, in particular post-translationally modified variants, conformations, isoforms and homologs of alphavirus replicase, which are expressed by alphavirus-infected cells or which are expressed by cells that have been transfected with a nucleic acid that codes for alphavirus replicase. Moreover, the term "replicase" comprises all forms of replicase that have been produced and can be produced by recombinant methods. For example, a replicase comprising a tag that facilitates detection and/or purification of the replicase in the laboratory, e.g. a myc-tag, a HA-tag or an oligohistidine tag (His-tag) may be produced by recombinant methods.

Optionally, the alphavirus replicase is additionally functionally defined by the capacity of binding to any one or more of alphavirus conserved sequence element 1 (CSE 1) or complementary sequence thereof, conserved sequence element 2 (CSE 2) or complementary sequence thereof, conserved sequence element 3 (CSE 3) or complementary sequence thereof, conserved sequence element 4 (CSE 4) or complementary sequence thereof. Preferably, the replicase is capable of binding to CSE 2 [i.e. to the (+) strand] and/or to CSE 4 [i.e. to the (+) strand], or of binding to the complement of CSE 1 [i.e. to the (−) strand] and/or to the complement of CSE 3 [i.e. to the (−) strand].

The origin of the replicase is not limited to any particular alphavirus. In a preferred embodiment, the alphavirus replicase comprises non-structural protein from Semliki Forest virus, including a naturally occurring Semliki Forest virus and a variant or derivative of Semliki Forest virus, such as an attenuated Semliki Forest virus. In an alternative preferred embodiment, the alphavirus replicase comprises non-structural protein from Sindbis virus, including a naturally occurring Sindbis virus and a variant or derivative of Sindbis virus, such as an attenuated Sindbis virus. In an alternative preferred embodiment, the alphavirus replicase comprises non-structural protein from Venezuelan equine encephalitis virus (VEEV), including a naturally occurring VEEV and a variant or derivative of VEEV, such as an attenuated VEEV. In an alternative preferred embodiment, the alphavirus replicase comprises non-structural protein from chikungunya virus (CHIKV), including a naturally occurring CHIKV and a variant or derivative of CHIKV, such as an attenuated CHIKV.

A replicase can also comprise non-structural proteins from more than one alphavirus. Thus, heterologous complexes or associations comprising alphavirus non-structural protein and having replicase function are equally comprised by the present invention. Merely for illustrative purposes, replicase may comprise one or more non-structural proteins (e.g. nsP1, nsP2) from a first alphavirus, and one or more non-structural proteins (nsP3, nsP4) from a second alphavirus. Non-structural proteins from more than one different alphavirus may be encoded by separate open reading frames, or may be encoded by a single open reading frame as poly-protein, e.g. nsP1234.

In some embodiments, functional alphavirus non-structural protein is capable of forming membranous replication complexes and/or vacuoles in cells in which the functional alphavirus non-structural protein is expressed.

If functional alphavirus non-structural protein, i.e. alphavirus non-structural protein with replicase function, is encoded by a nucleic acid molecule according to the present invention, it is preferable that the subgenomic promoter of the replicon, if present, is compatible with said replicase. Compatible in this context means that the alphavirus replicase is capable of recognizing the subgenomic promoter, if present. In one embodiment, this is achieved when the subgenomic promoter is native to the alphavirus from which the replicase is derived, i.e. the natural origin of these sequences is the same alphavirus. In an alternative embodiment, the subgenomic promoter is not native to the alphavirus from which the alphavirus replicase is derived, provided that the alphavirus replicase is capable of recognizing the subgenomic promoter. In other words, the replicase is compatible with the subgenomic promoter (cross-virus compatibility). Examples of cross-virus compatibility concerning subgenomic promoter and replicase originating from different alphaviruses are known in the art. Any combination of subgenomic promoter and replicase is possible as long as cross-virus compatibility exists. Cross-virus compatibility can readily be tested by the skilled person working the present invention by incubating a replicase to be tested together with an RNA, wherein the RNA has a subgenomic promoter to be tested, at conditions suitable for RNA synthesis from the a subgenomic promoter. If a subgenomic transcript is prepared, the subgenomic promoter and the replicase are determined to be compatible. Various examples of cross-virus compatibility are known (reviewed by Strauss & Strauss, Microbiol. Rev., 1994, vol. 58, pp. 491-562).

In the present invention, an open reading frame encoding functional alphavirus non-structural protein can be provided on the RNA replicon, or alternatively, can be provided as separate nucleic acid molecule, e.g. mRNA molecule. A separate mRNA molecule may optionally comprise e.g. cap, 5'-UTR, 3'-UTR, poly(A) sequence, and/or adaptation of the codon usage. The separate mRNA molecule may be provided in trans, as described herein.

When an open reading frame encoding functional alphavirus non-structural protein is provided on the RNA replicon, the replicon can preferably be replicated by the functional alphavirus non-structural protein. In particular, the RNA replicon that encodes functional alphavirus non-structural protein can be replicated by the functional alphavirus non-structural protein encoded by the replicon. This embodiment is strongly preferred when no nucleic acid molecule encoding functional alphavirus non-structural protein is provided in trans. In this embodiment, cis-replication of the replicon is aimed at. In a preferred embodiment, the RNA replicon comprises an open reading frame encoding functional alphavirus non-structural protein as well as at least one further open reading frame encoding a protein of interest, and can be replicated by the functional alphavirus non-structural protein.

If multiple open reading frames are present on the replicon, then the functional alphavirus non-structural protein may be encoded by any one of them, optionally under control of a subgenomic promoter or not, preferably not under control of a subgenomic promoter. In a preferred embodiment, the functional alphavirus non-structural protein is encoded by the most upstream open reading frame of the RNA replicon. When the functional alphavirus non-structural protein is encoded by the most upstream open reading frame of the RNA replicon, the genetic information encoding functional alphavirus non-structural protein will be translated early after introduction of the RNA replicon into a host cell, and the resulting protein can subsequently drive replication, and optionally production of a subgenomic transcript, in the host cell.

Presence of an open reading frame encoding functional alphavirus non-structural protein, either comprised by the replicon or comprised by a separate nucleic acid molecule that is provided in trans, allows that the replicon is replicated, and consequently, that a gene of interest encoded by the replicon, optionally under control of a subgenomic promoter, is expressed at high levels.

The RNA replicon is suitable for expression of one or more genes encoding a peptide of interest or a protein of interest, optionally under control of a subgenomic promoter. Various embodiments are possible. One or more open reading frames, each encoding a peptide of interest or a protein of interest, can be present on the RNA replicon. The most upstream open reading frame of the RNA replicon is referred to as "first open reading frame". In some embodiments, the "first open reading frame" is the only open reading frame of the RNA replicon. Optionally, one or more further open reading frames can be present downstream of the first open reading frame. One or more further open reading frames downstream of the first open reading frame may be referred to as "second open reading frame", "third open reading frame" and so on, in the order (5' to 3') in which they are present downstream of the first open reading frame. Preferably, each open reading frame comprises a start codon (base triplet), typically AUG (in the RNA molecule), corresponding to ATG (in a respective DNA molecule).

If the replicon comprises a 3' replication recognition sequence, it is preferred that all open reading frames are localized upstream of the 3' replication recognition sequence.

When the RNA replicon comprising one or more open reading frames is introduced into a host cell, the replicon may serve directly as template for translation of the first open reading frame. Preferably, the replicon comprises a 5'-cap. This is helpful for expression of the gene encoded by the first open reading frame directly from the replicon.

In some embodiments, at least one open reading frame of the replicon is under the control of a subgenomic promoter, preferably an alphavirus subgenomic promoter. The alphavirus subgenomic promoter is very efficient, and is therefore suitable for heterologous gene expression at high levels. Preferably, the subgenomic promoter is a promoter for a subgenomic transcript in an alphavirus. This means that the subgenomic promoter is one which is native to an alphavirus and which preferably controls transcription of the open reading frame encoding one or more structural proteins in said alphavirus. Alternatively, the subgenomic promoter is a variant of a subgenomic promoter of an alphavirus; any variant which functions as promoter for subgenomic RNA transcription in a host cell is suitable. If the replicon comprises a subgenomic promoter, it is preferred that the replicon comprises a conserved sequence element 3 (CSE 3) or a variant thereof.

Preferably, the at least one open reading frame under control of a subgenomic promoter is localized downstream of the subgenomic promoter. Preferably, the subgenomic promoter controls production of subgenomic RNA comprising a transcript of the open reading frame.

In some embodiments the first open reading frame is under control of a subgenomic promoter. When the first open reading frame is under control of a subgenomic promoter, its localization resembles the localization of the open reading frame encoding structural proteins in the genome of an alphavirus. When the first open reading frame is under control of the subgenomic promoter, it is preferred that the gene encoded by the first open reading frame can be expressed both from the replicon as well as from a subgenomic transcript thereof (the latter in the presence of functional alphavirus non-structural protein). One or more further open reading frames, each under control of a subgenomic promoter, may be present downstream of the first open reading frame that is under control of a subgenomic promoter. The genes encoded by the one or more further open reading frames, e.g. by the second open reading frame, may be translated from one or more subgenomic transcripts, each under control of a subgenomic promoter. For example, the RNA replicon may comprise a subgenomic promoter controlling production of a transcript that encodes a second protein of interest.

In other embodiments the first open reading frame is not under control of a subgenomic promoter. When the first open reading frame is not under control of a subgenomic promoter, the gene encoded by the first open reading frame can be expressed from the replicon. One or more further open reading frames, each under control of a subgenomic promoter, may be present downstream of the first open reading frame. The genes encoded by the one or more further open reading frames may be expressed from subgenomic transcripts.

In a cell which comprises the replicon according to the present invention, the replicon may be amplified by functional alphavirus non-structural protein. Additionally, if the replicon comprises one or more open reading frames under control of a subgenomic promoter, one or more subgenomic transcripts are expected to be prepared by functional alphavirus non-structural protein. Functional alphavirus non-structural protein may be provided in trans, or may be encoded by an open reading frame of the replicon.

If a replicon comprises more than one open reading frame encoding a protein of interest, it is preferable that each open reading frame encodes a different protein, e.g. a different pharmaceutically active peptide or protein. For example, the protein encoded by the second open reading frame is different from the protein encoded by the first open reading frame.

In some embodiments, the protein of interest encoded by the first and/or a further open reading frame, preferably by the first open reading frame, is functional alphavirus non-structural protein or an inhibitor of IFN signaling, e.g. E3. In some embodiments, the protein of interest encoded by the first and/or a further open reading frame, e.g. by the second open reading frame, is a pharmaceutically active peptide or protein, or a reporter protein.

In one embodiment, the protein of interest encoded by the first open reading frame is functional alphavirus non-structural protein. In that embodiment the replicon preferably comprises a 5'-cap. Particularly when the protein of interest encoded by the first open reading frame is functional alphavirus non-structural protein, and preferably when the replicon comprises a 5'-cap, the nucleic acid sequence encoding functional alphavirus non-structural protein can be efficiently translated from the replicon, and the resulting protein can subsequently drive replication of the replicon and drive synthesis of subgenomic transcript(s). This embodiment may be preferred when no additional nucleic acid molecule encoding functional alphavirus non-structural protein is used or present together with the replicon. In this embodiment, cis-replication of the replicon is aimed at.

The compositions described herein may be administered for treating diseases such as those described herein, e.g. a disease associated with an antigen encoded by the RNA which is administered.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality.

The term "disease associated with an antigen" or "disease involving an antigen" refers to any disease which implicates an antigen, e.g. a disease which is characterized by the presence of an antigen. The disease involving an antigen can be an infectious disease, an autoimmune disease, or a cancer disease or simply cancer. As mentioned above, the antigen may be a disease-associated antigen, such as a tumor-associated antigen, a viral antigen, or a bacterial antigen.

The term "infectious disease" refers to any disease which can be transmitted from individual to individual or from organism to organism, and is caused by a microbial agent (e.g. common cold). Infectious diseases are known in the art and include, for example, a viral disease, a bacterial disease, or a parasitic disease, which diseases are caused by a virus, a bacterium, and a parasite, respectively. In this regard, the infectious disease can be, for example, hepatitis, sexually transmitted diseases (e.g. chlamydia or gonorrhea), tuberculosis, HIV/acquired immune deficiency syndrome (AIDS), diphtheria, hepatitis B, hepatitis C, cholera, severe acute respiratory syndrome (SARS), the bird flu, influenza, animal diseases like foot-and-mouth disease, Peste de petits ruminants, Porcine reproductive and respiratory syndrome virus or parasite diseases such as Chagas, Malaria and others.

The term "autoimmune disease" refers to any disease in which the body produces an immunogenic (i.e. immune system) response to some constituent of its own tissue. In other words, the immune system loses its ability to recognize some tissue or system within the body as self and targets and attacks it as if it were foreign. Autoimmune diseases can be classified into those in which predominantly one organ is affected (e.g. hemolytic anemia and anti-immune thyroiditis), and those in which the autoimmune disease process is diffused through many tissues (e.g. systemic lupus erythematosus). For example, multiple sclerosis is thought to be caused by T cells attacking the sheaths that surround the nerve fibers of the brain and spinal cord. This results in loss of coordination, weakness, and blurred vision. Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

The terms "cancer disease" or "cancer" refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the invention also comprises cancer metastases.

The term "immune response" relates to a reaction of the immune system such as to immunogenic organisms, such as bacteria or viruses, cells or substances. The term "immune response" includes the innate immune response and the adaptive immune response. Preferably, the immune response is related to an activation of immune cells, an induction of cytokine biosynthesis and/or antibody production.

It is preferred that the immune response induced by the compositions of the present invention comprises the steps of activation of antigen presenting cells, such as dendritic cells and/or macrophages, presentation of an antigen or fragment thereof by said antigen presenting cells and activation of cytotoxic T cells due to this presentation.

The term "immune cells" refers to cells of the immune system involved in defending the body of an individual. The term "immune cells" encompasses specific types of immune cells and their precursors including leucocytes comprising macrophages, monocytes (precursors of macrophages), granulocytes such as neutrophils, eosinophils and basophils, dendritic cells, mast cells, and lymphocytes such as B cells, T cells and natural killer (NK) cells. Macrophages, monocytes (precursors of macrophages), neutrophils, dendritic cells, and mast cells are phagocytic cells.

The term "immunotherapy" relates to the treatment of a disease or condition by inducing, enhancing, or suppressing an immune response. Immunotherapies designed to elicit or amplify an immune response are classified as activation immunotherapies, while immunotherapies that reduce or suppress an immune response are classified as suppression immunotherapies. The term "immunotherapy" includes antigen immunization or antigen vaccination, or tumor immunization or tumor vaccination. The term "immunotherapy" also relates to the manipulation of immune responses such that inappropriate immune responses are modulated into more appropriate ones in the context of autoimmune diseases such as rheumatic arthritis, allergies, diabetes or multiple sclerosis.

The terms "immunization" or "vaccination" describe the process of administering an antigen to an individual with the purpose of inducing an immune response, for example, for therapeutic or prophylactic reasons.

The term "therapeutic treatment" or simply "treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The term "prophylactic treatment" or "preventive treatment" relates to any treatment that is intended to prevent a disease from occurring in an individual. The terms "prophylactic treatment" or "preventive treatment" are used herein interchangeably.

The terms "protect", "prevent", "prophylactic", "preventive", or "protective" relate to the prevention and/or treatment of the occurrence and/or the propagation of a disease, e.g. tumor, in an individual. For example, a prophylactic administration of an immunotherapy, e.g. by administering the composition of the present invention, can protect the receiving individual from the development of a tumor. For example, a therapeutic administration of an immunotherapy, e.g. by administering the composition of the present invention, can stop the development of a disease, e.g. lead to the inhibition of the progress/growth of a tumor. This comprises the deceleration of the progress/growth of the tumor, in particular a disruption of the progression of the tumor, which preferably leads to elimination of the tumor. A therapeutic administration of an immunotherapy may protect the individual, for example, from the dissemination or metastasis of existing tumors.

The term "individual" or "subject" relates to vertebrates, particularly mammals. For example, mammals in the context of the present invention are humans, non-human primates, domesticated mammals such as dogs, cats, sheep, cattle, goats, pigs, horses etc., laboratory animals such as mice, rats, rabbits, guinea pigs, etc. as well as animals in captivity such as animals of zoos. The term "subject" also relates to non-mammalian vertebrates such as birds (particularly domesticated birds such as chicken, ducks, geese, turkeys) and to fish (particularly farmed fish, e.g. salmon or catfish). The term "animal" as used herein also includes humans.

The agents such as polyplex particles described herein may be administered in the form of any suitable pharmaceutical composition. The term "pharmaceutical composition" relates to a formulation comprising a therapeutically effective agent or a salt thereof, preferably together with pharmaceutical excipients such as buffers, preservatives and tonicity modifiers. Said pharmaceutical composition is useful for treating, preventing, or reducing the severity of a disease or disorder by administration of said pharmaceutical composition to an individual. A pharmaceutical composition is also known in the art as a pharmaceutical formulation. The pharmaceutical composition can be administered locally or systemically. In the context of the present invention, the pharmaceutical composition comprises the particles described herein.

The term "systemic administration" refers to the administration of a therapeutically effective agent such that the agent becomes widely distributed in the body of an individual in significant amounts and develops a biological effect. According to the present invention, it is preferred that administration is by parenteral administration.

The term "parenteral administration" refers to administration of a therapeutically effective agent such that the agent does not pass the intestine. The term "parenteral administration" includes intravenous administration, subcutaneous administration, intradermal administration or intraarterial administration but is not limited thereto.

In one particularly preferred embodiment, the composition according to the present invention is administered to muscle tissue, such as skeletal muscle. Intramuscular administration such as by intramuscular injection thus is the preferred route of administration.

Administration can be achieved in various ways. In one embodiment, the composition according to the present invention is administered by injection. In a preferred embodiment, injection is via a needle. Needle-free injection may be used as an alternative.

The pharmaceutical compositions of the present invention may comprise at least one adjuvant. The term "adjuvant" relates to compounds, which when administered in combination with an antigen or antigen peptide to an individual, prolong or enhance or accelerate an immune response. It is assumed that adjuvants exert their biological activity by one or more mechanisms, including an increase of the surface of the antigen, a prolongation of the retention of the antigen in the body, a retardation of the antigen release, targeting of the antigen to macrophages, increase of the uptake of the antigen, enhancement of antigen processing, stimulation of cytokine release, stimulation and activation of immune cells such as B cells, macrophages, dendritic cells, T cells and unspecific activation of immune cells. Adjuvants comprise a heterogeneous group of compounds such as oil emulsions (e.g., Freund's adjuvants), mineral compounds (such as alum), bacterial products (such as Bordetella pertussis toxin), or immune-stimulating complexes. Examples for adjuvants include saponins, incomplete Freund's adjuvants, complete Freund's adjuvants, tocopherol or alum, but are not limited thereto.

The pharmaceutical composition according to the present invention is generally applied in a "pharmaceutically effective amount" and in "a pharmaceutically acceptable preparation".

The term "pharmaceutically effective amount" refers to the amount which achieves a desired reaction or a desired effect alone or together with further doses. In the case of the treatment of a particular disease, the desired reaction preferably relates to inhibition of the course of the disease. This comprises slowing down the progress of the disease and, in particular, interrupting or reversing the progress of the disease. The desired reaction in a treatment of a disease may also be delay of the onset or a prevention of the onset of said disease or said condition. An effective amount of the compositions described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the compositions described herein may depend on various of such parameters. In the case that a reaction in a patient is insufficient with an initial dose, higher doses (or effectively higher doses achieved by a different, more localized route of administration) may be used.

The term "pharmaceutically acceptable" refers to the non-toxicity of a material which does not interact with the action of the active component of the pharmaceutical composition.

The pharmaceutical compositions of the present invention may contain salts, buffers, preserving agents, carriers and optionally other therapeutic agents. Preferably, the pharmaceutical compositions of the present invention comprise one or more pharmaceutically acceptable carriers, diluents and/or excipients.

The term "excipient" is intended to indicate all substances in a pharmaceutical composition which are not active ingredients such as binders, lubricants, thickeners, surface active agents, preservatives, emulsifiers, buffers, flavoring agents, or colorants.

The term "diluent" relates a diluting and/or thinning agent. Moreover, the term "diluent" includes any one or more of fluid, liquid or solid suspension and/or mixing media.

The term "carrier" relates to one or more compatible solid or liquid fillers or diluents, which are suitable for an administration to a human. The term "carrier" relates to a natural or synthetic organic or inorganic component which is combined with an active component in order to facilitate the application of the active component. Preferably, carrier components are sterile liquids such as water or oils, including those which are derived from mineral oil, animals, or plants, such as peanut oil, soy bean oil, sesame oil, sunflower oil, etc. Salt solutions and aqueous dextrose and glycerin solutions may also be used as aqueous carrier compounds.

Pharmaceutically acceptable carriers or diluents for therapeutic use are well known in the pharmaceutical art, and are described, for example, in Remington's Pharmaceutical Sciences, Mack Publishing Co. (A. R Gennaro edit. 1985). Examples of suitable carriers include, for example, magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Examples of suitable diluents include ethanol, glycerol and water.

Pharmaceutical carriers, excipients or diluents can be selected with regard to the intended route of administration and standard pharmaceutical practice. The pharmaceutical compositions of the present invention may comprise as, or in addition to, the carrier(s), excipient(s) or diluent(s) any suitable binder(s), lubricant(s), suspending agent(s), coating agent(s), and/or solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

In one embodiment, the composition is an aqueous composition. The aqueous composition may optionally comprise solutes, e.g. salts. In one embodiment, the composition is in the form of a freeze-dried composition. A freeze-dried composition is obtainable by freeze-drying a respective aqueous composition.

The agents and compositions provided herein may be used alone or in combination with other therapeutic regimens such as surgery, irradiation, chemotherapy and/or bone marrow transplantation (autologous, syngeneic, allogeneic or unrelated).

The present invention is described in detail and is illustrated by the figures and examples, which are used only for illustration purposes and are not meant to be limiting. Owing to the description and the examples, further embodiments which are likewise included in the invention are accessible to the skilled worker.

EXAMPLES

Example 1: In-Vitro Toxicity of Polyplexes

Materials and Methods

In vivo-jetPEI™ Reagent, Cat. #201-50G, was purchased from Polyplus-Transfection (Illkirch, France). In vivo-jetPEI™ is provided at 150 mM (expressed as the concentration of nitrogen residues) in sterile apyrogenic water. JetPEI was diluted in HEPES 10 mM, pH 7.1, glucose 5% (HBGx1) buffer to the desired concentrations (expressed as the concentration of nitrogen residues).

In-Vitro Cytotoxicity Assay

HEK-293 cells were seeded in a 96-well plate (flat bottom) at concentration of $2\times10^4$ cells per well. The cells were maintained at 37° C. and 7.5% CO2. After 24 h, the supernatant was discarded and replaced with 50 µL of DMEM Medium (+10% FCS). PEI was diluted (1:5) in RPMI medium with 10% FCS and pre-incubated for ~15 min. Then 50 µl of the PEI solution was added to the cells to a final medium volume of 100 µl. After additional 18 h, XTT-Assay (XTT Cell Viability Kit #9095, New England Biolabs GmbH, Frankfurt, Germany) was performed according to the manual instructions. The cell death data as a function of PEI concentration was fitted using the sigmoidal equation:

$$\text{Cell death \%} = \text{bottom} + \frac{\text{Top} - \text{Bottom}}{1 + 10^{(\log IC_{50} - \log Concentration) \times (Hill\ slope)}}$$

Figure 1:
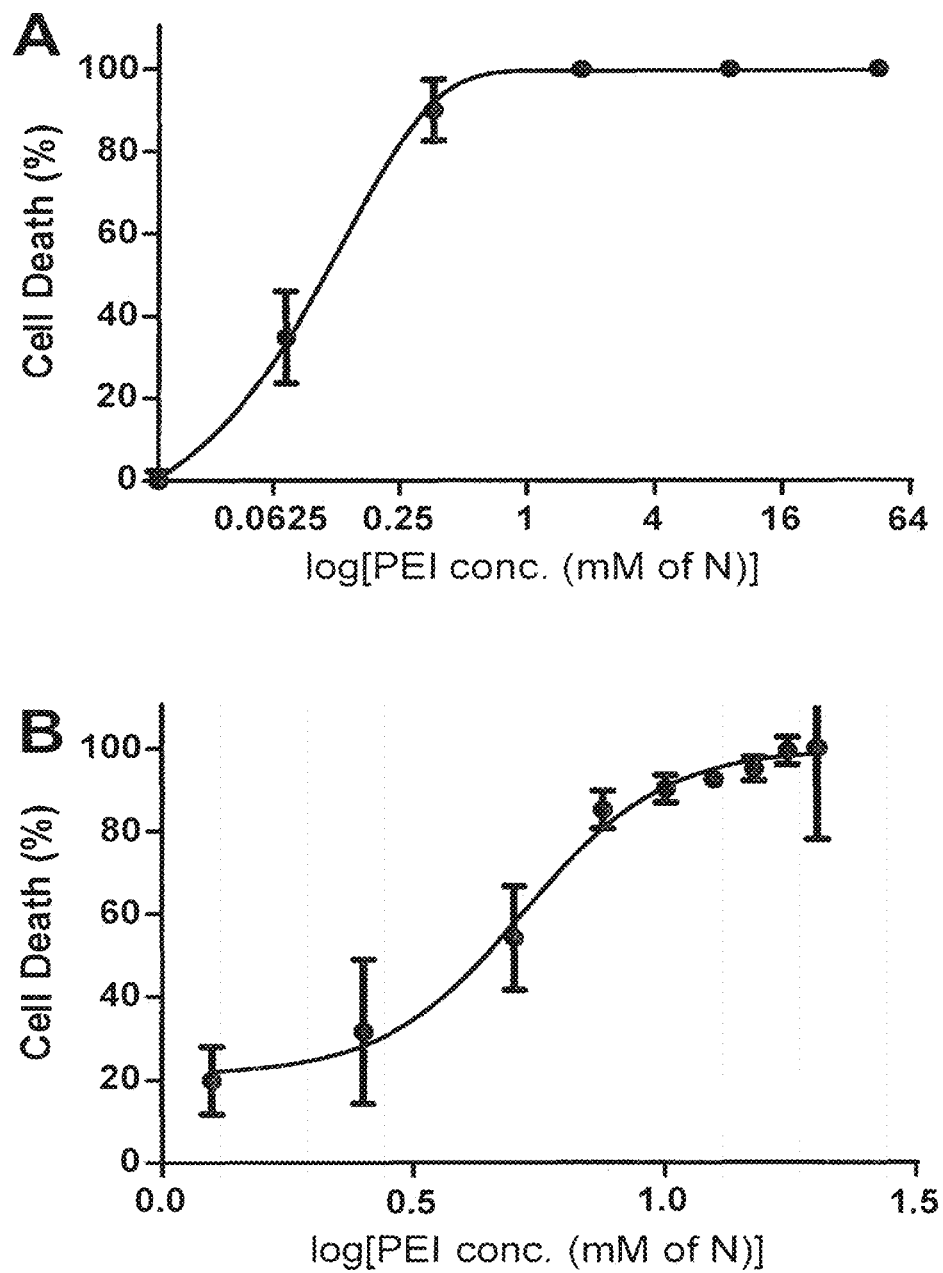
FIG. 1. A. Toxicity of free pure PEI on HEK-293 cells in-vitro. $IC_{50}$=77 µM of nitrogens (free). B. Toxicity of PEI/Replicon-RNA polyplexes on HEK-293 cells in-vitro. $IC_{50}$=542 µM of nitrogens (polyplex formulation).
Figure 1:
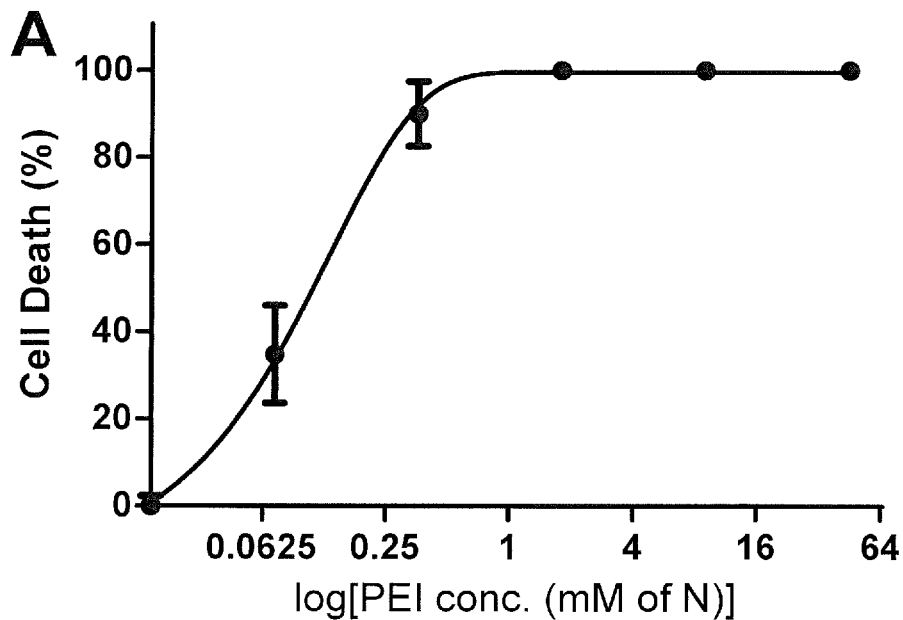
Figure 1:
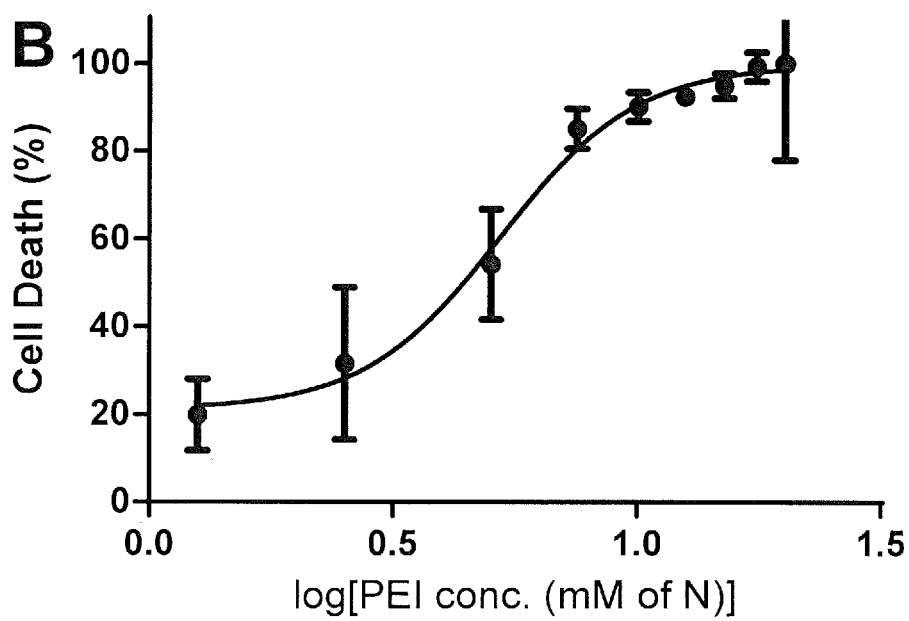

FIG. 1A shows the toxicity of free pure PEI on HEK-293 cells in-vitro. $IC_{50}=77$ µM of nitrogens (free). FIG. 1B shows the toxicity of PEI/Replicon-RNA polyplexes on HEK-293 cells in-vitro. $IC_{50}=542$ µM of nitrogens (polyplex formulation).

Results and Conclusions

Free PEI leads to cell death at nitrogen concentration above 18 µM (FIG. 1A). The final concentration of free PEI in the cell medium should be below the aforementioned limit in order to avoid toxicity problems.

Polyplexes cause less cell death than free PEI but their toxicity also increase when the PEI concentration increases (FIG. 1B). The cell death after addition of polyplexes could be calculated using the equation:

$$\text{Cell death \%} = 21.13 + 78.59/(1 + 10^{((-0.27 - \log(Concentration)) \times 3.13)})$$

For polyplexes of N/P 11.6 (RNA concentration of 10 mg/l, PEI=348 µM), the cell death is 36.8%, while for polyplexes of N/P 15.8 the cell death is 52.3%.

Example 2: Stability Studies of Polyplexes

Materials and Methods

In vivo-jetPEI™ Reagent from example 1 was used. RNA that encodes for luciferase, Construct D1-824 Replicon, ID R076 1, was provided by RNA Biochemistry unit (BioNTech RNA Pharmaceuticals GmbH, Mainz, Germany).

Preparation of Polyplexes

Prior to preparation, in-vivo jetPEI™ and the sugar solution were equilibrated at room temperature. The preparation of the in vivo-jetPEI™/RNA complexes was performed in a laminar flow hood using a sterile sugar solutions (Table 1). The final concentration of the sugar in the formulation was 5-10% w/v.

All formulations were prepared at RNA concentration of 250 mg/l and NIP ratio of 11.6.

The preparation steps were:
1. The RNA was diluted using a concentrated sugar buffer (HBGx2, MBGx2 or HBTx2) to prepare a solution of ½ the final volume. Gentle vortex was applied.
2. The in-vivo jetPEI™ reagent was diluted using the same sugar buffer and sterile water to prepare a solution of ⅗ the final volume. Gentle vortex was applied.
3. Half of the volume from the diluted in-vivo jetPEI™ was added rapidly to the diluted RNA all at once, and gentle vortex was applied.
4. The polyplexes were incubated for 15 to 20 minutes at room temperature, and then transferred to the appropriate storage condition.

TABLE 1

Mediums for preparation and storage of polyplexes

| # | Medium | Abbreviation |
|---|--------|--------------|
| 1 | Glucose 5% with HEPES 10 mM, pH 7.1 | HBG × 1 |
| 2 | Trehalose 10% with HEPES 10 mM, pH 7.1 | HBT × 1 |
| 3 | Trehalose 10% with HEPES 2.8 mM and EDTA 80 µM, pH 7.1 | HBT × 1 + EDTA |
| 4 | Glucose 10% with HEPES 20 mM, pH 7.1 | HBG × 2 |
| 5 | Trehalose 20% with HEPES 20 mM, pH 7.1 | HBT × 2 |

Lyophilization of Polyplexes

The formulations were placed in a benchtop manifold freeze-drier Epsilon 2-4 LSCplus (Martin Christ Gefriertrocknungsanlagen GmbH, Osterode, Germany).

The samples were frozen to −40° C. (~2° C./min) at 1 ATM. It took 60-90 min.

The pressure was reduced to 0.2 ATM for 10 min at −40° C.

The samples were dried for 4 h at 0.2 ATM and −40° C.

The samples were heated to −16° C. at 0.2 ATM for 2 h (ramp).

The samples were continued to dry for 4 h at −16° C. & 0.2 ATM.

The pressure was reduced to 0.01 ATM for 10 min at −16° C.

The samples were continued to dry for 4 h at −16° C. & 0.01 ATM.

The samples were heated to 20° C. at 0.01 ATM for 2 h (ramp).

The samples were continued to dry for 8 h at 20° C. & 0.01 ATM.

RNA Release from Polyplexes

Twelve test tubes with 90 µl sample were prepared according to Table 2.

TABLE 2

Sample preparation for RNA integrity and concentration measurements

| # | Description |
|---|---|
| 1 | Polyplexes in HBG stored at RT |
| 2 | Polyplexes in HBG stored at 4° C. |
| 3 | Polyplexes in HBG stored at −20° C. |
| 4 | Polyplexes in HBT stored at RT |
| 5 | Polyplexes in HBT stored at 4° C. |
| 6 | Polyplexes in HBT stored at −20° C. |
| 7 | Lyophilized Polyplexes in HBT stored at 4° C. |
| 8 | Free RNA 250 mg/l in HBG × 1 |
| 9 | Free RNA 125 mg/l in HBG × 1 |
| 10 | Free RNA 63 mg/l in HBG × 1 |
| 11 | Free RNA 31 mg/l in HBG × 1 |
| 12 | HBG × 1 |

Ten µl of Heparin 50 g/l in NaCl 500 mM were added to each tube. The mixture was incubated for 20 min at 30° C. in a vortex machine with shaking speed of 300 rpm.

RNA Integrity

Five µl of the released RNA were used for Bioanalyzer measurement. The RNA was mixed with 5 µl of formamide. The RNA integrity quantification was performed with the Agilent 2100 Bioanalyzer instrument. Agilent RNA 6000 Nano Kit was equilibrated at room temperature for 30 minutes. "Nano Gel Matrix" 400 µl was centrifuged at 1500 g for 10 minutes. Sixty five µL of the supernatant were mixed with 1 µL of well vortexed "Nano Dye Concentrate" and centrifuged at 15000 g for 10 minutes to obtain the "Gel-Dye-Mix". The prepared samples were denaturated by heating for 10 minutes at 70° C., and the "Nano Ladder" was also heated for 2 minutes at the same temperature. The Chip was primed using the "Priming Station", by adding 9 µL of "Gel-Dye-Mix" in the marked G position and pressurizing the chip for 30 seconds. Then 9 µL "Gel-Dye-Mix" were added into both other G positions. Seven and a half µL of "Marker" were added into the ladder position and 5 µL into every sample position. The denatured "Nano Ladder" (1.5 µL) was added to the ladder position and afterwards 1 µL of sample were added into all 12 sample wells (add 1 µL of $H_2O$ to not used wells). The Chip was placed on IKA Vortex machine and vortex for 1 minute at 2000 rpm was applied. This chip was measured in the instrument, and Replicon RNA peak was detected at 47-57 seconds. The RNA integrity was calculated in Expert 2100 software using Smear analysis by selecting the Replicon RNA region.

The relative RNA integrity % was calculated using the following equation:

$$\text{Relative } RNA \text{ integrity } \% = 100 \times \frac{RNA \text{ integrity after 2 weeks of storage}}{RNA \text{ integrity 1 h after the polyplex preparation}}$$

In-Vitro Transfection Assay

C2C12 cells were seeded in a 96-well plate (flat bottom) at concentration of 2×10^4 cells per well. The cells were maintained at 37° C. and 7.5% $CO_2$. After 24 h, the supernatant was discarded and replaced with 50 µL of DMEM Medium (+10% FCS).

Polyplexes were diluted (1:5) in DMEM medium with 10% FCS and pre-incubated for ~15 min. Then 50 µl of the polyplex solution was added to the cells to a final medium volume of 100 µl. After additional 48 h, Bright-Glo™ Luciferase assay Cat. #E2610, Promega GmbH, Mannheim, Germany) was performed according to manual instructions.

Relative luminescence % was calculated using the following equation:

$$\text{Relative luminesce } \% = \frac{\text{Absolute luminesence after 8 days of storage}}{\text{Absolute luminesence after 16 hours of storage}}$$

Figure 2:
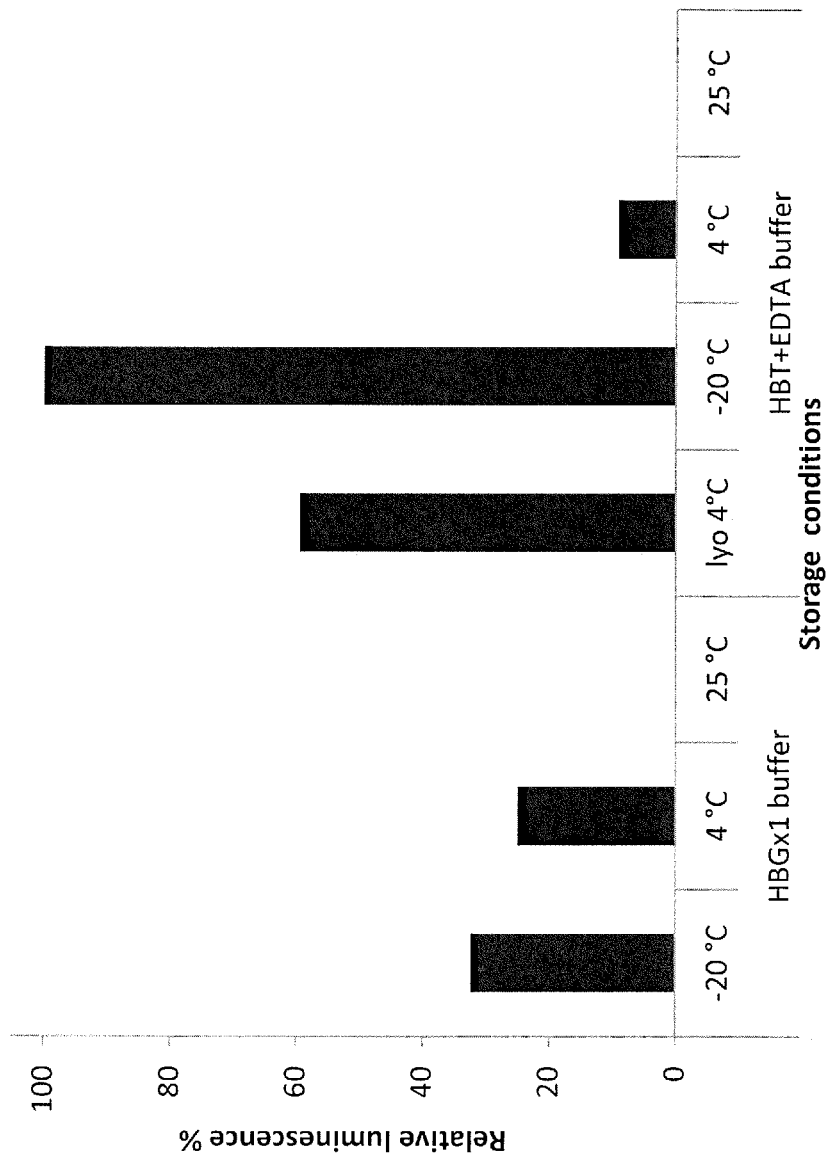
FIG. 2. Relative luminescence from C2C12 muscle cells after incubation with PEI/Replicon-RNA polyplexes at N/P 11.6 from different storage conditions after 1 week storage.

FIG. 2 shows the relative luminescence from C2C12 muscle cells after incubation with PEI/Replicon-RNA polyplexes at N/P 11.6 from different storage conditions after 1 week storage.

Figure 3:
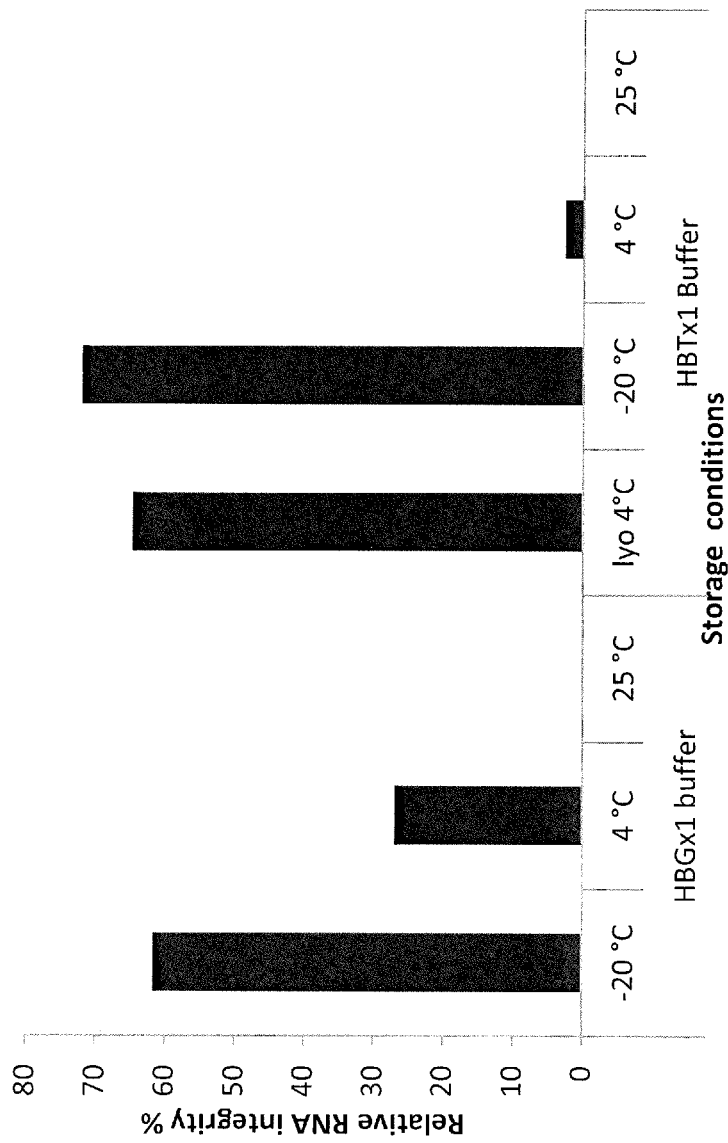
FIG. 3. Relative RNA integrity of PEI/Replicon-RNA polyplexes at N/P 11.6 at different storage conditions after 2 weeks storage.

FIG. 3 shows the relative RNA integrity of PEI/Replicon-RNA polyplexes at N/P 11.6 at different storage conditions after 2 weeks storage.

Results and Conclusions

Polyplexes have poor storage stability at liquid state (4 and 25° C.). The stability of polyplexes is significantly better at solid state (frozen or lyophilized) than at liquid state. The storage stability of polyplexes in HBT+EDTA buffer in solid state is significantly better than the storage stability in HBGx1 buffer.

For polyplexes in HBT+EDTA, solid state long storage stability is possible, while for polyplexes in HBGx1, liquid state long storage stability is very unlikely. Polyplex formulations with Replicon-RNA could be stabilized by addition of: trehalose 5-20% (w/v), EDTA 80 µM-5 mM.

Example 3: Description of Mw Calculation of Linear PEIs

Figure 4:
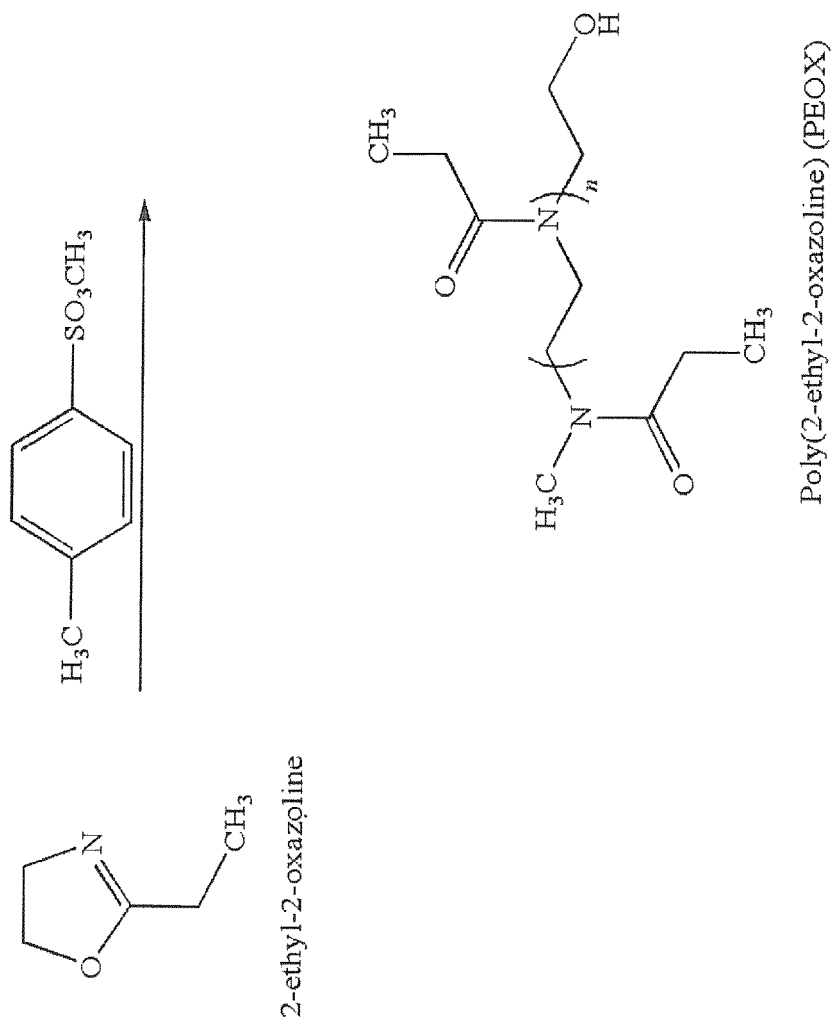
FIG. 4. poly(2-ethyl-2-oxazoline) is obtained by a ring-opening isomerization polymerization of 2-ethyl-2-oxazoline in the presence of initiators.
Figure 5:
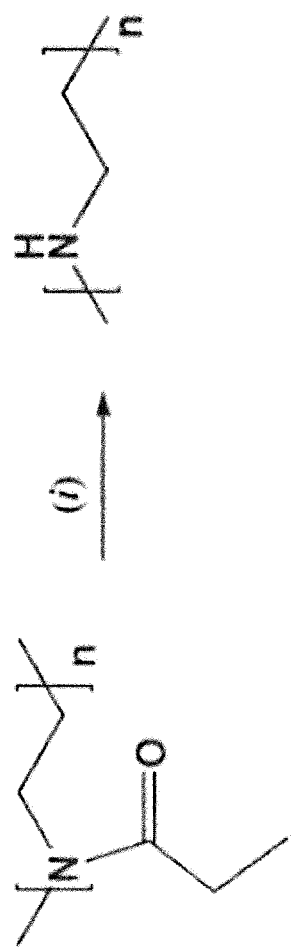
FIG. 5. Synthesis of fully deacylated linear PEI22, PEI87, and PEI217 by the acid hydrolysis of PEOZs. Conditions: (i) 24% (wt/vol) HCl, 110° C., 96 h; n=504 for 50-kDa PEOZ, 2,018 for 200-kDa PEOZ, and 5,044 for 500-kDa PEOZ.

Linear PEI is synthetized from 2-ethyl-2-oxazoline in two steps: First, poly(2-ethyl-2-oxazoline) is obtained by a ring-opening isomerization polymerization of 2-ethyl-2-oxazoline in the presence of initiators (FIG. 4). Then, PEOX (N-propionyl-PEI) is acid-hydrolyzed to cleave off the N-propionyl groups to yield PEI (FIG. 5).

Complete deacylation of PEOX(N-propionyl-PEI) with a molecular weight of 50 kDa gives a linear PEI with a molecular weight of 22 kDa. Determination of the molecular weight of the intermediate product (PEOX) is performed by gel permeation chromatography with a Refractive Index Detector or Multi-angle Light Scattering Detector. The full technical details are described in: Adib, Abdennaji, Fabrice Stock, and Patrick Erbacher. "Method for Manufacturing Linear Polyethylenimine (PEI) for Transfection Purpose and Linear PEI Obtained with Such Method." U.S. patent application Ser. No. 12/671,312.

According to this invention, PEIs, which were synthetized from PEOX with the MWs range of 40-60 kDa, are the potent transfection reagents for Replicon-RNA.

PEI for use according to the invention can be purchased from Polyplus-Transfection SA (Illkirch-Graffenstaden, France): in-vivo JetPEI, Polysciences Europe GmbH (Eppelheim, Germany): PEI MAX 40000, and Euromedex (Souffelweyersheim, France): Exgen 500.

Example 4: Aggregation Kinetics of Polyplexes

Materials and Methods

The polyplexes were prepared in HBGx1 at RNA concentration of 200 mg/L, as previously described in Example 2. They were diluted in HBGx1 and phosphate buffered saline pH 7.4 (PBS) to RNA concentration of 10 mg/l. The PBS was used in order to increase the ionic strength of solution. A 96 well plate was cleaned by filtrated air before adding the diluted polyplexes to the plate. The sizes were measured by DynaPro plate reader II instrument from WYATT technology GmbH (Dernbach, Germany). Cumulant fit was used for size calculation of monomodal samples, while regularization fit for multimodal samples.

Figure 6:
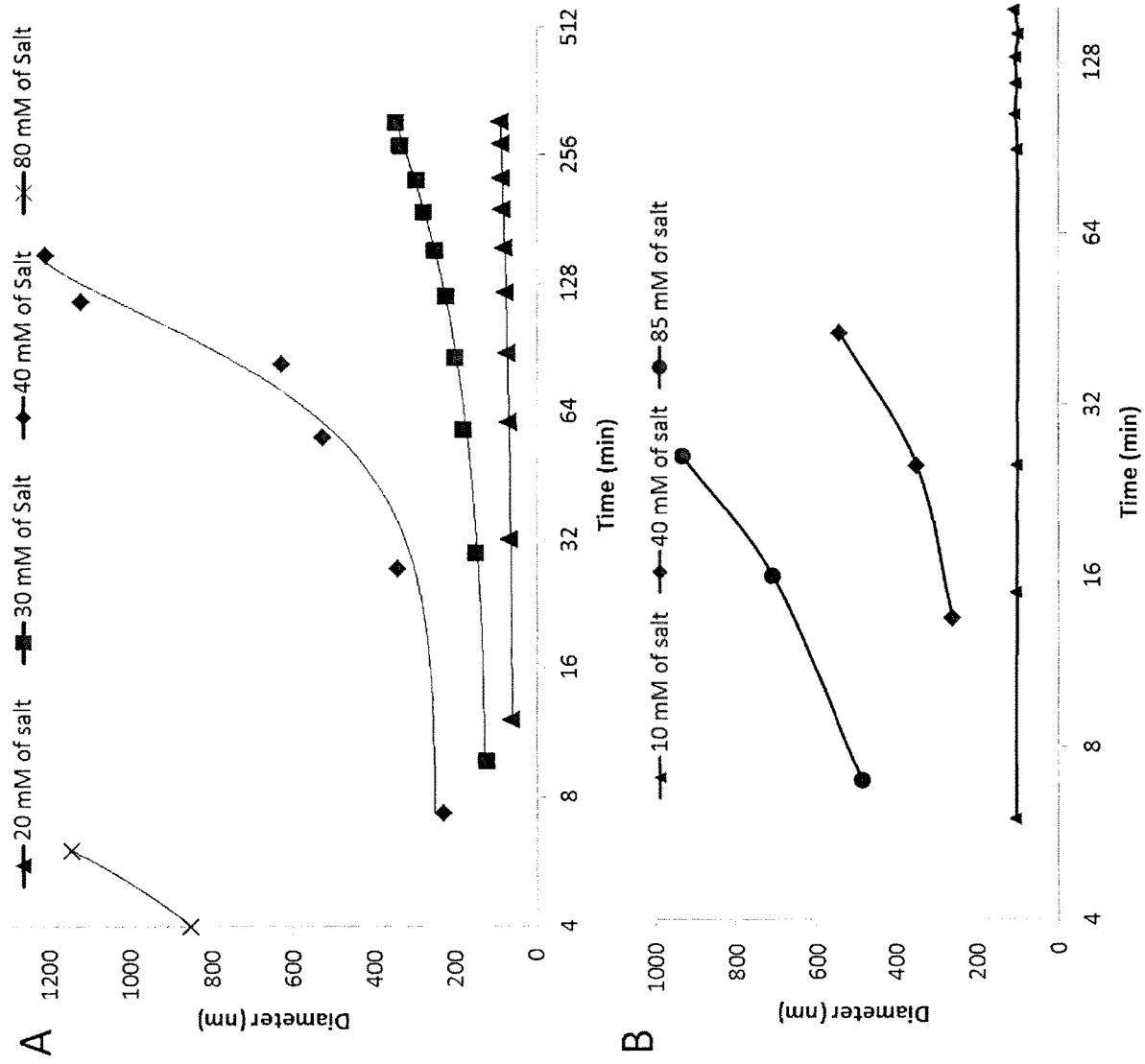
FIG. 6. Aggregation kinetics of IVT (A) and Replicon (B) polyplexes at increasing salt concentrations.

FIG. 6 shows the aggregation kinetics of IVT (A) and Replicon (B) polyplexes with JetPEI at increasing salt concentrations.

Results and Conclusions

High ionic strength leads to increase in the size of the polyplexes (FIG. 6). The ionic strength of the polyplex formulation has to be 520 mM in order to prevent aggregation of the polyplexes.

Example 5: Sterilization of Polyplexes by Filtration

Materials and Methods

Polyplexes were prepared at RNA concentration of 100 mg/L and N/P ratios of 11.5, 13.5 and 15.5, as previously described in the section "Stability studies of polyplexes".
RNA Concentration and Integrity The RNA was released from the polyplexes by incubation with Heparin. Ninety µl of free RNA (100 mg/l) or polyplexes were mixed with 10 µl of Heparin 20 g/l in Hepes 10 mM, pH 7.4, EDTA 1 mM. The mixture was incubated for 20 min at 30° C. in the vortex machine. Five µl of this mixture was mixed with 5 µl of formamide. Next, the RNA integrity was measured by Bioanalyzer with pico-chips. The RNA integrity was calculated, as described in example 2. The RNA concentration by was measured by Ribogreen assay with "Quant-iT RiboGreen RNA Reagent and Kit" (Cat. #R11490, Thermo Fischer Scientific), according to the manufacturer instructions for the high sensitivity method. Briefly, the mixture of polyplexes with heparin were incubated with Ribogreen fluorophore in Tris 10 mM, pH 7.5, EDTA 1 mM buffer. The fluorescence of Ribogreen was measured at excitation wavelength of 485 nm and emission 535 nm.
PEI Concentration A solution of CuSO4 23 mg (anhydrous) in 100 ml of NaAcetate 0.1 M, pH 5.4 (CSS reagent) was prepared. CSS reagent 600 µl was mixed with the polyplexes and incubated for 5 min at ambient temperature. The absorption of each solution was measured at 285 nm on a UV spectrophotometer against the blank using a 1 cm cuvette. A calibration curve with known PEI concentrations (0-1.55 mM) was prepared, and used to calculate the PEI concentration in the unknown samples. A background absorption of free RNA was subtracted from all samples.
Measurement of Electrophoretic Mobility (µ)

The polyplexes were diluted to RNA concentration of 20 mg/l in HBGx1 in 3.1 ml. Next they were centrifuged at 600 g for 2 min. Three samples of 1.05 ml were prepared for each formulation in plastic cuvettes. The electrophoretic mobility of the polyplexes was measured by laser dopler electrophoresis with the ζ-Wallis instrument (Corduan technologies, France). Medium resolution measurement with 1 sequence of 10 runs was used for each sample. Measurement with low signal to noise ratios, or with extreme µ (>3 or <−3 µm*cm/V*S) were excluded from the final analysis. All formulations were measured in triplicates.
Filtration of Polyplexes Three tubes with 2.68 ml of polyplexes at three different N/P ratios were prepared. The polyplexes (1.34 ml) were filtrated through sterile Millex-GP Med Syringe Filter Units with pores of 220 nm (Cat. #SLMPL25SS, Merck Millipore). Physicochemical properties were measured before and after the filtration.

Figure 7:
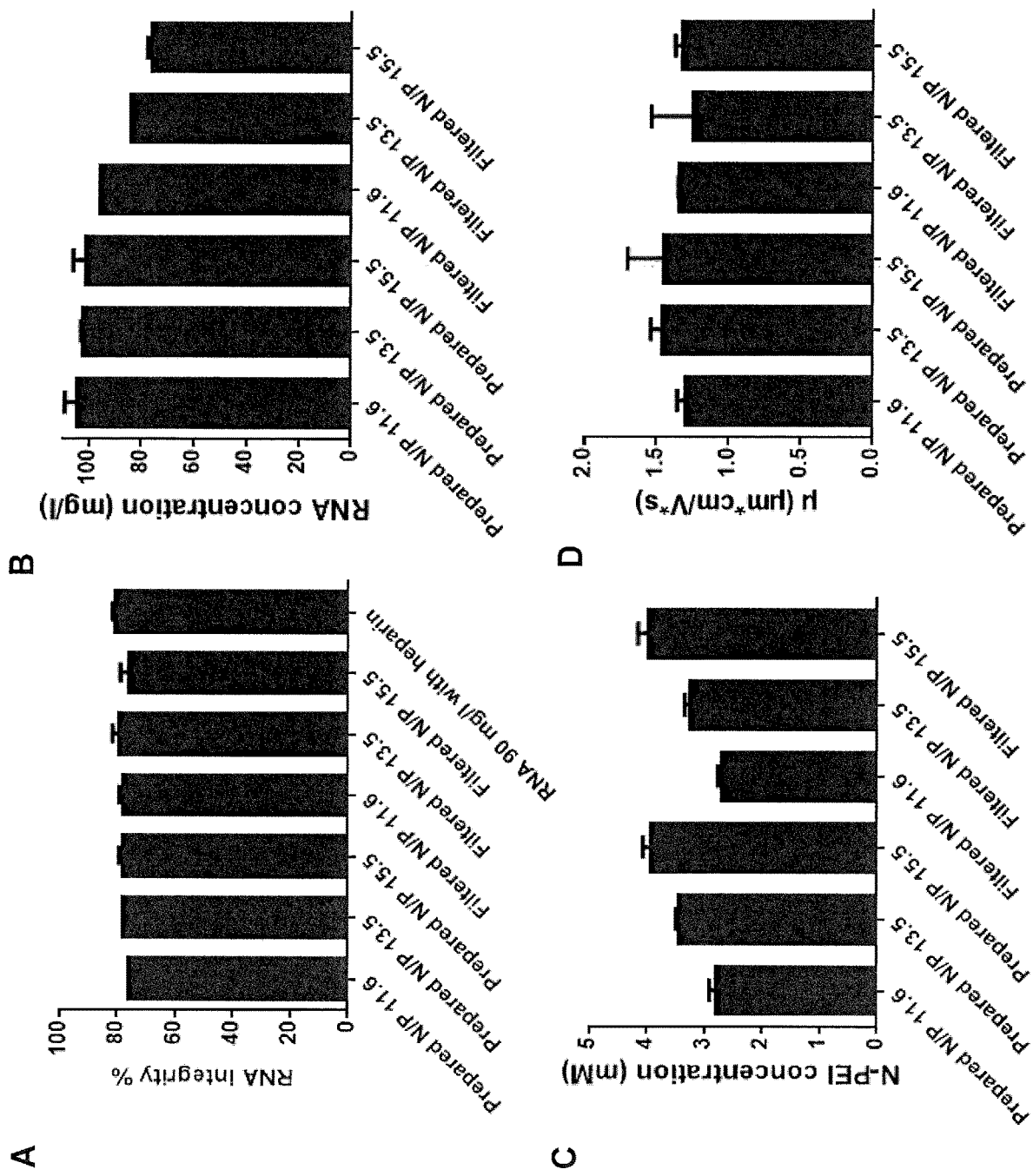
FIG. 7. Physicochemical parameters of polyplexes before (initial) and after (final) the filtration. A and B. The diameter and the polydispersity of the polyplexes were measured by DLS. C. RNA was released from the polyplexes by Heparin, and measured by UV absorbtion at 260 nm. D. PEI concentration was measured by $CuSO_4$ assay.

FIG. 7 shows the physicochemical parameters of polyplexes before (Prepared) and after (Filtered) the filtration. A and B. RNA was released from the polyplexes by Heparin. Then Replicon-RNA intergrity (A) was measured by capillary electrophoresis with the bioanalyzer instrument. Replicon-RNA concentration (B) was measured by Ribogreen fluoresence. C. PEI concentration was measured by CuSO4 assay. D. Electrophoretic mobility (p) was measured by laser-Doppler electrophoresis.

Results and Conclusions

Syringe Filter Units are suitable method for sterilization of polyplexes. The polyplexes have to be small <120 nm in order to sterilize them by filtration. At N/P ratio 11.6 the phyisicochemical properties of the polyplexes are not changed by the filtration.

When then N/P ratio is increased above 11.6, then there is loss of RNA during the filtration.

Example 6: Effect of PEI Purity on Transfection of Replicon-RNA/PEI Formulations Materials and Methods The following high-purity PEIs were purchased from Polyplus-Transfection SA (Illkirch-Graffenstaden, France): in-vivo JetPEI and from Polysciences Europe GmbH (Eppelheim, Germany): PEI MAX 40000.

The following regular-purity PEI was purchased from Polysciences Europe GmbH (Eppelheim, Germany): PEI 25000.

The polyplexes were prepared in HBGx1 at RNA conentration of 100 mg/L, as previously described in Example 2.

In-Vivo Transfection

Mice are anaesthetized with isoflurane and posterior side of hind-legs were shaved and disinfected with 70% EtOH-solution. Twenty μl of the investigated formulations were injected into the *Musculus tibialis* posterior muscle with an Insulin-syringe pre-equipped with a cannula of 30G in size. The mouse was observed until regaining consciousness for signs of pain, suffering and distress.

At day of measurement, mice were injected i.p. with Luciferin-solution. Subsequently, mice were anesthetized with Isoflurane and placed on a heat mat (37° C.) inside the IVIS® Spectrum (Perkin Elmer) imaging chamber with constant supply of Isoflurane/oxygen via individual anesthesia masks. Five minutes after injection of luciferin, detection of bioluminescence light over one minute via camera was performed. Resulting images were analyzed using the software "LivingImage" (Perkin Elmer).

Figure 8:
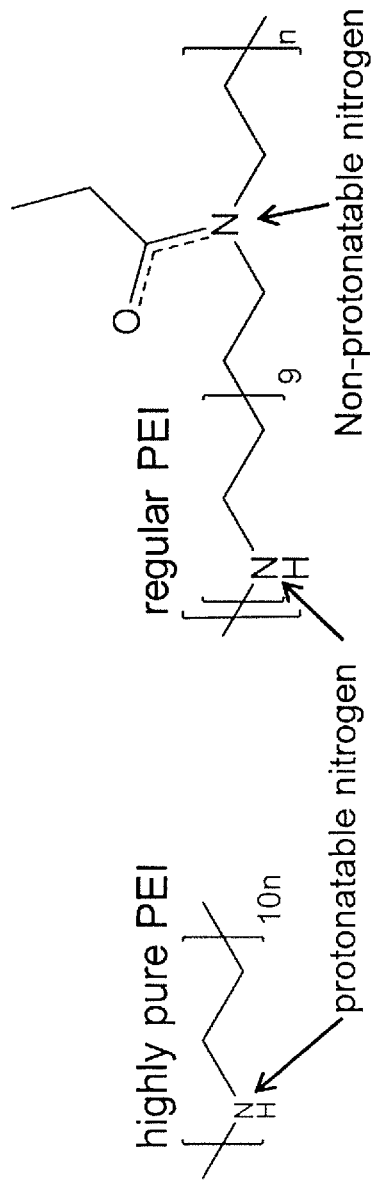
FIG. 8. Comparison of the chemical structures of highly pure PEI and regular purity PEI. n=58 for PEI of 25 kDa. The average number of the —CH2CH2NH— monomers in PEI 25 kD is 581, which is also the length of the contiguous stretch of potentially protonatable nitrogens. Assuming a uniform distribution of the N-propionyl moieties in the regular PEI25, its contiguous stretch of protonatable nitrogens is only 64.

FIG. 8 shows a comparison of the chemical structures of highly pure PEI and regular purity PEI. n=58 for PEI of 25 kDa. The average number of the —CH2CH2NH-monomers in PEI 25 kD is 581, which is also the length of the contiguous stretch of potentially protonatable nitrogens. Assuming a uniform distribution of the N-propionyl moieties in the regular PEI25, its contiguous stretch of protonatable nitrogens is only 64.

Figure 9:
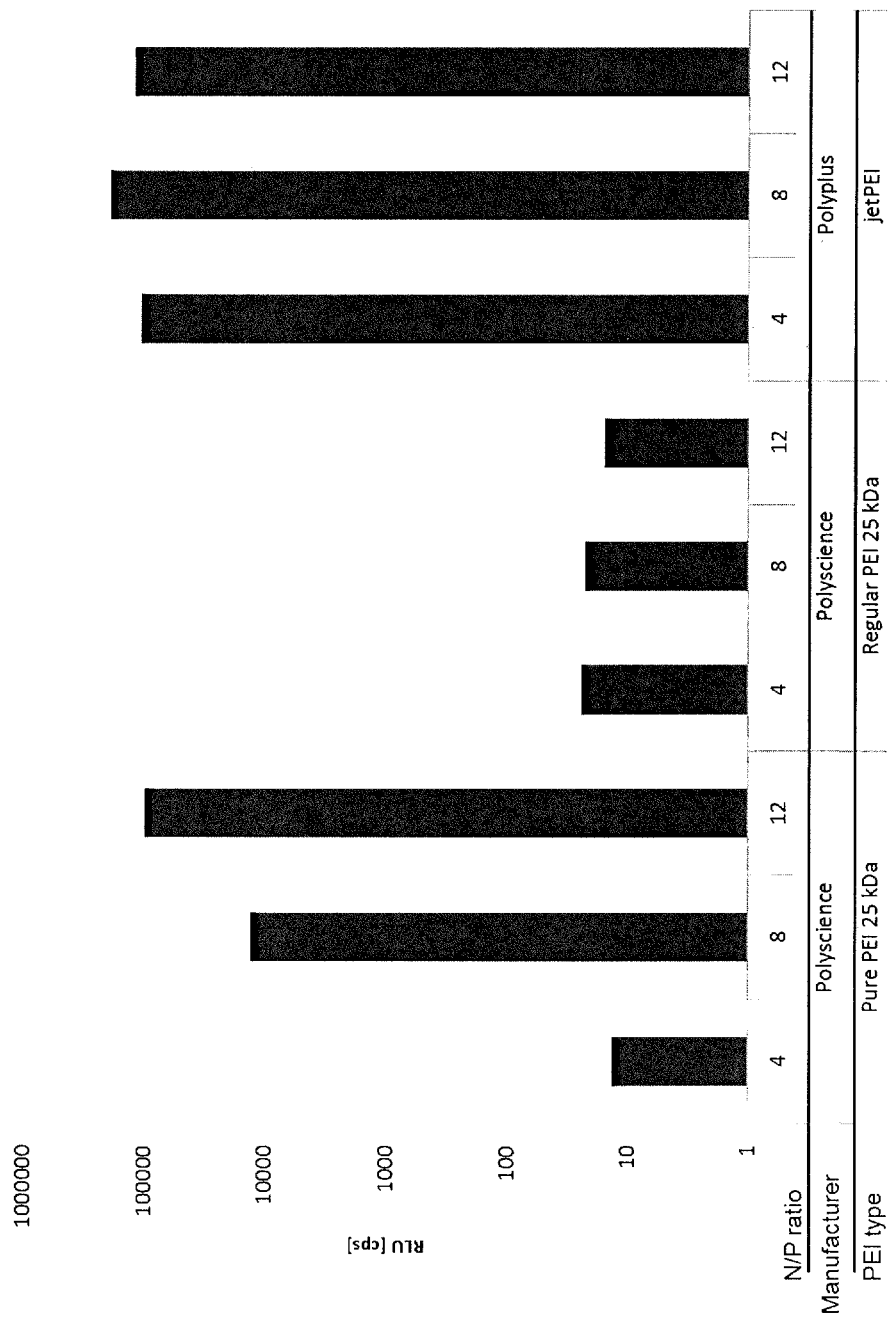
FIG. 9. Transfection of C2C12 muscle cells in-vitro by Replicon-RNA polyplexes that were prepared using PEIs of different purity level at different N/P ratios.

FIG. 9 shows the transfection of C2C12 muscle cells in-vitro by Replicon-RNA polyplexes that were prepared using PEIs of different purity level at different N/P ratios.

Figure 10:
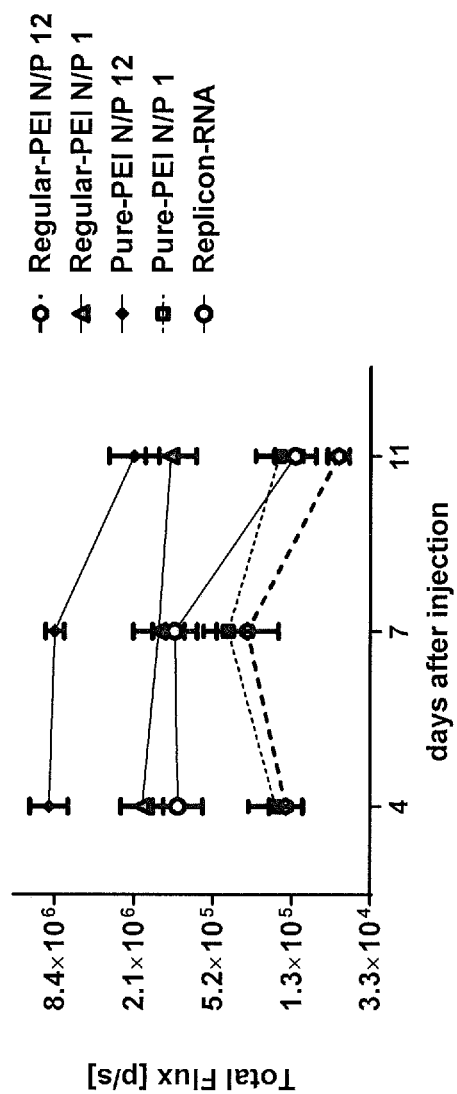
FIG. 10. Replicon-RNA Polyplexes at N/P ratios of 1 (−) and 11.6 (+) were prepared with highly pure PEI (jetPEI) and regular purity PEI (25 kDa). Free RNA was used as a control. The formulations were injected i.m. to the posterior limbs of the mice (n=3). Luminescence signals were recorded from the muscles of the mice.

According to FIG. 10, Replicon-RNA Polyplexes at N/P ratios of 1 (−) and 11.6 (+) were prepared with highly pure PEI (jetPEI) and regular purity PEI (25 kDa). Free RNA was used as a control. The formulations were injected i.m. to the posterior limbs of the mice (n=3). Luminescence signals were recorded from the muscles of the mice.

Results and Conclusions

Polyplexes, which were prepared using highly pure PEI, transfect muscle cells in-vitro better than regular purity PEI. Polyplexes have the highest transfection efficacy in-vivo at N/P 11.6 after i.m. injection.

Cationic polyplexes with highly pure PEI at N/P 11.6 can transfect the muscle tissue in-vivo significantly better (4-5 folds difference) than free Replicon-RNA.

Anionic polyplexes with highly pure PEI at N/P 1, polyplexes with regular purity PEI at N/P 1, and cationic polyplexes with regular pure PEI at N/P 11.6 transfect the muscle tissue worse than free Replicon-RNA.

Example 7: High Transfection Efficacy of Replicon-RNA by Pure PEIs from Different Providers and Lyophilized Polyplexes Materials and Methods The following high-purity PEIs were purchased from Polyplus-Transfection SA (Illkirch-Graffenstaden, France): in-vivo JetPEI, and Euromedex (Souffelweyersheim, France): Exgen 500 and from Polysciences Europe GmbH (Eppelheim, Germany): PEI MAX 40000.

The polyplexes were prepared in HBGx1 at RNA conentration of 100 mg/L, as previously described in Example 2. All formulations were prepared in HBGx1 buffer except of the lyophilized formulation, which was prepared in HBTx1 buffer. The lyophilization of the polyplexes in HBTx1 buffer was performed, as previously described in Example 2. The formulations were injected i.m. to the posterior limbs of the mice (n=3), and the luminesence signals were recorded from the muscles of the mice, as previously described in Example 6.

Figure 11:
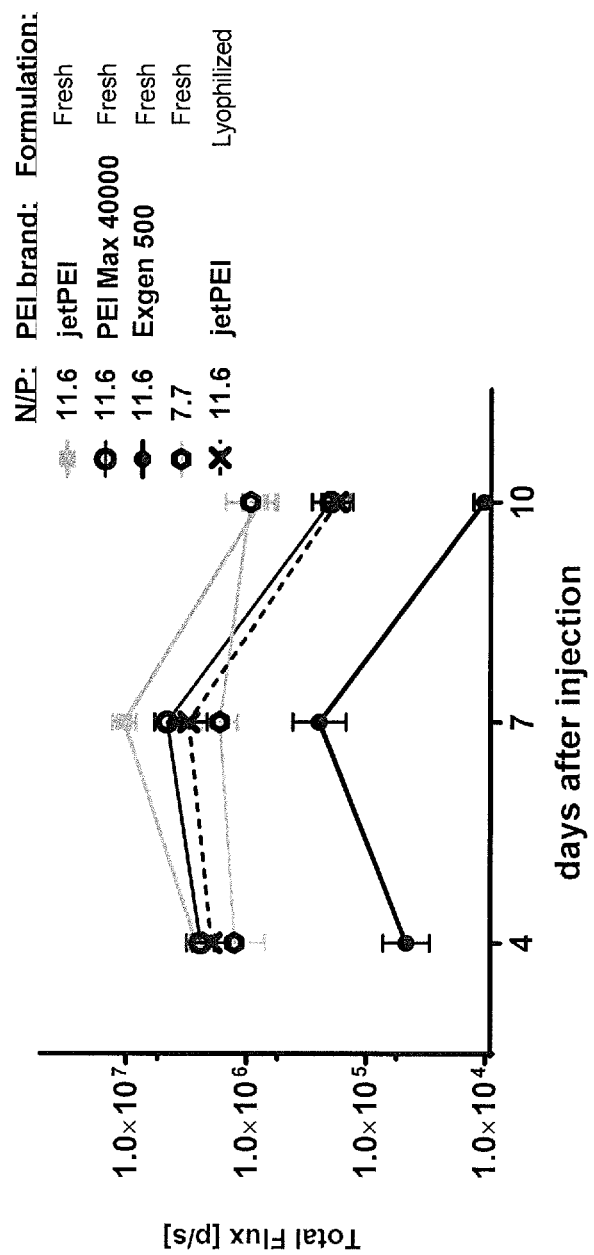
FIG. 11. Replicon-RNA Polyplexes at N/P ratios of 7.7 and 11.6 were prepared with highly pure PEIs: jetPEI (from Polyplus), PEI-Max 40000 (from Polyscience), and Exgen 500 (from Eurodamex). All formulations were prepared in HBGx1 buffer except of the lyophilized formulation, which was prepared in HBTx1 buffer. The formulations were injected i.m. to the posterior limbs of the mice (n=3). Luminesence signals were recorded from the muscles of the mice.

For the experiment of FIG. 11, Replicon-RNA Polyplexes at N/P ratios of 7.7 and 11.6 were prepared with highly pure PEIs: jetPEI (from Polyplus), PEI-Max 40000 (from Polyscience), and Exgen 500 (from Eurodamex).

TABLE 3

Mann Whitney test, two tailed, for statistical significance (P-value) of the difference between the formulations in FIG. 11.

| Hypothesis | Day | P Value |
| --- | --- | --- |
| Fresh JetPEI is different than PEI MAX 40000 N/P 11.6 | 4 | 0.474 |
| Fresh JetPEI is different than Exgen N/P 7.7 | 4 | 0.065 |
| Fresh JetPEI is different than lyophilized JetPEI | 4 | 0.387 |
| Fresh JetPEI is different than PEI MAX 40000 N/P 11.6 | 7 | 0.180 |
| Fresh JetPEI is different than Exgen N/P 7.7 | 7 | 0.009* |
| Fresh JetPEI is different than lyophilized JetPEI | 7 | 0.065 |
| Fresh JetPEI is different than PEI MAX 40000 N/P 11.6 | 10 | 0.132 |
| Fresh JetPEI is different than Exgen N/P 7.7 | 10 | 0.788 |
| Fresh JetPEI is different than lyophilized JetPEI | 10 | 0.093 |
| Fresh JetPEI is different than PEI MAX 40000 N/P 11.6 | 4-10 | 0.7 |
| Fresh JetPEI is different than Exgen N/P 7.7 | 4-10 | 0.7 |
| Fresh JetPEI is different than lyophilized JetPEI | 4-10 | 0.7 |

Figure 12:
FIG. 12. Lyophilized cakes of JetPEI/Replicon-RNA polyplexes at N/P 11.6 prepared with different buffers.

FIG. 12 shows lyophilized cakes of JetPEI/Replicon-RNA polyplexes at N/P 11.6 prepared with different buffers.

Results and Conclusions

Polyplexes of Replicon-RNA transfect the muscle tissue efficiently after i.m. injection (FIG. 11). The high purity PEIs: jetPEI (from Polyplus), PEI-Max 40000 (from Polyscience), and Exgen 500 (from Eurodamex) could be used for the preparation of the polyplexes. Exgen-500 polyplexes transfect better at N/P 7.7 than 11.6.

The lyophilizate of polyplexes in trehalose has a cake-like morphology, while in glucose the lyophilizate collapses, and it is hard to dissolve it in water (FIG. 12).

Trehalose is preferable to Glucose for lyophilization of polyplexes. The lyophilized polyplexes perform in-vivo similarly to freshly prepared liquid-polyplexes.

Example 8: Transfection of IVT-RNA to Muscle Cells by Pure PEI Polyplexes

Materials and Methods

In vivo-jetPEI™ Reagent, Cat. #201-50G, was purchased from Polyplus-Transfection (Illkirch, France). In vitro transcribed (IVT) mRNA that encodes for luciferase, Construct pST1-475, was provided by RNA Biochemistry unit (Biontech RNA Pharmaceuticals, Mainz, Germany).

Polyplexes of IVT-RNA and PEI were prepared as previously described in Example 2. Different N/P ratios were prepared by keeping the RNA concentration constant and increasing the PEI concentration.

Transfection of muscle cells in-vitro was performed as previously described in Example 2.

In-vivo transfection studies were performed as previously described in Example 6.

Figure 13:
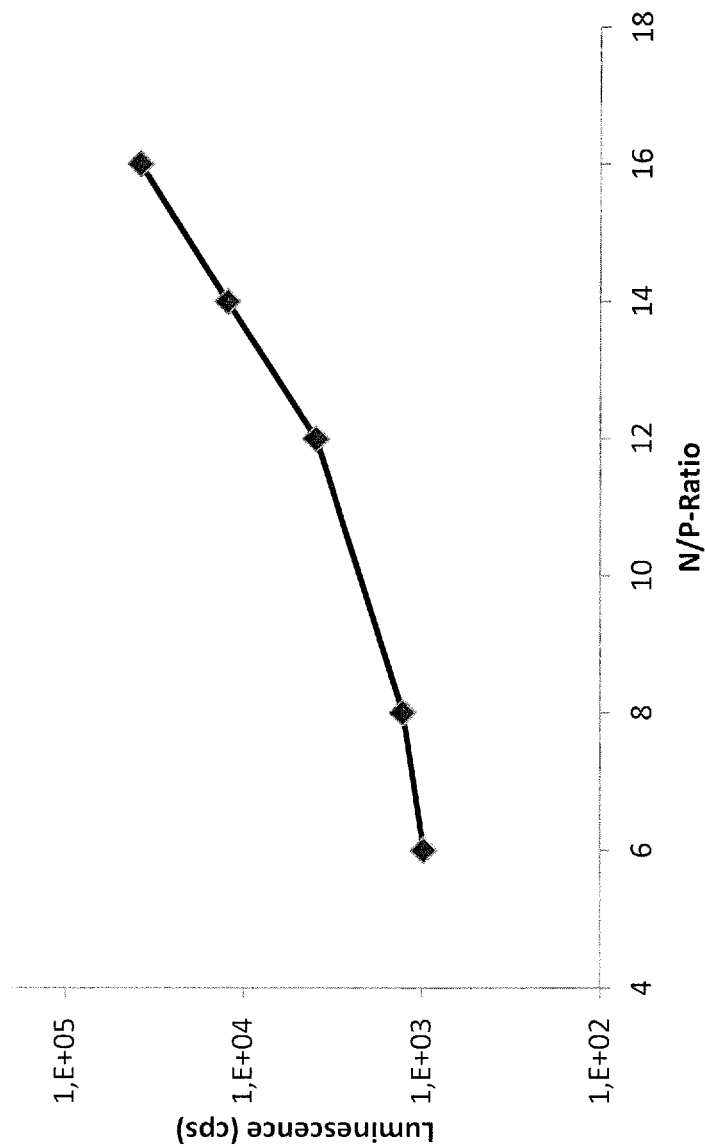
FIG. 13. C2C12 muscle cells were transfected in-vivo by IVT-RNA that encodes for luciferase. The RNA was complexes with JetPEI at different N/P ratios in HBGx1 buffer. Luminescence signal was measured 24 h after the transfection.

According to FIG. 13, C2C12 muscle cells were transfected in-vitro by IVT-RNA that encodes for luciferase. The RNA was complexes with JetPEI at different N/P ratios in HBGx1 buffer. Luminescence signal was measured 24 h after the transfection.

Figure 14:
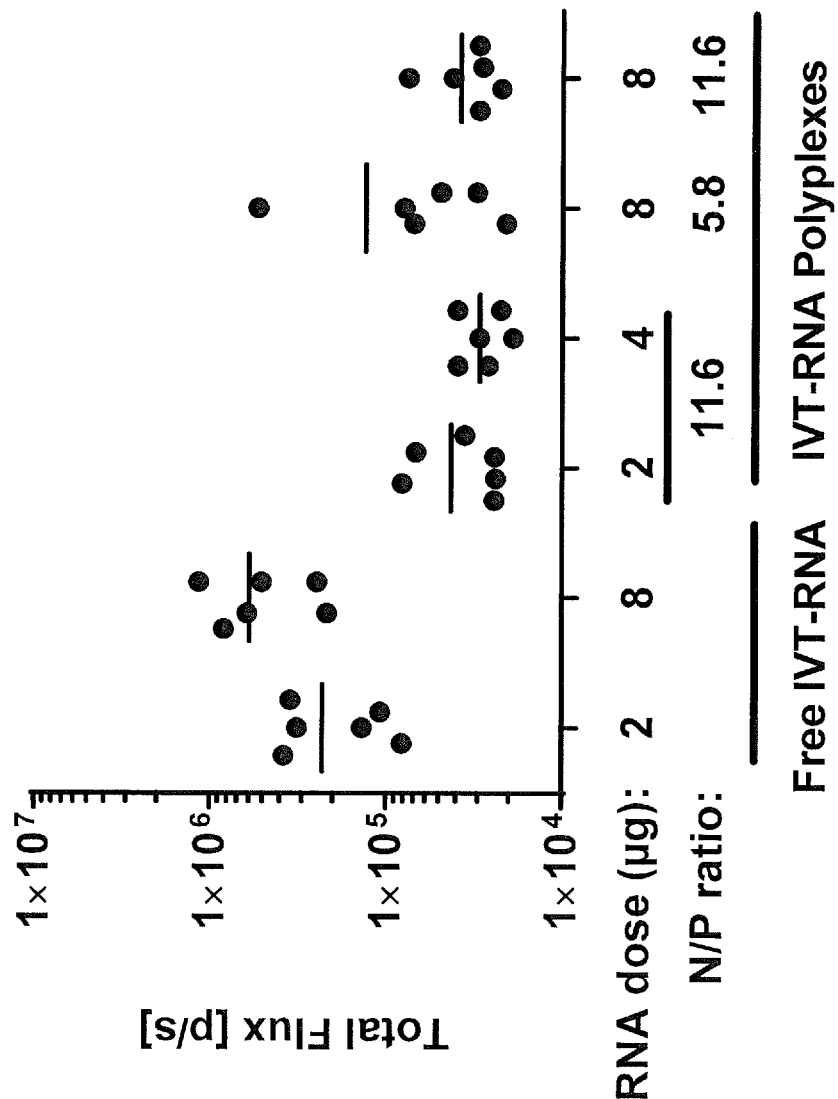
FIG. 14. IVT-RNA Polyplexes at N/P ratios of 5.8 and 11.6 were prepared with pure PEI in HBGx1 buffer. Free IVT-RNA in HBGx1 buffer was used as a control. The formulations were injected i.m. to the posterior limbs of the mice (n=3) at RNA doses of 2-8 µg per injection. Luminesence signals were recorded from the muscles of the mice 6 h after the injection.

According to FIG. 14, IVT-RNA Polyplexes at N/P ratios of 5.8 and 11.6 were prepared with pure PEI in HBGx1 buffer. Free IVT-RNA in HBGx1 buffer was used as a control. The formulations were injected i.m. to the posterior limbs of the mice (n=3) at RNA doses of 2-8 µg per injection. Luminescence signals were recorded from the muscles of the mice 6 h after the injection.

Results and Conclusions

Polyplexes of IVT-RNA and highly-pure PEI can transfect muscle cells efficiently in-vitro. There is a positive correlation between the transfection efficiency and N/P ratio (FIG. 13). Free IVT-RNA does not transfect the cells in-vitro.

Polyplexes with highly pure PEI at N/P ratios 5.8 and 11.6 transfect the muscle tissue in-vivo significantly worse than free IVT-RNA (FIG. 14).

Example 9: Effect of Particle Size and Preparation Conditions on Transfection by Replicon-RNA Polyplexes Materials and Methods Polyplexes of Replicon-RNA and PEI were prepared as previously described in Example 2. The polyplexes were prepared at 5 different RNA: 100, 250, 500, 750, 1000 mg/l. The PEI concentration was increased appropriately in order to keep the N/P ratio at 11.6 for all formulations.

Size of the polyplexes was measured as previously described in Example 4.

Transfection of muscle cells in-vitro was performed as previously described in Example 2.

In-vivo transfection studies were performed as previously described in Example 6.

Figure 15:
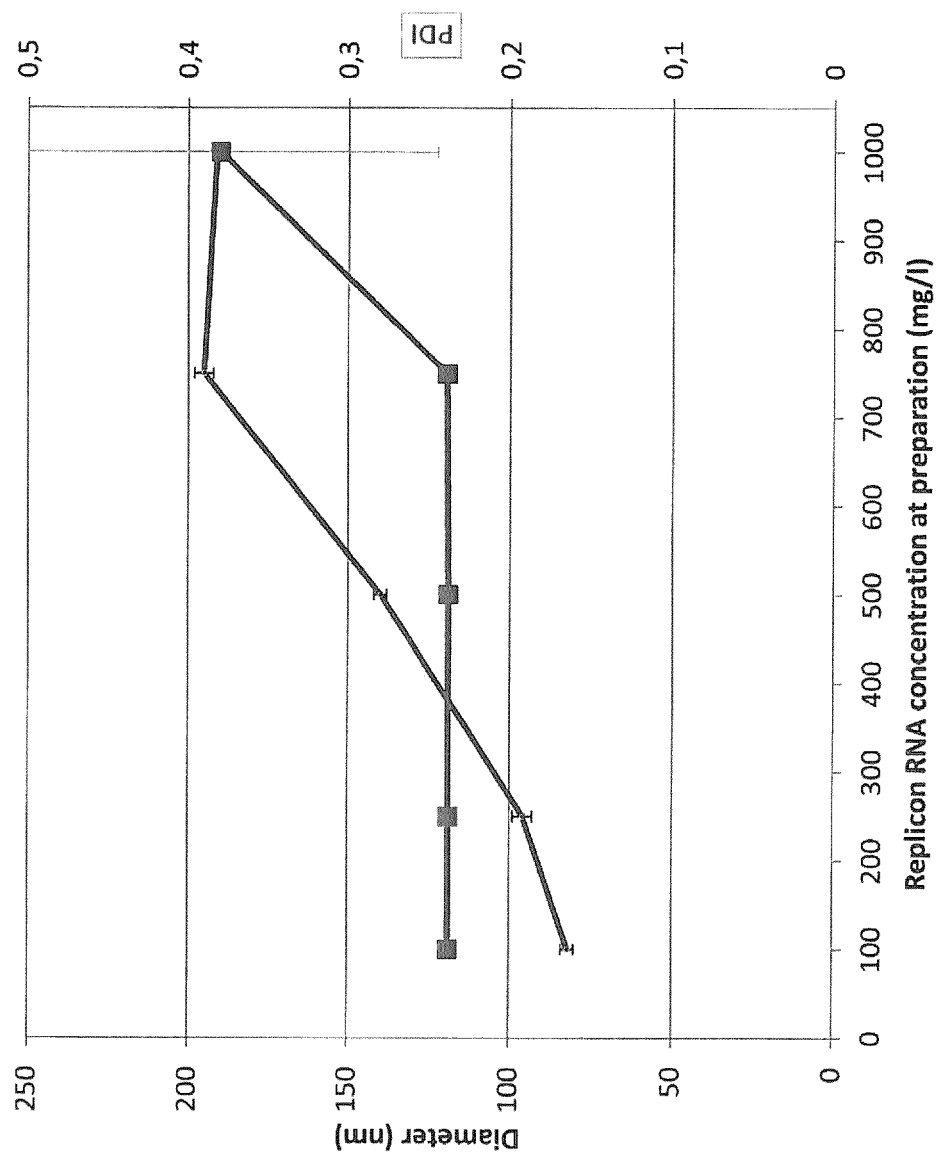
FIG. 15. Polyplexes of Replicon-RNA and jetPEI were prepared at different RNA concentration at N/P ratio 11.6 in HBGx1 buffer. For size measurements by DLS the polyplexes were diluted to RNA concentration of 10 mg/l.

According to FIG. 15, polyplexes of Replicon-RNA and jetPEI were prepared at different RNA concentration at N/P ratio 11.6 in HBGx1 buffer. For size measurements by DLS the polyplexes were diluted to RNA concentration of 10 mg/l.

Figure 16:
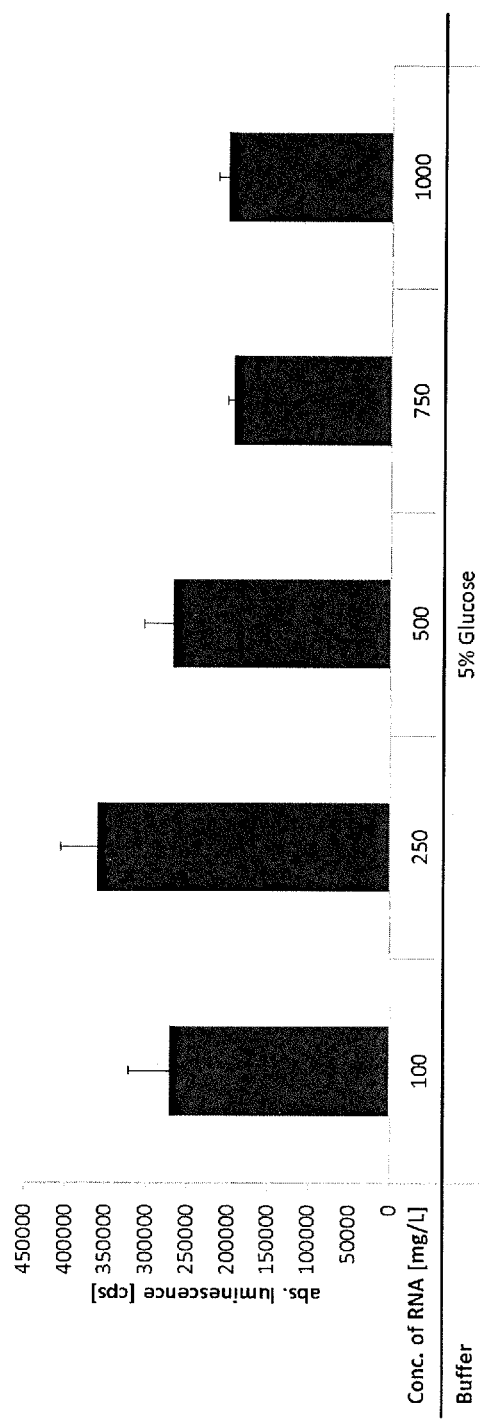
FIG. 16. C2C12 muscle cells were transfected in-vitro by the polyplexes from FIG. 16. The luminescence signal was measured 24 h after the transfection.

According to FIG. 16, C2C12 muscle cells were transfected in-vitro by the polyplexes from FIG. 16. The Luminescence signal was measured 24 h after the transfection.

Figure 17:
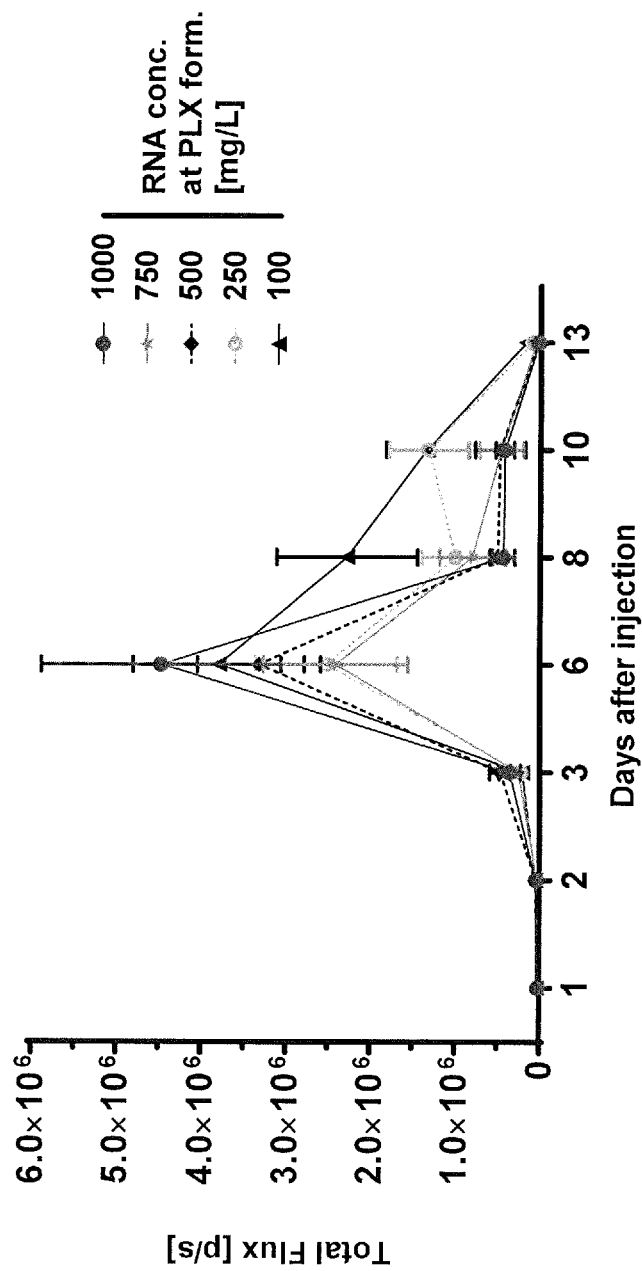
FIG. 17. Rep-RNA Polyplexes at N/P ratio 11.6 were prepared with pure PEI in HBGx1 buffer at different RNA concentration as in FIG. 16. The formulations were injected i.m. to the posterior limbs of the mice (n=3) at RNA doses of 2-8 µg per injection. Luminesence signals were recorded from the muscles of the mice.

According to FIG. 17, Rep-RNA Polyplexes at N/P ratio 11.6 were prepared with pure PEI in HBGx1 buffer at different RNA concentration as in FIG. 16. The formulations were injected i.m. to the posterior limbs of the mice (n=3) at RNA doses of 2-8 µg per injection. Luminesence signals were recorded from the muscles of the mice.

Results and Conclusions

Polyplexes are good transfection agents for Replicon-RNA. The bioactivity of the polyplexes in terms of efficiency of RNA-translation in muscle tissue is not influenced by RNA concentration (0.1-1 g/l) at time of polyplex formation.

Size of polyplexes in the range of 60-200 nm does not have an effect of the transfection efficacy of the polyplexes in-vitro and in-vivo (i.m. injection).

Example 10: Different Polyplexes Perform Differently after s.c. Or i.m. Injections Into Mice Materials and Methods In vivo-jetPEI™ Reagent, Cat. #201-50G, was purchased from Polyplus-Transfection SA (Illkirch, France). Linear PEI 22 kDa was provided by Prof. Cheradame (Polytheragene, EVRY cedex, France). RNA that encodes for luciferase, Construct D1-824 Replicon, ID 1600801, was provided by RNA Biochemistry unit (Biontech RNA Pharmaceuticals, Mainz, Germany).

Polyplexes with JetPEI were prepared in HBGx1 at RNA concentration of 500 mg/L, as previously described in Example 2.

Polyplexes with Polytheragene-PEI were prepared similarly to the procedure with JetPEI but with two modifications:
1. HEPES 10 mM, pH 7.4 buffer was used instead of HBGx1 for the preparation of the polyplexes.
2. N/P ratio of 15.8 was used instead of 11.6.

The preparation of the Polyplexes with Polytheragene-PEI was performed according to the following article: Démoulins, Thomas, et al. "Polyethylenimine-based polyplex delivery of self-replicating RNA vaccines." *Nanomedicine: Nanotechnology, Biology and Medicine* (2015).

The polyplexes were diluted in HBGx1 or Opti-MEM (Cat. #31985062, Thermo Fisher Scientific, Schwerte, Germany) buffers to final RNA concentrations of 5 mg/l for in-vitro studies and 100 mg/l for in-vivo studies.

In-vitro studies were performed as previously described in Examples 1 and 2.

In vivo studies were performed as previously described in Example 6.

Results and Conclusions

Figure 18:
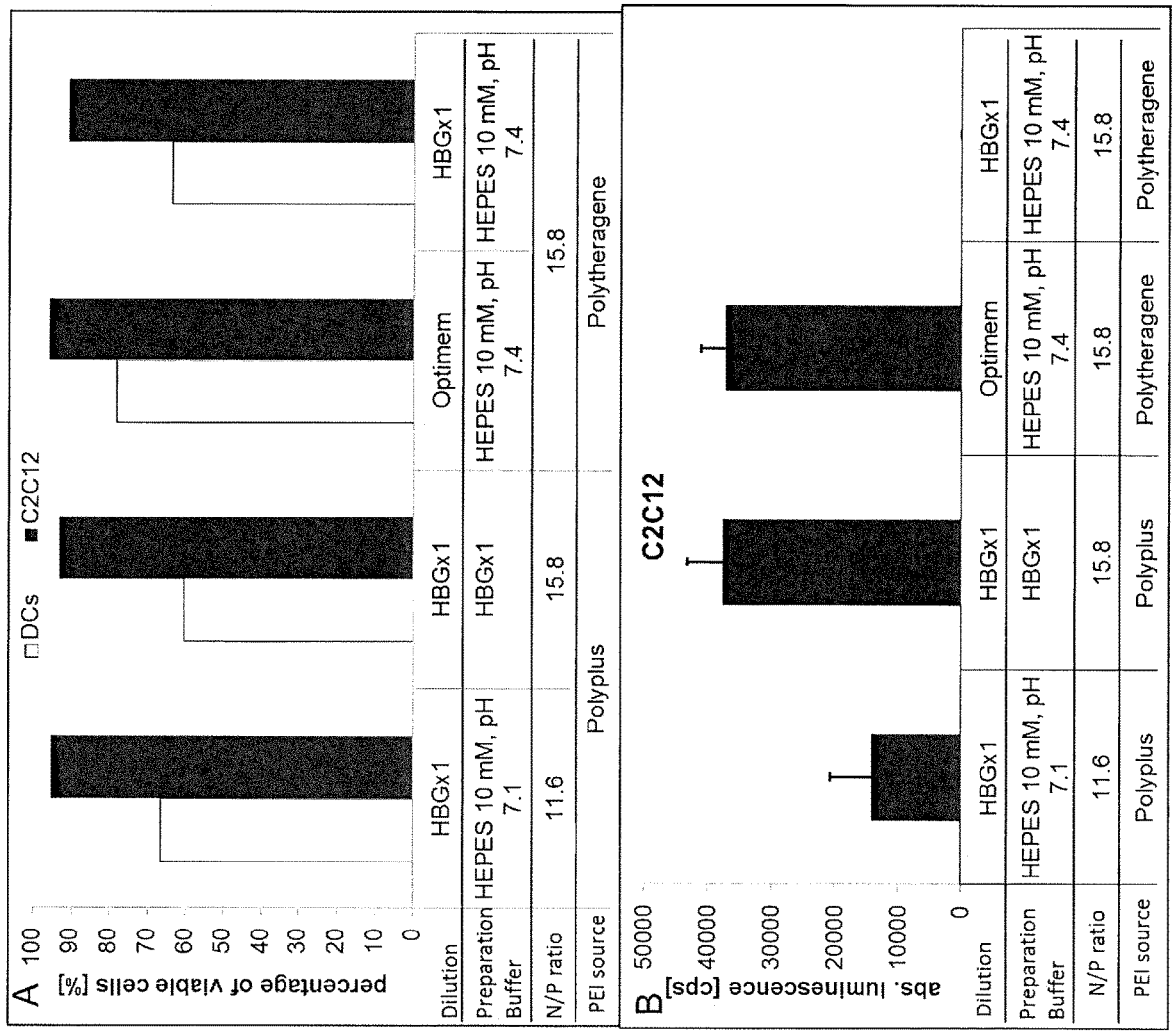
FIG. 18. In-vitro studies with PEI/Replicon-RNA polyplexes on human Dendritic cells (DCs) and mouse muscle cells (C2C12) A. Toxicity (expressed as % of viable cells after treatment with polyplexes) B. Transfection (expressed as luminescence emission after treatment with polyplexes). The transfection results are shown only for C2C12 cells.

FIG. 18 shows in-vitro studies with PEI/Replicon-RNA polyplexes on human Dendritic cells (DCs) and mouse muscle cells (C2C12) A. Toxicity (expressed as % of viable cells after treatment with polyplexes) B. Transfection (expressed as luminescence emission after treatment with polyplexes). The transfection results are shown only for C2C12 cells.

Figure 19:
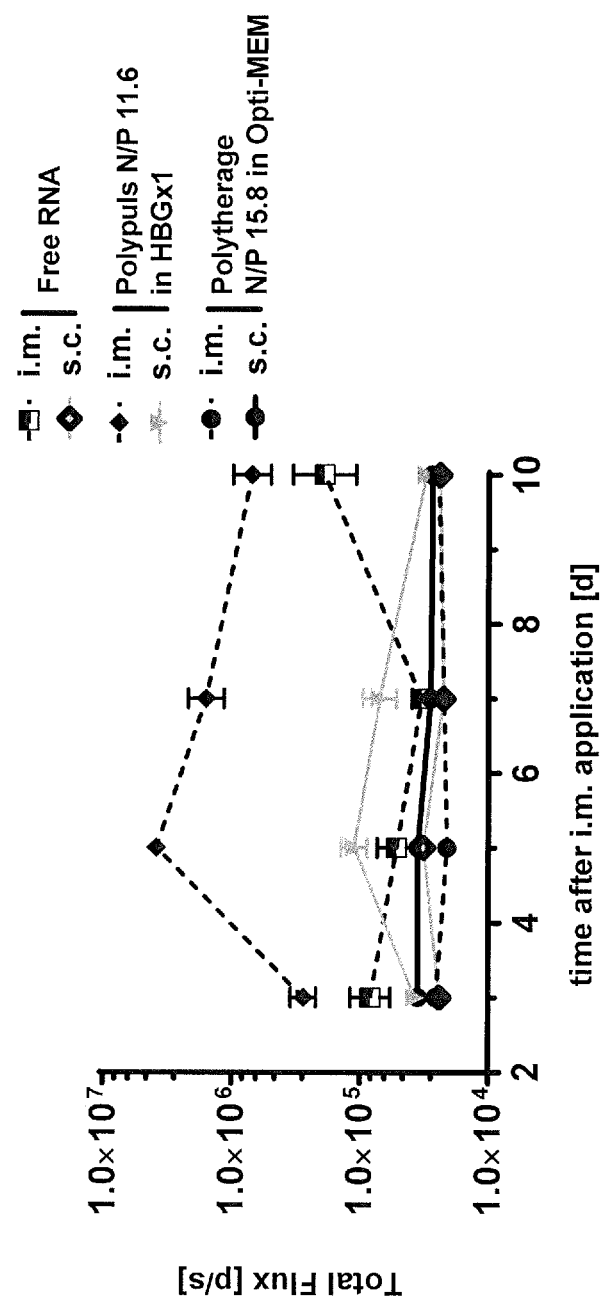
FIG. 19. Rep-RNA Polyplexes at N/P ratios 11.6 or 15.8 were prepared with PEI from Polyplus or Polytheragene in HBGx1 or Hepes 10 mM buffers. Before injection to mice the polyplexes were diluted in HBGx1 or Opti-MEM buffers. The formulations were injected i.m. to the posterior limbs of the mice (n=3) at RNA doses of 2 µg per injection. Luminesence signals were recorded from the muscles of the mice.

For the results of FIG. 19, Replicon-RNA Polyplexes at N/P ratios 11.6 or 15.8 were prepared with PEI from Polyplus or Polytheragene in HBGx1 or Hepes 10 mM buffers. Before injection to mice the polyplexes were diluted in HBGx1 or Opti-MEM buffers. The formulations were injected i.m. to the posterior limbs of the mice (n=3) at RNA doses of 2 µg per injection. Luminesence signals were recorded from the muscles of the mice.

Results and Conclusions

TABLE 4

Comparison between sizes of the different polyplexes

| # | PEI manufacturer | N/P | Preparation Buffer | Dilution Buffer | Diameter (nm) | PDI |
|---|---|---|---|---|---|---|
| 1 | Polyplus | 11.6 | HEPES 10 mM, pH 7.1 | HBGx1 | 112 | 0.277 |
| 2 | Polyplus | 15.8 | HBGx1 | HBGx1 | 107 | 0.239 |
| 3 | Polytheragene | 15.8 | HEPES 10 mM, pH 7.4 | Opti-MEM | >1000 | multi-modal |
| 4 | Polytheragene | 15.8 | HEPES 10 mM, pH 7.4 | HBGx1 | 94 | 0.237 |

Opti-MEM has higher ionic strength than 20 mM. In Opti-MEM, the poylplexes aggregate fast (Table 4), therefore this formulation is not suitable for pharmaceutical development.

The polyplexes described herein (PEI from polyplus, N/P 11.6, HBGx1) have very different characteristics than previously described polyplexes (PEI from polytheagene, N/P 15.8, Opti-MEM). In Opti-MEM, the poylplexes have a diameter >1000 nm and multimodal size distribution. The polyplexes described herein have a diameter of ~100 nm and low polydispersity.

In-vitro, all polyplexes are more toxic to dendritic cells than muscle cells. Probably, dendritic cells uptake the polyplexes after s.c. injection, while muscle cells are transfected by the polyplexes after i.m. injection.

The transfection of muscle-cells in-vitro by the polypleplex described herein and previously described polyplexes is similar.

The transfection in-vivo by the polyplexes described herein and previously described polyplexes is different and it depends on the route of application. The polyplexes described herein transfect well after i.m. injection and worse after s.c. injection. The previously described polyplexes do not transfect at all after i.m. injection, while weak signal was observed after s.c. injection.

Example 11: Administration of Replicon RNA by i.m. Versus i.d. Injections Into Mice Replicon-RNA, which encodes to luciferase enzyme, was dissolved in HBGx1 buffer or complexed in polyplexes, as described in example 2. These formulations were injected i.m. into the *Musculus tibialis* posterior muscles of Balb/c mice at doses of 2 µg of RNA. The mice were anasthsized by isoflurance 4, 7, and 10 days after the injections. Then, they were injected with luciferin substrate and the luminesence emission from the muscles was recorded by a CCD camera.

Figure 20:
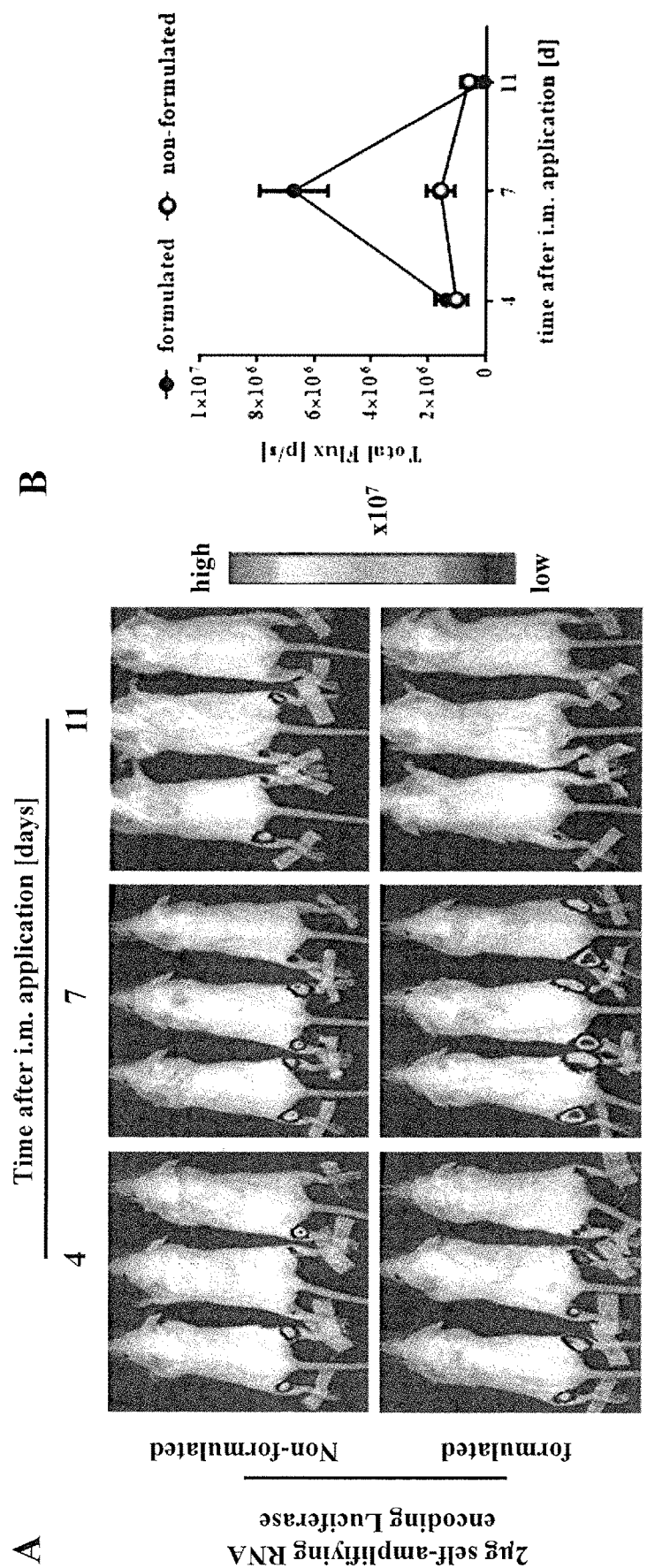
FIG. 20. A) Four, seven and eleven days after intramuscular (i.m.) application of 2 µg non-formulated (buffer solution) or formulated Replicon-RNA encoding Luciferase to both *Musculus tibialis* posterior of Balb/c mice, the animals were subjected to non-invasive in vivo bioluminescence imaging. Photons deriving from Luciferase protein were collected over one minute and are shown as an overlay with the photograph of the imaged mice. B) Graphical display of measured photons/second (p/s) at injection site.

Photons deriving from Luciferase protein were collected over one minute and are shown as an overlay with the photograph of the imaged mice (FIG. 20A). FIG. 20B shows a graphical display of measured photons/second (p/s) at injection site.

Figure 21:
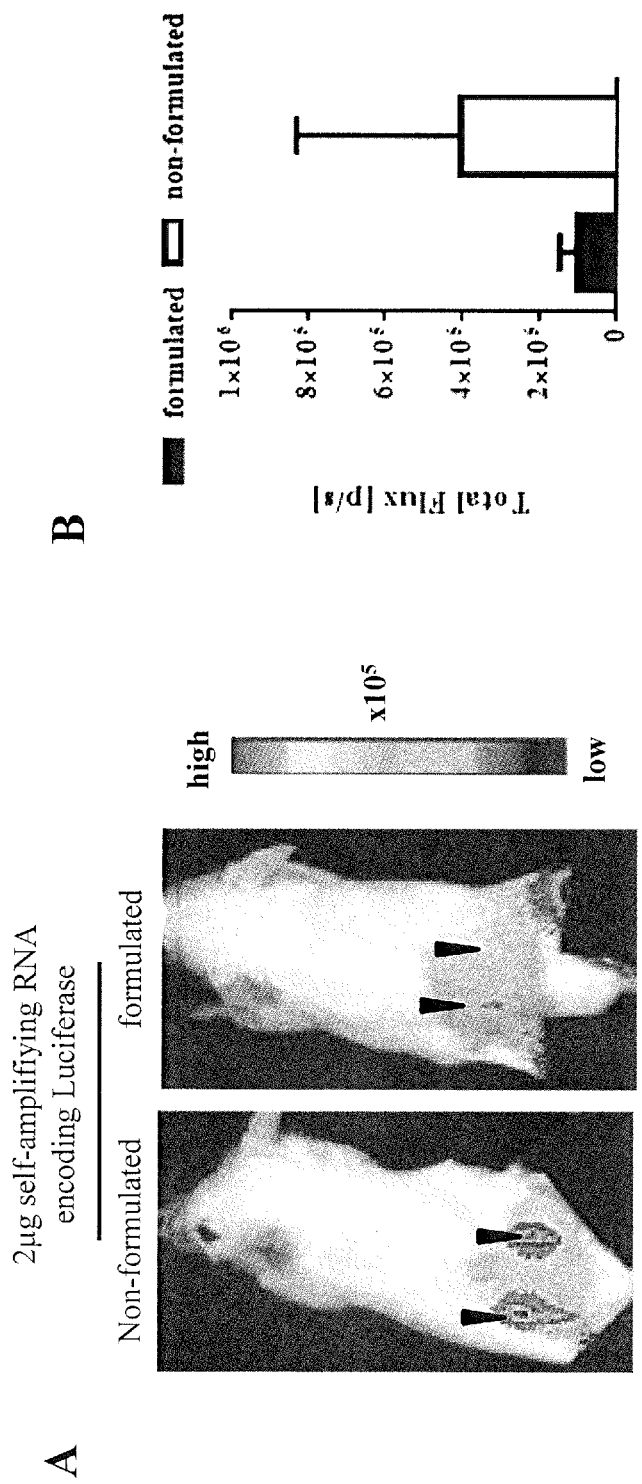
FIG. 21. A) Seven days after intradermal (i.d.) application of 2 µg non-formulated (buffer solution) or formulated Replicon-RNA encoding Luciferase to two injection sites at the dorsal skin of Balb/c mice, the animals were subjected to non-invasive in vivo bioluminescence imaging. Photons deriving from Luciferase protein were collected over one minute and are shown as an overlay with the photograph of the imaged mice. Black arrows indicate the site of injection. B) Graphical display of measured photons/second (p/s) at injection site.

Seven days after intradermal (i.d.) application of 2 µg non-formulated HBGx1) or formulated Replicon-RNA encoding Luciferase to two injection sites at the dorsal skin of Balb/c mice, the animals were subjected to non-invasive in vivo bioluminescence imaging. Photons deriving from Luciferase protein were collected over one minute and are shown as an overlay with the photograph of the imaged mice. Black arrows indicate the site of injection (FIG. 21A). FIG. 21B shows a graphical display of measured photons/second (p/s) at injection site.

Example 12: Beneficial Effect of RNA Formulation as a Vaccine

Figure 22:
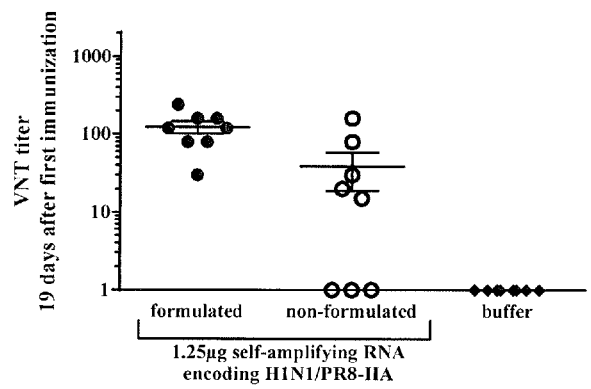
FIG. 22. Beneficial effect of Replicon-RNA formulation as a vaccine
Figure 22:
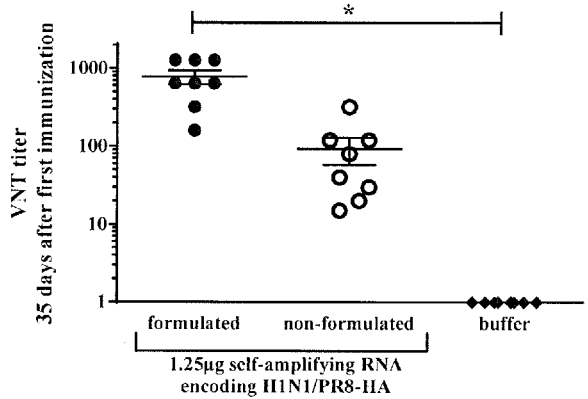
Figure 22:
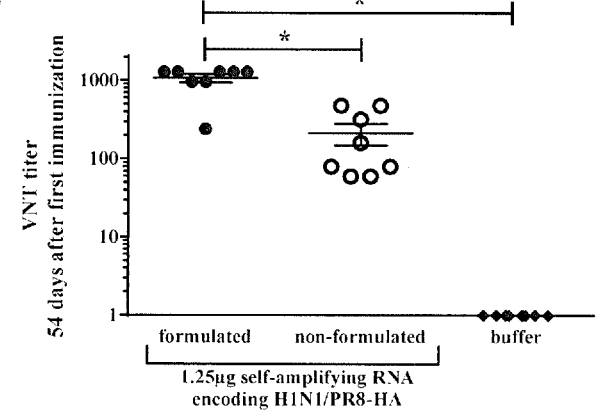
Figure 35:
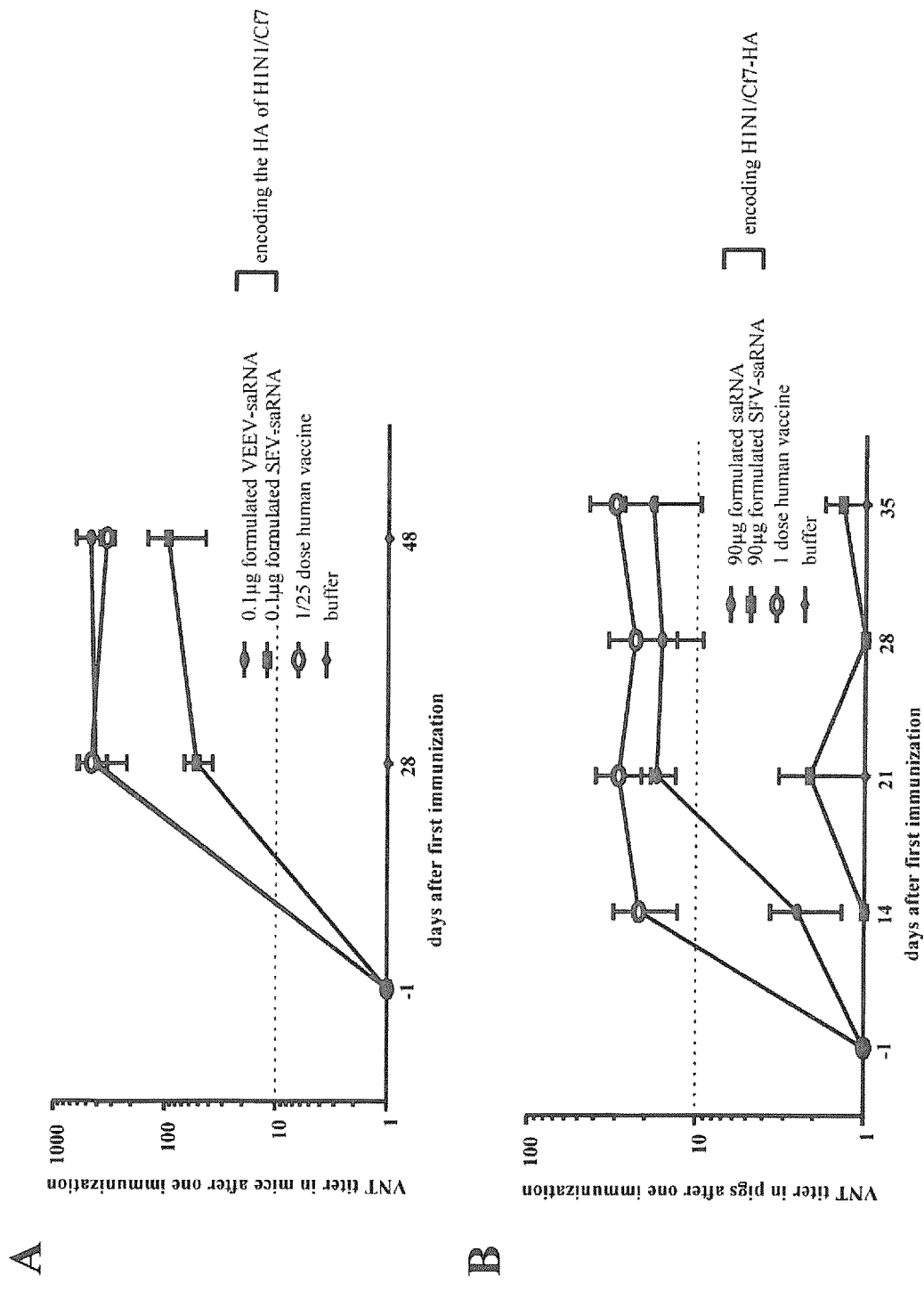
FIG. 35: Animals develop a neutralizing antibody immune response after intramuscular (i.m.) immunization with PEI-formulated self-amplifying RNA (saRNA) encoding the HA of the A/California/7/2009 (H1N1) virus (H1N1/Cf7-HA).

Mice were immunized twice at test day 0 and 21 with either a composition of the single stranded Replicon-RNA encoding the haemagglutinin (HA) of the H1N1 Influenza virus strain A/PuertoRico/8/1934 (H1N1/PR8) formulated with PEI with a N/P ratio of 11.6 a or the non-formulated single stranded RNA. All animals received a dose of 1.25 µg RNA. A third group received only saline as a buffer control group. As shown in FIG. 22A, 19 days after the first immunization and shortly before the second immunization, all animals that received the formulated RNA developed an immune response against the HA analyzed by virus neutralization assay (VNT, detection limit 1280). In contrast, only 5 out of 8 animals receiving the non-formulated RNA seroconverted against HA. As shown in FIG. 22B, 35 days after the first immunization, all RNA-receiving animals were positive for HA-specific antibodies and the antibody titers against the HA increased. Animal titers of the formulated RNA group but not the non-formulated RNA group became significantly higher compared to the saline control group. As shown in FIG. 22C, 54 days after immunization, mice that received 1.25 µg formulated RNA encoding the H1N1/PR8-HA developed a significantly higher antibody titer compared to animals that received 1.25 µg of the non-formulated RNA encoding the H1N1/PR8-HA (Significance was calculated using one-way ANOVA; * p≤0.001).

Figure 23:
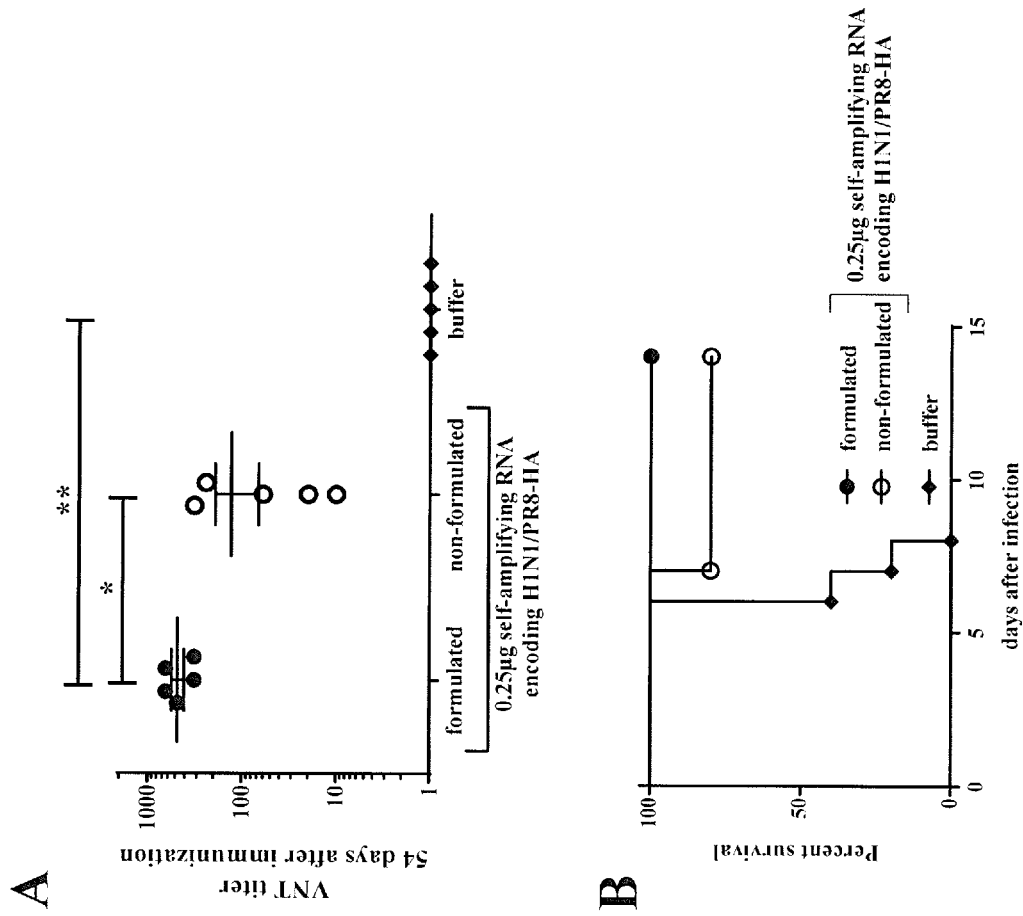
FIG. 23. Beneficial effect of Replicon-RNA formulation as a vaccine

Mice were immunized once at test day 0 with either a composition of the single stranded Replicon-RNA encoding the haemagglutinin (HA) of the H1N1 Influenza virus strain A/PuertoRico/8/1934 (H1N1/PR8) formulated with PEI with a specific N/P ratio of 11.6 a or the non-formulated single stranded RNA. All animals received 0.25 µg RNA. A third group received only saline as a buffer control group. As shown in FIG. 23A, 54 days after the immunization, all RNA-receiving animals were positive for HA-specific antibodies, titers of the formulated RNA group became significantly higher compared to the saline control group and to animals that received 0.25 µg of the non-formulated RNA encoding the H1N1/PR8-HA (Significance was calculated using one-way ANOVA; ** p≤0.001; * p≤0.05). 55 days after the immunization all mice were infected with a 10 fold median lethal dose ($MLD_{50}$) of H1N1/PR8. Survival was observed. As shown in FIG. 23B, all control animals died within 8 days. 4 out of 5 animals that received the non-formulated RNA encoding the H1N1/PR8-HA survived the challenge infection. In contrast, all mice receiving the formulated RNA encoding the H1N1/PR8-HA survived the challenge infection demonstrating the beneficial effect of RNA/polyalkyleneimine composition.

Example 13: Spray Drying of Replicon RNA Formulated with PEI

The formulation was prepared with a N:P ratio of 12 by following the pipet scheme given in Table 1 two times and subsequent combination of the obtained material. Thereby, 5.0 mL of replicon RNA polyplexes with a RNA concentration of 0.1 mg/mL RNA were obtained.

| Polymer mix: | | | RNA mix: | |
|---|---|---|---|---|
| HBT2X [µL] | wfi [µL] | jetPEI [µL] | RNA stock [µL] | HBT2X [µL] |
| 250 | 940 | 60 | 250 | 1000 |

Figure 24:
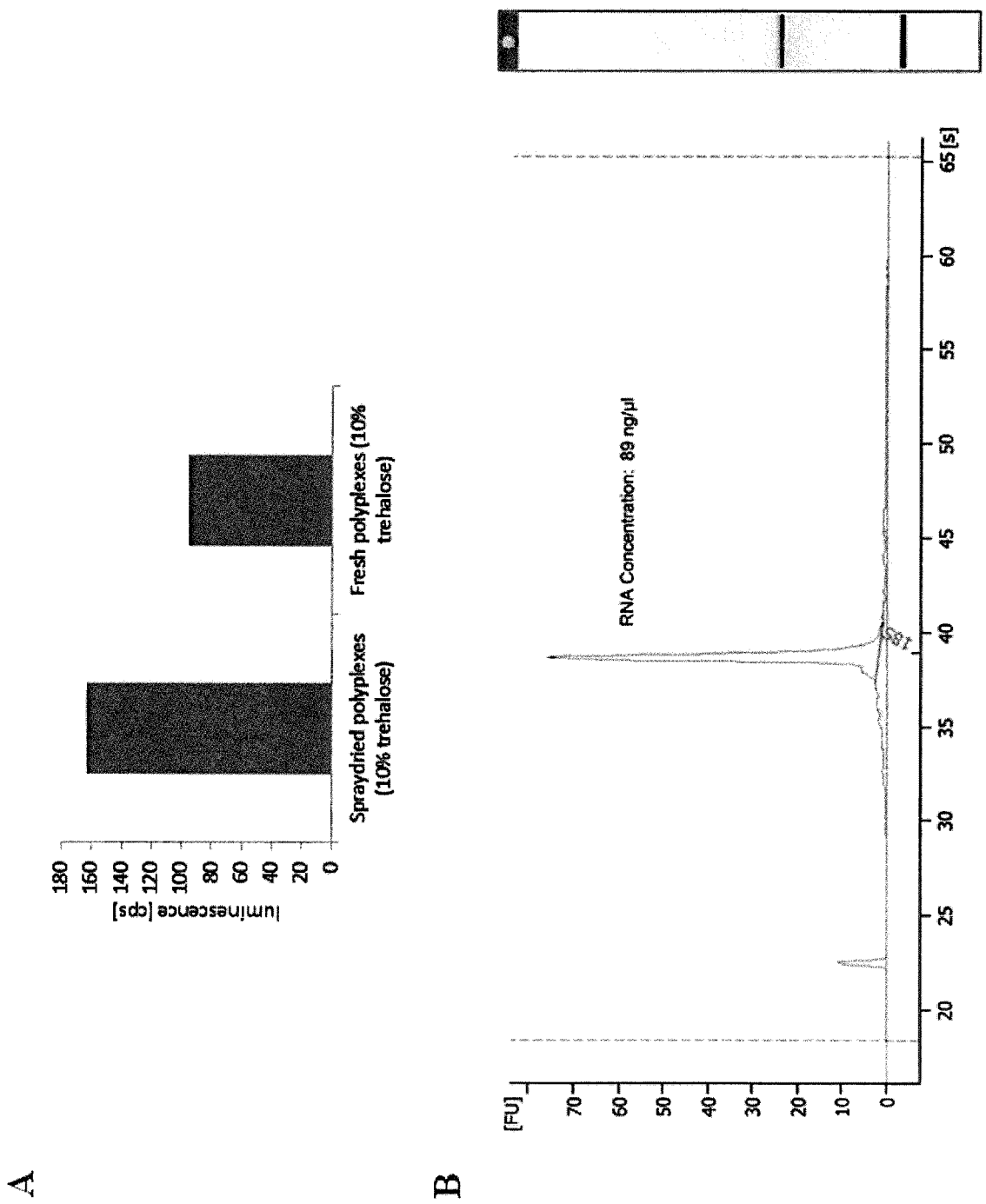
FIG. 24. Results from Spray drying of Replicon-RNA formulated with PEI in 10% (w:v) Trehalose FIG. 25. Normalized luminescence from C2C12 muscle cells after incubation with PEI/Replicon-RNA polyplexes at different N/P ratio, before (Prepared) and after (Sterilized) sterile filtration.

3.5 mL of this formulation were spray dried and 533 mg of material were collected (yield: 76.1%). The particle size of the freshly prepared replicon RNA polyplexes was not determined, as the material was discharged at the Büchi demo lab. The particle size (z-average) after reconstitution with water (mixture: 20 mg spray dried polyplexes and 200 µl wfi; resulting in 10 mM trehalose and a RNA concentration of 0.1 mg/mL) was 289 nm and the PDI was 0.238 (Nicomp, 15 minutes). FIG. 24A shows an in-vitro investigation of the luciferase expression of saRNA polyplexes after and before spray drying. The luciferase activity of the saRNA is not lost due to the spray drying process. Differences in the absolute height of the signals are due to the variances of the assay.

In an additional experiment, uncomplexed mRNA in 10% (w:v) trehalose was spray dried and the integrity of the mRNA after spray drying was investigated by capillary electrophoresis measurements.

2.50 mL Messenger RNA (R36-05.2-DP; c(RNA)=0.5 mg/mL; 10 mM Hepes; 0.1 mM EDTA; pH 7.0) were mixed with 2.50 mL 20% (w:v) Trehalose solution (volume ration of 1:1) resulting in the following composition: c(RNA)=0.25 mg/mL; 10% (w/v) Trehalose; 5 mM Hepes; 0.05 mM EDTA. During spray drying, the sample material was held on ice. In total, 2.5 mL of this solution was spray dried. During spray drying, the outlet temperature increased from 33 to 37° C. within ten minutes. In order to lower the temperature increase, the gas flow was increased from 98 to 101 L/min. During spray drying, the temperature further increased to 41° C. within the next 60 minutes. After complete spraying, 165 mg dried material were collected (yield: 66.0%). For analysis of RNA integrity, the material was dissolved in wfi (mixture: 20 mg spray dried RNA and 200 µl wfi; resulting in a Trehalose content of 10% and a RNA concentration of 0.25 mg/mL). The dissolved RNA was analyzed by using the Agilent 2100 Bioanalyzer. The results of these analysis are depicted as electropherogram of spray dried RNA in FIG. 24B.

It was demonstrated, that the integrity of the uncomplexed RNA was maintained, spray drying did not lead to measurable RNA degradation.

Spray drying experiments were performed as follows:

The Nano Spray Dryer B-90 from Büchi was used for spray drying of RNA containing formulations. For preparation of these formulations, the following compounds were used:

Messenger RNA (R36-05.2-DP, c(RNA)=0.5 mg/mL; 10 mM Hepes; 0.1 mM EDTA; pH 7.0)
Replicon RNA encoding for Luciferase (D2 RNA-A1310 29-01 pST1-SFV4-TRON-I2m2-A30L70, wfi, c(RNA)= 1 mg/mL)
Water for injection (wfi)
NaCl (1.5 M in wfi)
Trehalose 20% (w:v) in wfi (Pfanstiehl. Lot No: 35261A)
2× Hepes buffered Trehalose 20% (w:v) in wfi (Pfanstiehl. Lot No: 35261A, 20 mM Hepes)
JetPEI (Polyplus; Lot. Nr.: 13081A1S; 150 mM nitrogen)

For spray drying, the following process parameters were chosen:

Nozzle: 4 µm
Inlet temperature: 80° C.
Outlet temperature: 30° C.
Gas flow: 98 mL/min
Applied current: 15.000 V; 350 µA Prior to all experiments, the device is cleaned with RNAse Zapp and wiped with ethanol, and the cap was cleaned in an ultrasonic bath.

Example 14: Microfluididics for Polyplex Manufacturing

The NanoAssemblr™ (Precision Nanosystems, BC, Vancouver, Canada) with the Microfluidic Chip provided by the manufacturer (1029-036) was used. For the RNA, an in house manufactured Replicon RNA (Batch No. R071_1_2) was used. Polyethylenimine (Max PEI 40) was from Polysciences (Eppelheim, Germany). As Syringes BD Plastipak 1 ml; 1508006, BD Biosciences (Heidelberg, Germany) were used. The two components were mixed at a 1:1 ratio, using a flow rate of 12 ml/minute. Samples were prepared at two different concentrations, namely 50 mg/l and 250 mg/l.

For particle size measurements using dynamic light scattering, a 380 ZLS submicron particle/zeta potential analyzer from Nicomp (PSS Nicomp, Santa Barbara, CA) was used.

For each condition, 1.5 ml were manufactured. Samples were diluted with HBG buffer for size measurements.

Pipetting scheme was as follows:

| Preparation parameters | | | Stock solutions | | RNA tube | | PEI tube | | |
|---|---|---|---|---|---|---|---|---|---|
| Final volume (µl) | N/P ratio | Final RNA Conc. (mg/l) | RNA (g/l) | JetPEI (mM) | RNA (µl) | HBGx2 (µl) | JetPEI (µl) | HBGx2 (µl) | Water (µl) |
| 2000 | 12 | 50 | 2.6 | 106.9 | 38 | 962 | 33.6 | 38 | 927.9 |
| 2000 | 12 | 250 | 2.6 | 106.9 | 192 | 808 | 201.9 | 231 | 567.4 |

Microfluidic mixing experiments were performed using a device that comprises a Y-type microfluidic mixer where two components, which are provided in standard syringes, are mixed. The two components were mixed at a 1:1 ratio, using a constant flow rate of 12 ml/minute. Samples were prepared at two different concentrations, namely 50 mg/l and 250 mg/l, and particle sizes of the obtained polyplexes were measured.

Polyplexes were manufactured with microfluidic devices, demonstrating feasibility of continuous flow manufacturing for upscaling and GMP manufacturing. Particle formation was possible without problems, and no indication for aggregate formation or clogging was observed. Particle size was measured by dynamic light scattering. For polyplexes manufactured at 0.05 mg/l, the size was about 123 nm, and for particles manufactured at 0.25 mg/ml, the size was about 314 nm. Details of the obtained results are given in the table below.

| Concentration mg/ml | Size (nm) | PDI | ND | Channel Width |
|---|---|---|---|---|
| 0.05 | 122.8 | 0.31 | 167 | 17 |
| 0.25 | 314.2 | 0.247 | 116 | 45 |

All samples measured at a RNA conc. of 0.02 mg/ml (diluted with HBGx1)

The feasibility of polyplex manufacturing by microfluidics was demonstrated. Manufacturing was performed with a simple Y-type mixer, and no particular procedures, such as hydrodynamic focusing, were necessary in order to enable smooth manufacturing. Under suitable conditions, particles with a size well below 200 nm can be manufactured, enabling terminal sterile filtration with established and GMP compliant sterile filters. As no indication for aggregation or clogging was noted, it is concluded that upscaling to larger manufacturing batches will be possible without problems. Further options for upscaling comprise parallelization of several, identical devices. Summarizing, the results can be taken as an indication for the general feasibility of GMP compliant microfluidic manufacturing of PEI/RNA polyplexes.

Example 15: Sterilization of Polyplexes by Filtration

Polyplexes were prepared at Replicon-RNA concentration of 100 mg/L and N/P ratios of 11.5, 13.5 and 15.5, as previously described in the section "Stability studies of polyplexes".

Three tubes with 2.68 ml of polyplexes at three different N/P ratios were prepared. The polyplexes (1.34 ml) were filtrated through sterile Millex-GP Med Syringe Filter Units with pores of 220 nm (Cat. #SLMPL25SS, Merck Millipore).

The polyplexes were diluted to an RNA concentration 10 mg/L in HBGx1. Next, they were diluted to an RNA concentration of 5 mg/l in NaCl 0.9% 30 min before the addition to cells.

C2C12 cells were seeded in a 96-well plate (flat bottom) at a concentration of $2 \times 10^4$ cells per well. The cells were maintained at 37° C. and 7.5% $CO_2$. After 24 h, the supernatant was discarded and replaced with 50 µL of DMEM Medium (+10% FCS). Polyplexes were diluted (1:5) in DMEM medium with 10% FCS and pre-incubated for ~15 min. Then 50 µl of the polyplex solution was added to the cells to a final medium volume of 100 µl. After additional 48 h, Bright-Glo™ Luciferase assay (Cat. #E2610, Promega GmbH, Mannheim, Germany) was performed according to the manual of instruction.

In parallel to transfection also the cell number was measured using Cell proliferation Kit II (XTT. Roche, #11465015001). In both assays each polyplex-sample was tested in biological triplicates. As negative control, cells will be seeded without treatment ("untreated"). For the XTT-assay also medium without cells, equivalent to background (BG) were also seeded in triplicates. Finally, luminescence (Bright-Glo™) as well as absorbance (XTT) were measured with a "infinite 200pro" reader (Tecan). The normalized luminescence was calculated by dividing the luminescence signal by the absorbance (proportional to the cell number).

Figure 25:
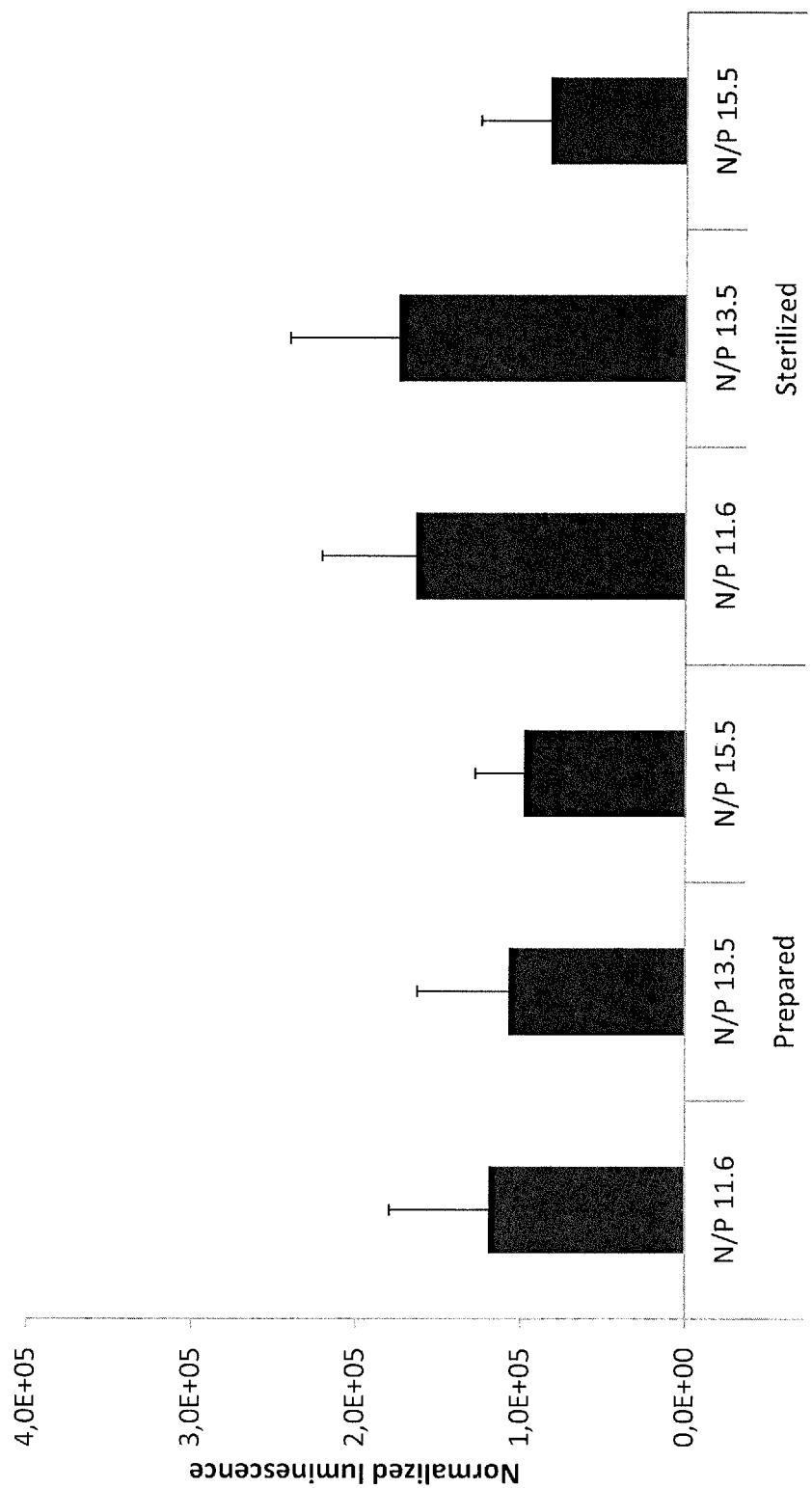

FIG. 25 shows the normalized luminescence from C2C12 muscle cells after incubation with PEI/Replicon-RNA polyplexes at different N/P ratios, before (Prepared) and after (Sterilized) sterile filtration.

It can be concluded that Syringe Filter Units are suitable for sterilization of polyplexes. The transfection efficacy of the polyplexes does not change due to the sterilization process.

Figure 26:
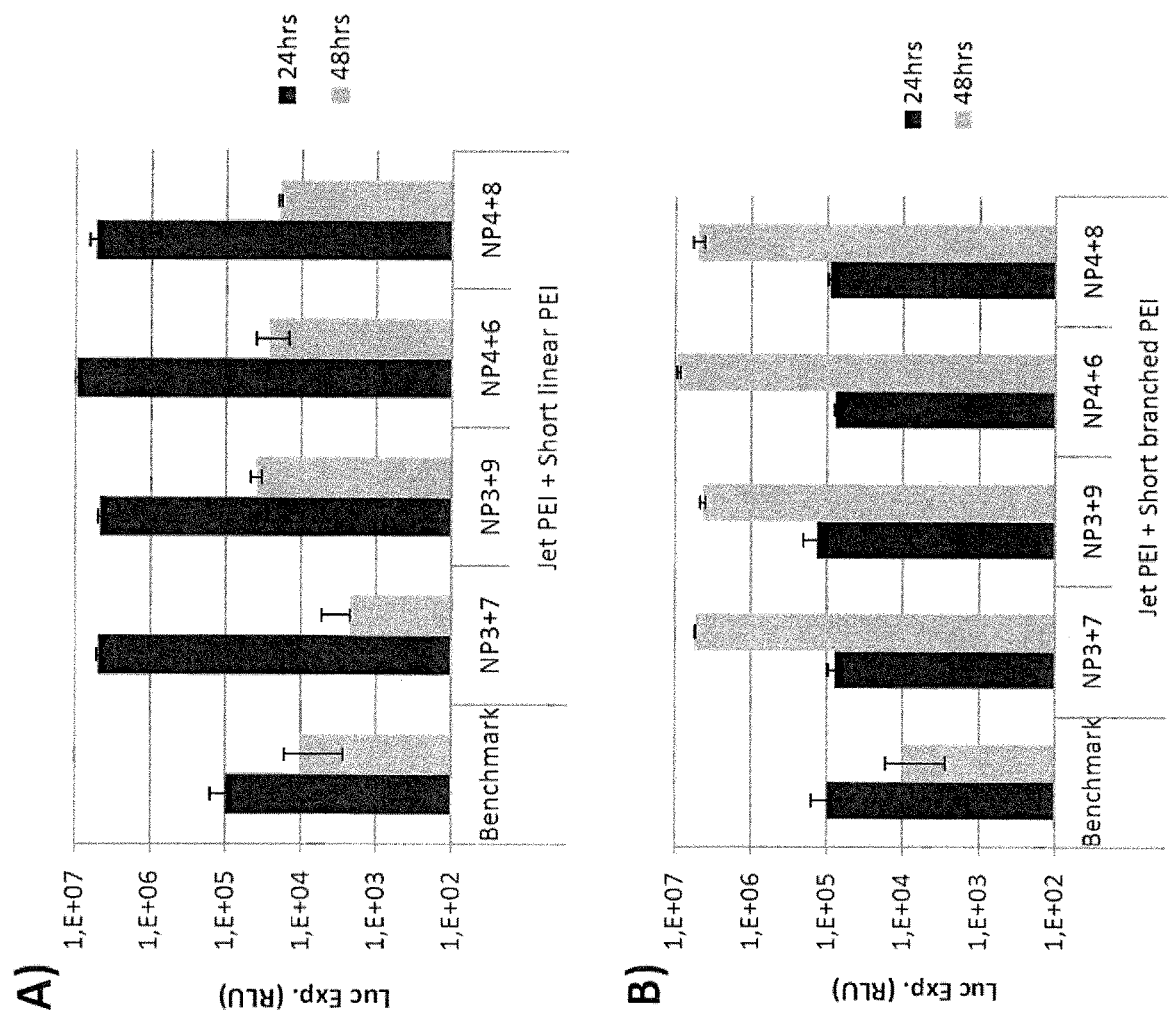
FIG. 26: Effect of combination of Short and Long PEI on transfection efficiency in vitro according to example 16.
Figure 27:
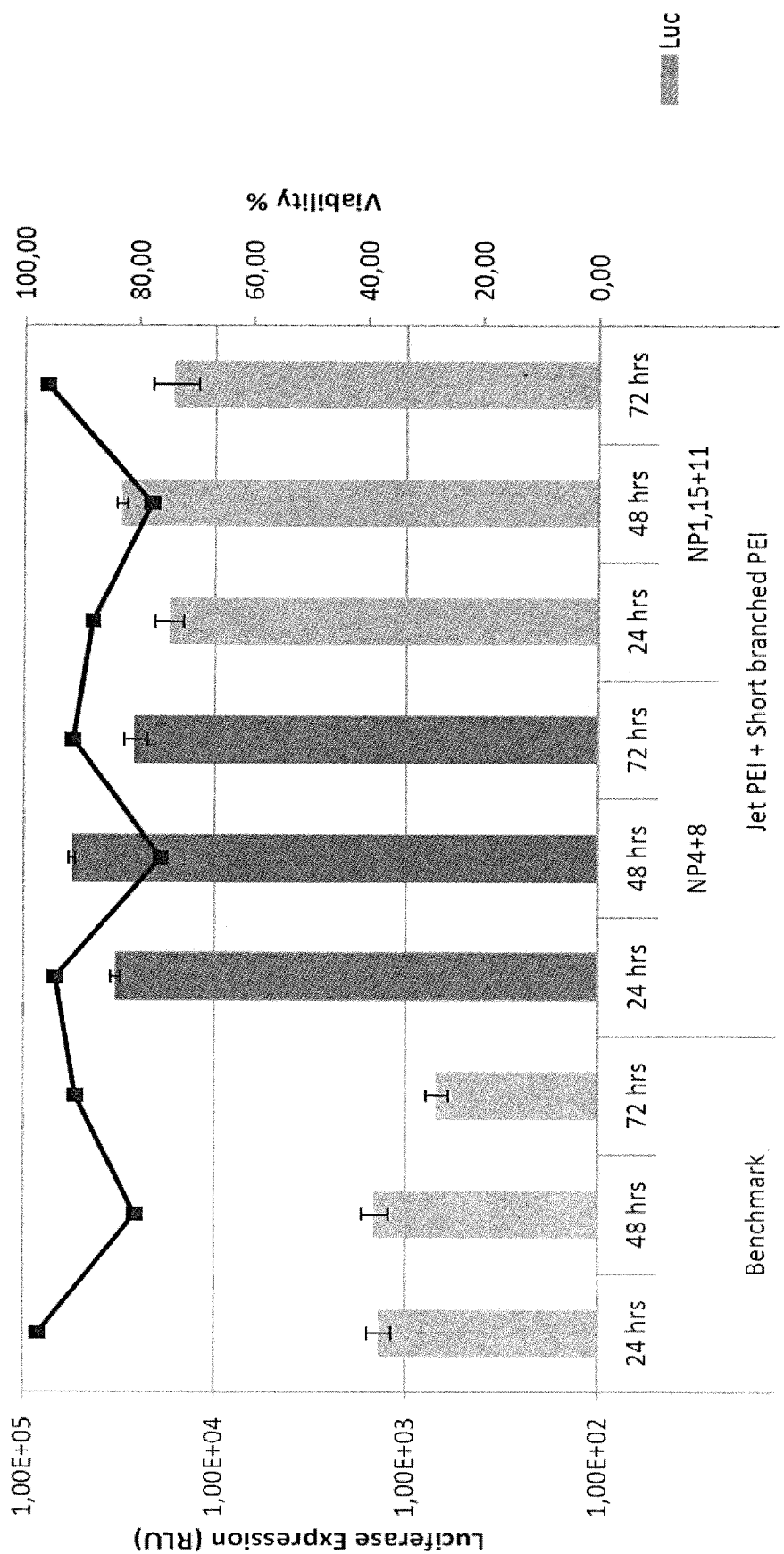
FIG. 27: Replicon-RNA Transfection efficacy of Long Jet PEI+Short PEI Polyplexes versus Benchmark (i.e. in vivo JetPEI NP12) according to example 17: Short PEI (branched 1.8 kDA) and Long PEI at different combinations (NP4+NP8 or NP1, 15+NP11) for a total NP of 12.

Example 16: Optimizing the Polyplex Transfection by Combinations of Short and Long PEI Luciferase encoding Replicon-RNA was complexed with a genuine combination of Short PEI between 0.6 and 11 kDA (e.g. either linear Short PEI 2.5 kDA or branched Short PEI 1.8 kDA) and Long PEI between 20 and 40 kDa (e.g. 22 kDa in vivo/Jet PEI) at different combinations for a total NP of 10 or 12 in MBG buffer (final concentration 5% w/v Glucose, 10 mM MES, pH 6.1). In vivo/Jet PEI NP12 alone was used as a benchmark. Complexation of Short and Long PEI polyplexes took place in two steps: In the first step, complexation of Replicon-RNA was adjusted for desired NP with in vivo/Jet PEI. In the second step, excess of Short PEI was added to the formulation to reach the desired total NP ratio; i.e. the first number defines the Long PEI NP and the second number the Short PEI (e.g. NP4+8=NP4 Long PEI and NP8 Short PEI). Luciferase assay were performed as previously described in Example 15. Results are shown in FIG. 26. FIG. 26 A) indicates transfection efficacy of Short linear PEI and Long in vivo Jet PEI polyplexes at 250 ng of RNA/well. FIG. 27 B) indicates transfection efficacy of Short branched PEI and Long in vivo Jet PEI polyplexes at 250 ng of RNA/well.

Conclusion: In comparison to the benchmark results with Long PEI (e.g. in vivo Jet PEI) only, the transfection efficacy can be significantly improved by using combinations of Long PEI and Short PEI.

Interestingly, with regard to combinations with linear Short PEI the luciferase expression signal peaked in the first 24 hours after transfection, whereas with regard to combinations with branched Short PEI the luciferase expression signal peaked in the first 48 hours after transfection. Thus, in situations where expression in a particular time frame is desired, careful selection of the right Short PEI/Long PEI combination is reasonable.

Example 17: Optimizing the Polyplex Transfection by Reducing the Amount of Long PEI Secreted nano-luciferase encoding Replicon-RNA was complexed with a genuine combination of Short PEI (e.g. branched 1.8 kDA) and Long PEI (e.g. in vivo/Jet PEI) at different combinations for a total NP of 12 in MBG buffer (final concentration 5% w/v Glucose, 10 mM MES, pH 6.1). In vivo/Jet PEI NP12 was used as a benchmark. Complexation of Short+Long PEI polyplexes took place in two stets: In the first step, complexation of replicon-RNA was adjusted for desired NP with in vivo/Jet PEI. In the second step, excess of short PEI was added to the formulation to reach the desired total NP ratio; i.e. the first number defines the Long PEI NP and the second number the Short PEI (e.g. NP4+8=NP4 Long PEI and NP8 Short PEI). Secreted Luciferase was measured according to manufacturer protocol (Nano-GLO, Promega, USA) at 125 ng or RNA/well. Cell viability assays were performed as previously described in Example 15.

Results are shown in FIG. 27. Compared to the benchmark and for the same total NP ratio, higher expression levels were achieved with combinations, e.g. NP4+8 and NP1.15+11. Thus, Transfection efficacy can be significantly increased by reducing the concentration of long PEI in the formulation and increasing the concentration of less toxic Short PEI (e.g. branched 1.8 kDa).

Example 18: Effect of Salt Variations and/or pH on Transfection Efficiency In Vivo BALB/c mice were purchased from Janvier Laboratories and implemented in the experiment at an age of eight weeks. Prior injection of indicated test items, mice were subjected to isoflurane anesthesia and fur removed from hind legs using an electric razor. Subsequently, Replicon-RNA (saRNA)-PEI-polyplexes (e.g. saRNA-in vivo Jet PEI Polyplexes NP12) at a RNA dose of 2 µg were intramuscularly applied in 20 µL total volume to each *Musculus tibialis* posterior of three mice per group. The formulations varied with respect to pH and/or salt concentrations (e.g. NaCl). At indicated time points mice were intraperitoneally injected with D-Luciferin solution (100 mg/kg body weight) and bioluminescence captured non-invasively in isoflurane anesthesised mice for 1 min via IVIS® Spectrum Device (Perkin Elmer). Graphs display photons per second [p/s] of bioluminescence signal determined via Living Image® software (Perkin Elmer) in a manually defined region of interest (ROIs) with regard to muscle of mice (injection sites) in these pictures with a total of six values/group.

Figure 28:
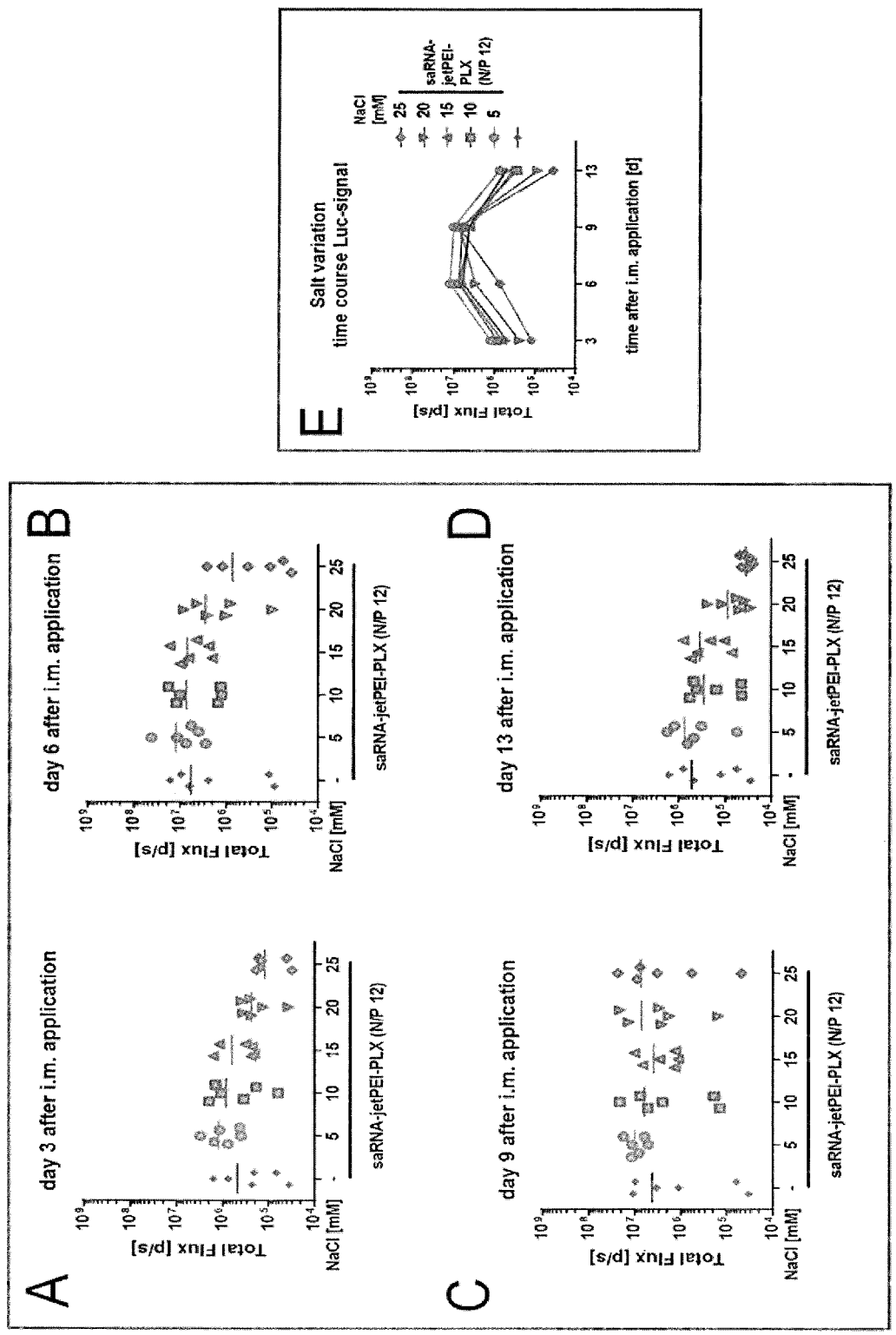
FIG. 28: Effect of salt variations (e.g. NaCl) on Replicon (saRNA)-RNA transfection efficiency in vivo according to example 18. Bioluminescence signals were detected at day 3 (FIG. 28A), 6 (FIG. 28B), 9 (FIG. 28C) and 13 (FIG. 28D). Signal strength was compared in FIG. 28E. The most intense signal in muscle region of mice could be detected at day 6 after i.m. injection in mice receiving PEI-Replicon-RNA polyplexes (e.g. Long PEI N/P 12) and addition of low concentrations (5 to 10 mM) salt.

The effect of salt variations (e.g. NaCl) on the transfection efficiency is shown in FIG. 28. Intramuscular injections of Replicon-RNA-PEI polyplexes at different N/P ratios led to long enduring bioluminescence signals in muscle region of mice after measurement at days 3, 6, 9 and 13. The detected signal strength increased from day 3 to day 6 (peak) after application but was detectable even at day 13. The most intense signal in muscle region of mice could be detected at day 6 after i.m. injection in mice receiving Replicon-RNA-PEI polyplexes (e.g. Long PEI N/P 12) and addition of low concentrations (5 to 10 mM) salt.

Figure 29:
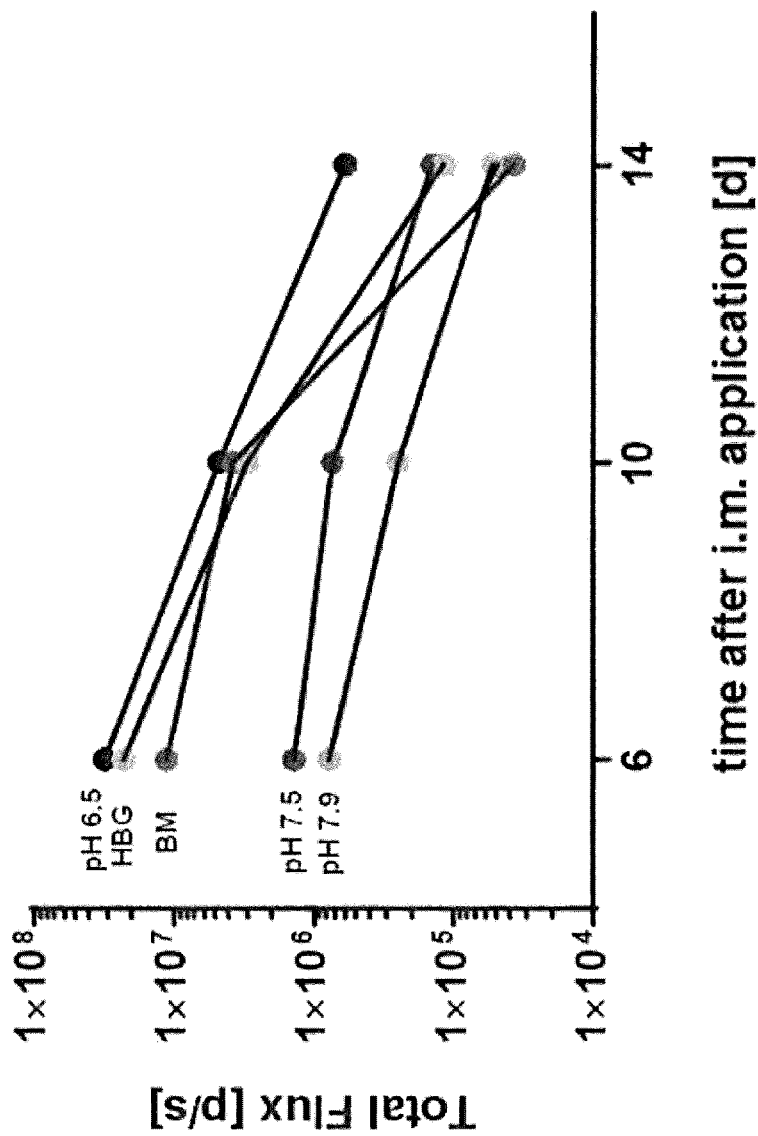
FIG. 29: Effect of pH adjustments on transfection efficiency of Replicon (saRNA)-PEI formulations according to example 18. Good results were obtained with saRNA-PEI polyplex formulations having pH values between 6.5 and 7.1. The most intense signal could be detected with a saRNA-long PEI NP12 formulation adjusted to pH 6.5. As benchmarks, saRNA-Jet PEI Polyplexes NP12 with unadjusted pH (BM) or HBG (20 mM Hepes, pH 7.4, 5 wt. % glucose) were used.

The effect of pH variations on the transfection efficiency is shown in FIG. 29. Good results were obtained with Replicon RNA (saRNA)-PEI polyplex formulations having pH values between 6.5 and 7.1, preferably between 6.5 and 6.9. The most intense signal could be detected with a Replicon-RNA-Long PEI NP12 formulation adjusted to pH 6.5. As benchmarks, Replicon-RNA-Jet PEI Polyplexes NP12 with unadjusted pH (BM) or HBG (20 mM HEPES, pH 7.4, 5 wt. % glucose) were used.

Example 19: pH Dependent Effects on the Electrophoretic Mobility and Transfection Efficiency of PEI Polyplexes In Vitro Luciferase encoding Replicon-RNA was complexed with Long PEI (e.g. in vivo jet PEI) at a N/P ratio of 4 in HBG buffer (final concentration 4.5% w/v Glucose, 10 mM HEPES, pH 7.1) at room temperature for 15 minutes and aliquoted in 11 samples. The pH of the samples was adjusted by the addition of HCl or NaOH depending on the final bulk pH to be tested. Measurement of electrophoretic mobility (p) was performed as described in Example 5. In vitro transfection of C2C12 mouse muscle cells, luciferase and cell viability assays were performed as previously described in Example 15.

Figure 30:
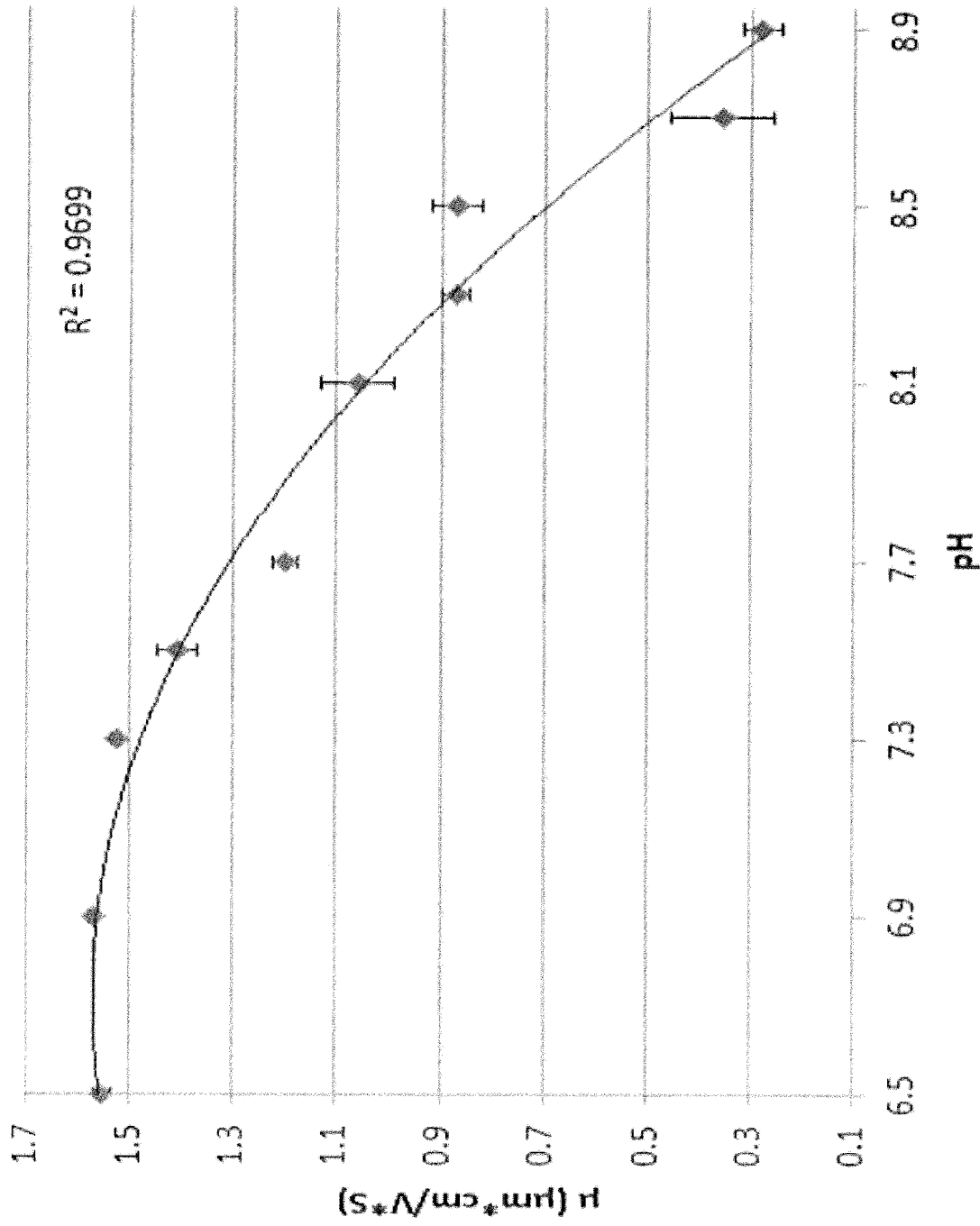
FIG. 30: Electrophoretic mobility of in vivo jetPEI/Replicon-RNA polyplexes (N/P 4) adjusted to different pH values according to example 19.
Figure 31:
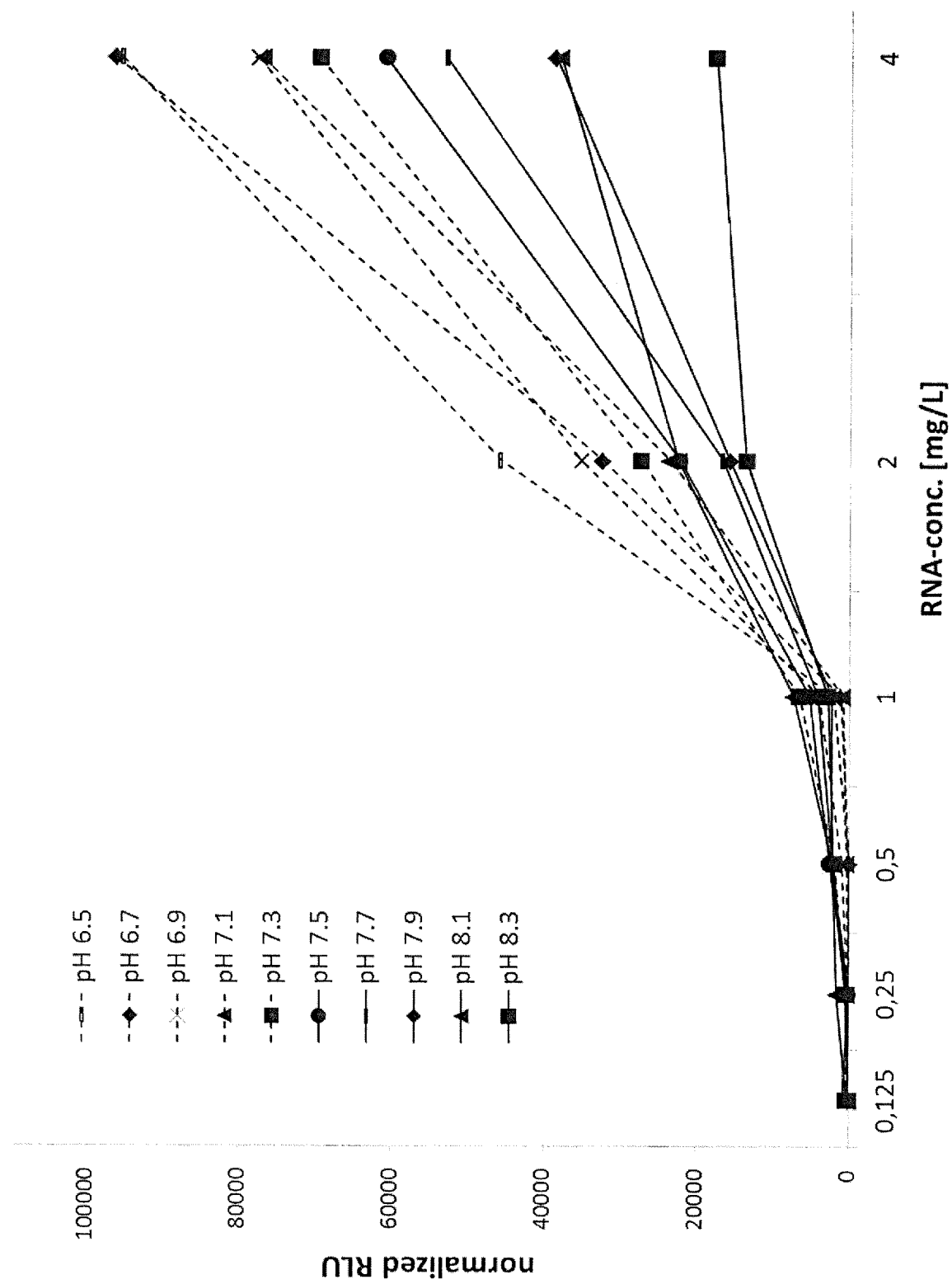
FIG. 31: Normalized luminescence from C2C12 muscle cells after incubation with different dosages of in vivo jetPEI/Replicon-RNA polyplexes at a N/P ratio of 4 and different pH values (pH 6.5-pH 8.5) according to example 19.

The pH dependent effects on the electrophoretic mobility and transfection efficiency of PEI polyplexes in vitro are shown in FIGS. 30 and 31. FIG. 30 indicates the electrophoretic mobility of in vivo jetPEI/Replicon-RNA polyplexes (N/P 4) adjusted to different pH values. FIG. 31 shows the normalized luminescence from C2C12 muscle cells after incubation with different dosages of in vivo jetPEI/Replicon-RNA polyplexes at a N/P ratio of 4 and different pH values (pH 6.5-pH 8.5).

The electrophoretic mobility of the polyplexes negatively correlated with the pH. Neutral polyplexes are obtained at approx. pH 8.9. Increasing the positive charge density on PEI polyplexes by reducing the bulk pH of the polyplex, preferably to pH values between 6.5 and 7.1, resulted in a higher transfection efficiency of C2C12 cells without affecting the cell viability. PEI polymers contain primary and secondary amines, whose protonation state depends on the bulk pH. Therefore, the results suggest an efficient way to control the charge of the polyplexes and their transfection efficiency by adjusting and optimizing the bulk pH.

Example 20: Influence of Positive Charge Excess in Long PEI Formulations

Secreted nano-luciferase encoding Replicon-RNA was complexed in different NP ratios between 2-12 in MBG buffer (final concentration 5% w/v Glucose, 10 mM MES, pH 6.1). Secreted Luciferase is measured according to manufacturer protocol (Nano-GLO, Promega, USA) at 125 ng or RNA/well. Excess of positive charges is calculated based on the Long PEI (i.e. in vivo/Jet PEI)-Replicon RNA NP ratio and the exact NP ratio at which total complexation takes places for this replicon-RNA & in vivo Jet PEI. Difference between used NP ratio and know NP ratio for total complexation allows calculation of the excess of positive charges in the formulation.

Figure 32:
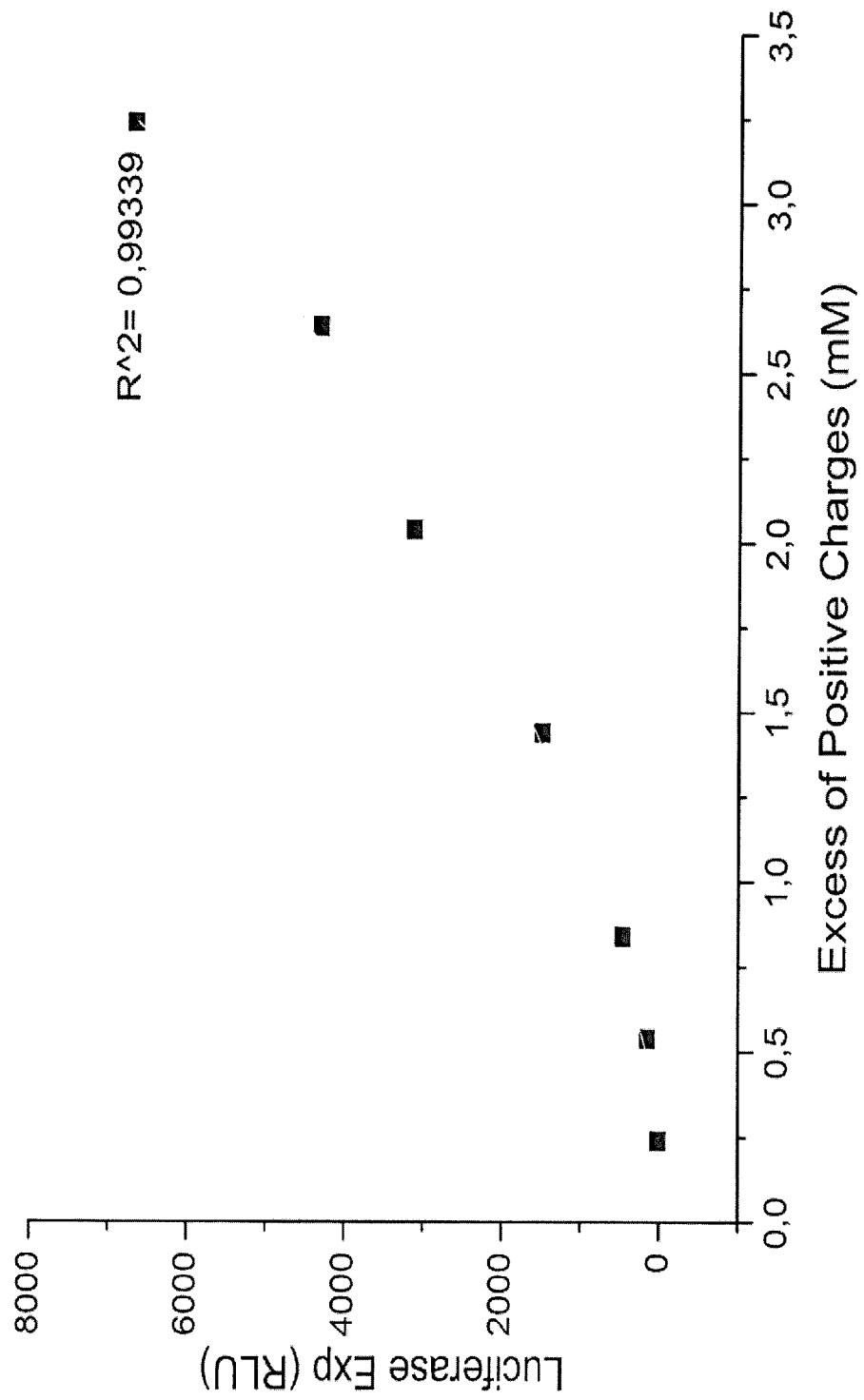
FIG. 32: Luciferase expression after transfection with different amounts of PEI/excess of positive charges in PEI formulations according to example 20.

As an example, results relating to transfection with in vivo Jet PEI polyplexes at 250 ng of RNA are shown in FIG. 32. In general, increasing the concentration of positive charges in the formulation is exponentially proportional to the luciferase expression level. Excess of positive charges up to 30 nM by increasing the amount of PEI has been proven to be beneficial.

Example 21: Optimizing the One Component PEI Polyplex Transfection by Using 2-Step Complexation If only one PEI variant (such as e.g. Long PEI) is used, transfection efficiency can be improved by using a 2-step complexation method. Secreted nano-luciferase encoding Replicon-RNA was complexed in two steps for a total NP of 12 in MBG buffer (final concentration 5% w/v Glucose, 10 mM MES, pH 6.1). In vivo/Jet PEI NP12 1-Step complexation was used as a benchmark. For example, complexation in 2 steps using in vivo Jet PEI took place as follows: In the first step, complexation of replicon-RNA was adjusted for desired initial NP. In the second step, excess of in vivo/Jet PEI was added to the formulation to reach the desired total NP ratio; i.e. the first number defines the initial PEI NP and the second number the excess of given in vivo Jet PEI on the second step (e.g. NP4+8: NP4 Jet PEI in first step and NP8 Jet PEI in second step). Secreted Luciferase was measured according to manufacturer protocol (Nano-GLO, Promega, USA) at 125 ng or RNA/well. Cell viability assay were performed as previously described in Example 15.

Figure 33:
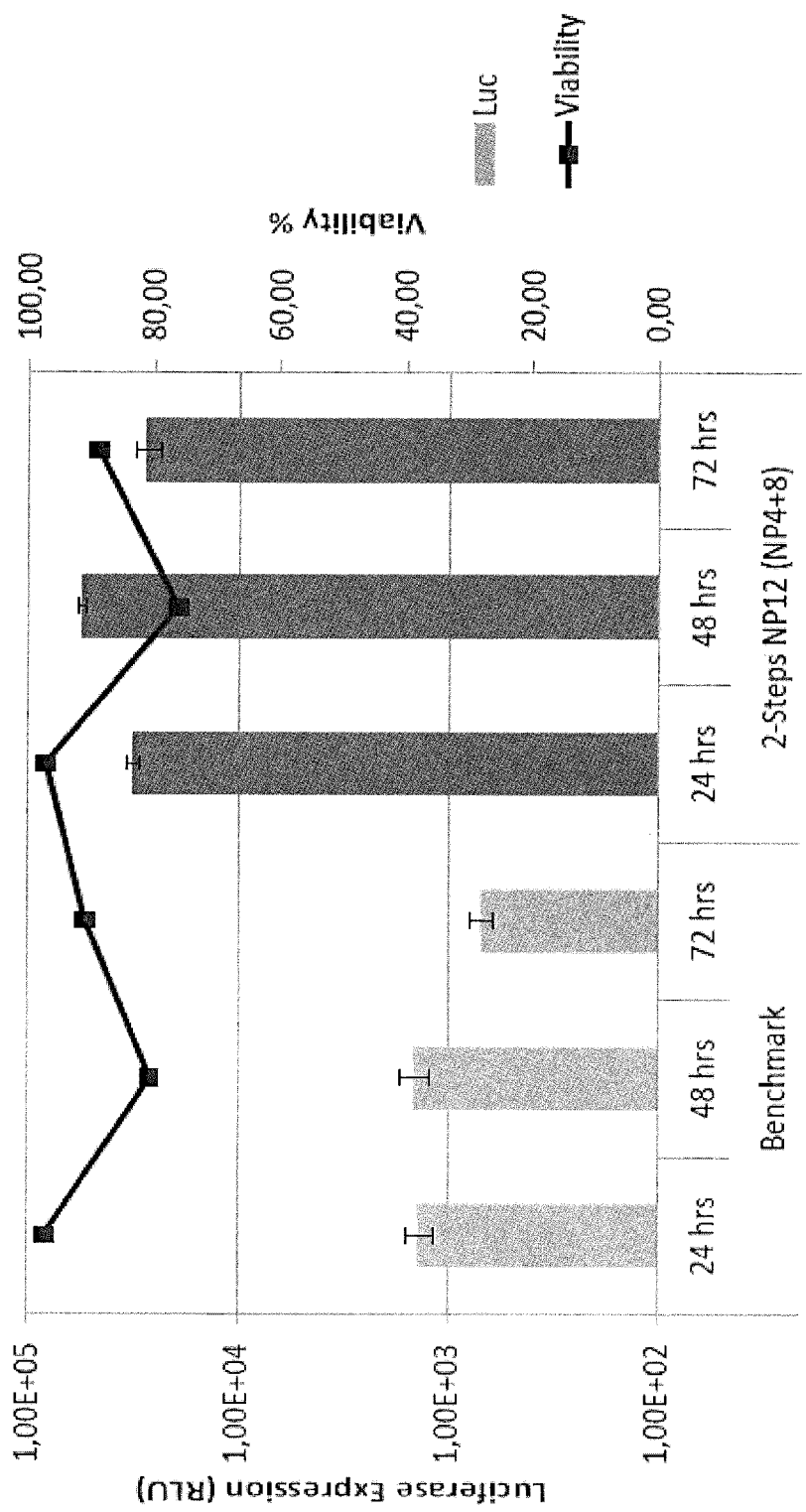
FIG. 33: Optimizing the polyplex transfection by using 2-Step complexation according to example 21.

Results of 2 step complexation are shown in FIG. 33. Compared to the vivo/Jet PEI NP12 1-Step complexation benchmark and for the same total NP ratio, higher expression levels were achieved with two steps complexation.

Example 22: Effect of Polyplex Formulation Buffer on Immunization Efficiency saRNA was formulated into polyplexes by using In vivo-jetPEI. Polyplexes were produced by using Hepes-buffered glucose (HBG) or MES-buffered glucose (MBG) (5% D-Glucose, 10 mM MES, pH 6.1). Mice were immunized i.m. at d0 in a one shot experiment. Serum was collected at d45 after immunization and the amount of Cf07-HA specific antibodies in the serum was analyzed using HA-specific ELISA. Endpoint titration of serumdilutions has been performed and the area under the curve (AUC) was determined. Percentage increase in area under the curve of MBG-produced polyplexes is depicted compared to HBG-produced polyplexes set as 100%.

Figure 34:
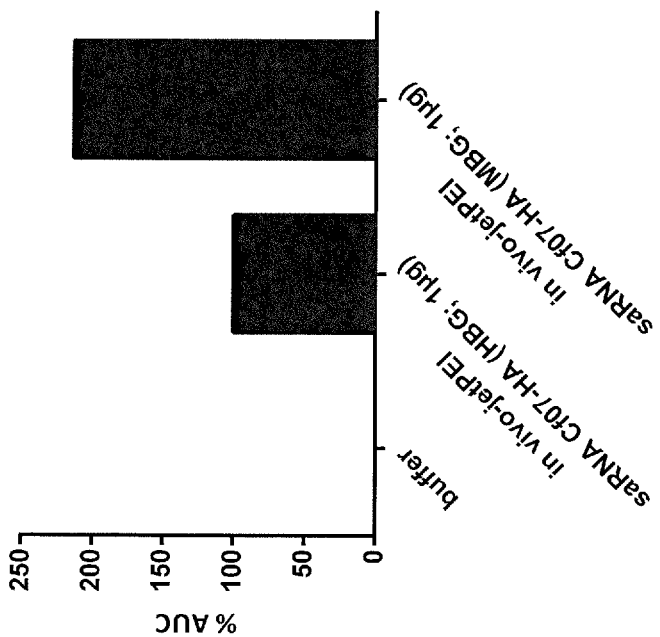
FIG. 34: Immunization experiment according to example 22 showing the superior effect of saRNA-polyplexes formulated with MES-buffered glucose (MBG) in comparison to HEPES-buffered glucose (HBG).
Figure 34:
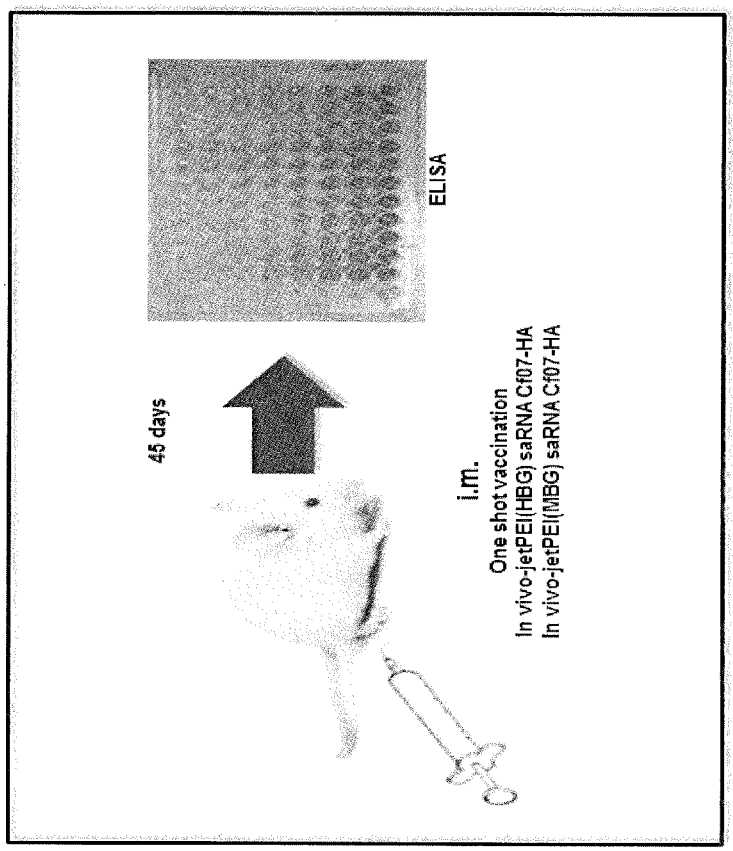

Results are shown in FIG. 34. In comparison to polyplexes formulated with HBG, polyplexes produced by using MES-buffered glucose generate a much higher ELISA signal after one shot vaccination of mice.

Example 23: Animals Develop a Neutralizing Antibody Immune Response After Intramuscular (i.m.) Immunization with PEI-Formulated Self-Amplifying RNA (saRNA) Encoding the HA of the A/California/7/2009 (H1N1) Virus (H1N1/Cf7-HA)

BALB/c mice were immunized once at day 0 with buffer, 1/25 dose of human vaccine or 0.1 µg of PEI-formulated VEEV-saRNA or SFV-saRNA encoding the H1N1/Cf7-HA in a N/P ratio of 12/1. 28 and 48 days later, animals were bled and serum was analyzed for antibody against the HA measured by virus neutralization assay (VNT; n=4). The results are shown in FIG. 35(A).

Domestic piglets were immunized once at day 0 with buffer, 1 dose of human vaccine or 90 µg of PEI-formulated VEEV-saRNA or SFV-saRNA encoding the H1N1/Cf7-HA in a N/P ratio of 12/1. The pigs were bled at day 14, 21, 28 and 35 after immunization to analyze the neutralizing antibody immune response against the HA performing the VNT (n=8; buffer group n=4). The results are shown in FIG. 35(B).

Group of animals receiving the formulated VEEV-saRNA vaccine developed a similar immune response to animals that were injected with the positive control. SFV-saRNA also led to a development of neutralizing antibody immune response, but to lower titers than after VEEV-saRNA immunization. Mean±SEM are shown in the graph.

Example 24: Animals Develop an Antibody Immune Response After Intramuscular (i.m.) Immunization with PEI-Formulated Self-Amplifying RNA (saRNA) Encoding the Porcine Circovirus 2 (PCV2)-Cap EU Protein BALB/c mice were immunized twice at day 0 and day 35 with buffer, 1 µg of PEI-formulated SFV-saRNA or VEEV-saRNA encoding the PCV2-cap_EU in a N/P ratio of 12/1. At day 14, 34 and 56 animals were bled and sera were analyzed for antibodies against the PCV2-cap as determined by a commercially available ELISA assay (INgezim Circo IgG, Ingenasa; n=4).

As shown in FIG. 36, groups of animals receiving the formulated SFV- or VEEV-saRNA vaccines developed a similar antibody response against the PCV2-cap_EU protein. The antibody immune response after a single vaccination with SFV-saRNA was slightly higher than for VEEV-saRNA. After two immunizations, the antibody response was nearly identical for both types of saRNA vaccines. Mean±SEM are shown in the graph.

Example 25: Effect of pH on Stability of Self-Amplifying RNA (saRNA)

Replicon-RNA (saRNA) was complexed at N/P12 in different buffer systems and pH conditions. Both types of buffers, acetate or MES buffer, contained a final concentration of 10 mM of the buffering agent and a final concentration of 5% w/v D-Glucose. saRNA/PEI-Polyplexes were stored in the respective buffer at 4° C. for different time periods (1, 2, 4 and 8 days after complexation). Upon complexation of the different formulations, RNA Integrity was directly measured (t=0). RNA Integrity was measured trough capillary electrophoresis. The complexed saRNA in polyplexes can be released after 20 min incubation at RT with a strong excess of a polyanion that induces electrostatic interaction with the polymer, releasing the RNA enclosed in the polyplexes. 200 ug of released RNA are used strictly following the protocol provided with the appropriate kit (Standard Sensitivity RNA Analysis Kit DF471) for the capillary electrophoresis assay. For each time point, reference RNA was used for quantification of the saRNA integrity.

As shown in FIG. 37, higher pH values in the formulation buffer lead to significantly increased degradation of the saRNA. The lowest integrity loss of saRNA upon complexation was reached at pH 4 with acetate buffer.

Example 26: PEI-Formulated saRNA-VEEV Encoding the HA of A/California/7/2009 (H1N1; Cf7/HA) Induces a Strong and Longer Lasting Antibody Response Compared to Commercial Vaccine, but Additionally Induces a Strong T Cell Response Which Protein Based Vaccines Lack to Induce In FIG. 38, BALB/c mice were immunized i.m. twice at day 0 and day 35 (in the graphs, indicated by arrows) with either buffer (black symbols), 20 µL of a human licensed vaccine against seasonal influenza virus strains (Begripal 2016/2017; hLIC; grey symbols) or 0.5 µg of PEI-formulated VEEV-saRNA based vaccine encoding for the Cf7/HA (dark grey symbols). At different time points, mice were sacrificed and A) splenocytes were collected to perform Cf7/HA-specific ELISpot assays with the single cell suspension. For the ELISpot analysis, different CF7/HA specific peptide pools were used to stimulate $CD8^+$ T cell (left) or $CD4^+$ T cell (right) response measured by IFNy secretion. Additionally, serum samples were collected to perform B) anti-Cf4/HA specific Virus neutralization assay to serum antibodies for their functionality to inhibit viral cell infection. Note that for the serological analysis, A/California/4/2009 (H1N1; Cf4) virus was utilized; data indicate mean±SEM (buffer group n=3; vaccine groups n=4).

List of Abbreviations and Definitions

ATM atmospheric pressure
C Concentration
CSS a solution of $CuSO_4$ 23 mg in 100 ml of NaAcetate 0.1M, pH 5.4
DLS Dynamic light scattering
EDTA Ethylenediaminetetraacetic acid
FCS Fetal calf serum
h hours
HBGx1 HEPES 10 mM buffered (pH 7.1) glucose 5%
HBGx2 HEPES 20 mM buffered (pH 7.1) glucose 10%
HBTx1 HEPES 10 mM buffered (pH 7.1) trehalose 10%
HBTx2 HEPES 20 mM buffered (pH 7.1) trehalose 20%
HBTx1+EDTA HEPES 2.8 mM buffered (pH 7.1) trehalose 10% with EDTA 80 µM
HEPES 4-(2-hydroxyethyl)-1-piperazineethanesulfonic acid
IVI Institute of Virology and immunology, Mittelhäusern, Switzerland
IVT in-vitro transcribed mRNA
kDa 1000 Daltons
Lyo Lyophilization min minutes
MBGx1 5% D-Glucose, 10 mM MES, pH 6.1
MES 2-(N-morpholino)ethanesulfonic acid
N/P the ratio between the number of amine groups in PEI and phosphate groups in RNA.
PEI Polyethyleneimine
RNA Ribonucleic acid
UV Ultraviolet

The invention claimed is:

1. An injectable pharmaceutical composition comprising:
(a) single stranded, self-replicating RNA encoding a peptide or protein comprising an antigen or epitope, wherein the single stranded, self-replicating RNA is derived from Venezuelan equine encephalitis virus (VEEV) or from Semliki Forest virus (SFV); and
(b) polyethyleneimine
wherein the injectable pharmaceutical is adapted for intramuscular administration, and wherein the single stranded, self-replicating RNA is in an amount effective to elicit an immune response.

2. The composition according to claim 1, wherein the injectable pharmaceutical composition is adapted for administration to muscle cells or muscle tissue.

3. The composition according to claim 1, wherein the molar ratio of the number of nitrogen atoms (N) in the polyethyleneimine to the number of phosphor atoms (P) in the single stranded RNA (N:P ratio) is 2.0 to 15.0.

4. The composition according to claim 1, wherein the ionic strength is 50 mM or less.

5. The composition according to claim 1, wherein the single stranded, self-replicating RNA is a cis-replicon.

6. The composition according to claim 1, wherein:
when the single stranded, self-replicating RNA is derived from VEEV, the single stranded, self-replicating RNA corresponds or corresponds essentially to the genomic RNA of VEEV or an attenuated form thereof, wherein the open reading frame encoding structural proteins is replaced by an open reading frame encoding the peptide or protein comprising an antigen or epitope,
wherein the antigen or the peptide or protein comprising an antigen or epitope is a membrane protein comprising a Type I transmembrane protein, a Type II transmembrane protein, a Multipass transmembrane protein, a Lipid chain anchored membrane protein, a GPI-anchored membrane protein, a Peripheral membrane protein, or a viral envelope protein, and/or
wherein the antigen is Influenza hemagglutinin; or
when the single stranded, self-replicating RNA is derived from SFV, the single stranded, self-replicating RNA corresponds or corresponds essentially to the genomic RNA of SFV or an attenuated form thereof, wherein the open reading frame encoding structural proteins is replaced by an open reading frame encoding the peptide or protein comprising an antigen or epitope,
wherein the antigen or the peptide or protein comprising an antigen or epitope is not a membrane protein, and/or
wherein the antigen is a virus antigen comprising a protein from a virus surface protein comprising a membrane-bound glycoprotein, a viral capsid protein or a spike protein.

7. The composition according to claim 1, wherein the single stranded RNA and the polyethyleneimine are present in polyplex particles.

8. The composition according to claim 1, wherein the polyethyleneimine comprises the following general formula (I):

$$-\!\!\left[\!\!\begin{array}{c}N-(CH_2)_n\\|\\R\end{array}\!\!\right]_p\!\!-,$$

wherein
R is H,
n, is 2; and
p is an integer, and the average molecular weight of the polymer is $1.5 \cdot 10^2$ to $10^7$ Da,
wherein at least 92% of the N atoms in the polyethyleneimine are protonatable.

9. The composition according to claim 1, further comprising one or more additives, wherein the one or more additives are selected from the group consisting of buffering substances, saccharides, stabilizers, cryoprotectants, lyoprotectants, and chelating agents,
wherein the buffering substances comprise at least one selected from the group consisting of 4-(2-hydroxyethyl)-1-piperazineethanesulfonic acid (HEPES), 2-(N-morpholino)ethanesulfonic acid (MES), 3-morpholino-2-hydroxypropanesulfonic acid (MOPSO), acetic acid, acetate buffers and analogues, phosphoric acid and phosphate buffers, and citric acid and citrate buffers, and/or
wherein the saccharides comprise at least one selected from the group consisting of monosaccharides, disaccharides, trisaccharides, oligosaccharides, and polysaccharides selected from glucose, trehalose, and saccharose, and/or
wherein the cryoprotectants comprise at least one selected from the group consisting of comprising ethylene glycol, propylene glycol, and glycerol, and/or
wherein the chelating agent comprises EDTA.

10. The composition according to claim 1, wherein the composition comprises HEPES buffered glucose (HBG), MES-buffered glucose (MBG), Acetate buffered glucose or HEPES buffered trehalose (HBT), wherein the HBG comprises 5% glucose (w/v) and 10 mM HEPES, pH 7.1, and wherein the HBT comprises 10% trehalose (w/v) and 10 mM HEPES, pH 7.1.

11. The composition according to claim 7, wherein the z-average as derived from dynamic light scattering measurements of the particles is less than 200 nm, and/or the polydispersity index as derived from dynamic light scattering measurements of the particles is less than 0.5, and/or wherein the Zeta-potential of the particles is 20 mV or more, and/or wherein the particles are neutral or positively charged at physiological pH.

12. The composition according to claim 1, wherein the single stranded RNA is a molecule of 6000 to 15000 bases.

13. A method of treating a disease or condition associated with an immune response comprising administering to a subject in need of treatment the composition according to claim 1 in an amount effective for treatment.

14. The composition according to claim 1, wherein the composition is a vaccine composition.

15. A method for inducing an immune response in a subject in need thereof, comprising administering to the subject an effective amount of the composition according to claim 1.

16. The method of claim 15, wherein the immune response is directed against the antigen or epitope.

* * * * *